US008865674B2

(12) United States Patent
Freier et al.

(10) Patent No.: US 8,865,674 B2
(45) Date of Patent: Oct. 21, 2014

(54) ANTISENSE MODULATION OF GCGR EXPRESSION

(71) Applicant: Isis Pharmaceuticals, Inc., Carlsbad, CA (US)

(72) Inventors: Susan M. Freier, San Diego, CA (US); Sanjay Bhanot, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 83 days.

(21) Appl. No.: 13/623,337

(22) Filed: Sep. 20, 2012

(65) Prior Publication Data

US 2013/0116301 A1 May 9, 2013

Related U.S. Application Data

(60) Provisional application No. 61/537,007, filed on Sep. 20, 2011.

(51) Int. Cl.

| | |
|---|---|
| ***C07H 21/02*** | (2006.01) |
| ***C07H 21/04*** | (2006.01) |
| ***A61K 31/70*** | (2006.01) |
| ***C12N 15/113*** | (2010.01) |
| *C12Q 1/68* | (2006.01) |
| *A61K 31/711* | (2006.01) |

(52) U.S. Cl.

CPC ........... *C12N 15/1138* (2013.01); *A61K 31/711* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/3525* (2013.01)

USPC ........ 514/44 A; 536/23.1; 536/24.1; 536/24.5

(58) Field of Classification Search

None

See application file for complete search history.

(56) References Cited

U.S. PATENT DOCUMENTS

| | | | | |
|---|---|---|---|---|
| 5,492,810 | A | 2/1996 | Caetano-Anolles et al. | |
| 5,563,036 | A | 10/1996 | Peterson et al. | |
| 5,652,222 | A | 7/1997 | Calabretta et al. | |
| 5,693,463 | A | 12/1997 | Edwards et al. | |
| 5,708,158 | A | 1/1998 | Hoey | |
| 5,716,780 | A | 2/1998 | Edwards et al. | |
| 5,734,039 | A | 3/1998 | Calabretta et al. | |
| 5,770,445 | A | 6/1998 | Kindsvogel et al. | |
| 5,776,725 | A | 7/1998 | Kindsvogel et al. | |
| 5,801,154 | A | 9/1998 | Baracchini et al. | |
| 5,804,383 | A | 9/1998 | Gruenert et al. | |
| 5,872,242 | A | 2/1999 | Monia et al. | |
| 5,919,635 | A | 7/1999 | Kindsvogel et al. | |
| 5,985,558 | A | 11/1999 | Dean et al. | |
| 5,998,148 | A | 12/1999 | Bennett et al. | |
| 6,133,246 | A | 10/2000 | McKay et al. | |
| 6,248,724 | B1 | 6/2001 | Moore et al. | |
| 6,251,873 | B1 | 6/2001 | Furusako et al. | |
| 6,268,490 | B1 | 7/2001 | Imanishi et al. | |
| 6,284,538 | B1 | 9/2001 | Monia et al. | |
| 6,287,860 | B1 | 9/2001 | Monia et al. | |
| 6,410,324 | B1 | 6/2002 | Bennett et al. | |
| 6,455,689 | B1 | 9/2002 | Schlingensiepen et al. | |
| 6,492,152 | B1 | 12/2002 | Canfield et al. | |
| 6,525,191 | B1 | 2/2003 | Ramasamy | |
| 6,582,908 | B2 | 6/2003 | Fodor et al. | |
| 6,670,461 | B1 | 12/2003 | Wengel et al. | |
| 6,677,153 | B2 | 1/2004 | Iversen | |
| 6,770,486 | B1 | 8/2004 | Griffey et al. | |
| 6,770,748 | B2 | 8/2004 | Imanishi et al. | |
| 6,794,499 | B2 | 9/2004 | Wengel et al. | |
| 6,869,762 | B1 * | 3/2005 | Daly et al. | 435/6.17 |
| 6,909,031 | B2 | 6/2005 | Allen et al. | |
| 7,034,133 | B2 | 4/2006 | Wengel et al. | |
| 7,053,207 | B2 | 5/2006 | Wengel | |
| 7,341,835 | B2 * | 3/2008 | Blume et al. | 435/6.1 |
| 7,399,845 | B2 | 7/2008 | Seth et al. | |
| 7,399,853 | B2 | 7/2008 | Freier et al. | |
| 7,427,672 | B2 | 9/2008 | Imanishi et al. | |
| 7,750,142 | B2 | 7/2010 | Freier | |
| 7,919,476 | B2 | 4/2011 | Bhanot et al. | |
| 2001/0016575 | A1 | 8/2001 | Miraglia et al. | |
| 2001/0053519 | A1 | 12/2001 | Fodor et al. | |
| 2003/0022848 | A1 | 1/2003 | Baker et al. | |
| 2003/0087856 | A1 | 5/2003 | Bennett et al. | |
| 2003/0144242 | A1 | 7/2003 | Ward et al. | |
| 2003/0203862 | A1 | 10/2003 | Miraglia et al. | |
| 2003/0228597 | A1 | 12/2003 | Cowsert et al. | |

(Continued)

FOREIGN PATENT DOCUMENTS

| | | |
|---|---|---|
| WO | WO 94/05789 | 3/1994 |
| WO | WO 00/05418 | 3/2000 |

(Continued)

OTHER PUBLICATIONS

Agrawal et al., "Antisense therapeutics: is it as simple as complementary base recognition?" Mol. Med. Today: Reviews (2000) 6:72-81.

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.

Altmann et al., "Second-generation antisense oligonucleotides: structure-activity relationships and the design of improved signal-transduction inhibitors" Biochem. Soc. Trans. (1996) 24:630-637.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16(7-9):917-926.

(Continued)

*Primary Examiner* — Sean McGarry

(74) *Attorney, Agent, or Firm* — Isis Pharmaceuticals, Inc. Patent Dept.

(57) ABSTRACT

Provided herein are methods, compounds, and compositions for reducing expression of GCGR mRNA and protein in an animal. Such methods, compounds, and compositions are useful to treat, prevent, delay, or ameliorate metabolic disease, for example, diabetes, or a symptom thereof.

33 Claims, No Drawings

(56) References Cited

U.S. PATENT DOCUMENTS

| | | | |
|---|---|---|---|
| 2004/0016030 | A1 | 1/2004 | Lowe et al. |
| 2004/0171570 | A1 | 9/2004 | Allerson et al. |
| 2004/0266714 | A1 | 12/2004 | Freier et al. |
| 2005/0014257 | A1 | 1/2005 | Crooke et al. |
| 2005/0014713 | A1 | 1/2005 | Freier et al. |
| 2005/0043524 | A1 | 2/2005 | Bhanot et al. |
| 2005/0053981 | A1 | 3/2005 | Swayze et al. |
| 2005/0074801 | A1 | 4/2005 | Monia et al. |
| 2005/0130923 | A1 | 6/2005 | Bhat et al. |
| 2005/0142581 | A1 | 6/2005 | Griffey et al. |
| 2005/0203042 | A1 | 9/2005 | Frieden et al. |
| 2006/0063730 | A1 | 3/2006 | Monia et al. |
| 2007/0031844 | A1 | 2/2007 | Khvorova et al. |
| 2007/0087987 | A1 | 4/2007 | Monia et al. |
| 2007/0243546 | A1 | 10/2007 | Cao et al. |
| 2007/0287831 | A1 | 12/2007 | Seth et al. |
| 2008/0039618 | A1 | 2/2008 | Allerson et al. |
| 2011/0160283 | A1 | 6/2011 | Bennett et al. |

FOREIGN PATENT DOCUMENTS

| | | |
|---|---|---|
| WO | WO 00/49937 | 8/2000 |
| WO | WO 01/92524 | 12/2001 |
| WO | WO 02/16553 | 2/2002 |
| WO | WO 02/45494 | 6/2002 |
| WO | WO 03/023004 | 3/2003 |
| WO | WO 2004/096016 | 11/2004 |
| WO | WO 2004/096996 | 11/2004 |
| WO | WO 2004/106356 | 12/2004 |
| WO | WO 2005/005599 | 1/2005 |
| WO | WO 2005/021570 | 3/2005 |
| WO | WO 2005/023986 | 3/2005 |
| WO | WO 2005/023995 | 3/2005 |
| WO | WO 2006/034348 | 3/2006 |
| WO | WO 2007/035771 | 3/2007 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

Baker et al., "2'-O-(2 Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Baron et al., "Role of hyperglucagonemia in maintenance of increased rates of hepatic glucose output in type II diabetics." Diabetes (1987) 36(3):274-283.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brubaker et al., "Structure-Function of the Glucagon Receptor Family of G Protein—Coupled Receptors: The Glucagon, GIP,GLP-1, and GLP-2 Receptors" Recept. Channels (2002) 8:179-188.

Butler et al., "Specific inhibition of PTEN expression reverses hyperglycemia in diabetic mice" Diabetes (2002) 514:1028-1034.

Chambers et al., "Glucagon Receptor Gene Mutation in Essential Hypertension" Molecular Biology & Hypertension Laboratory, Nature Genetics (1996) 12:122.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke et al., "Progress in antisense technology" Annu. Rev. Med. (2004) 55:61-95.

Elayadi et al., "Application of PNA and LNA oligomers to chemotherapy" Curr. Opinions Invens. Drugs (2001) 2:558-561.

Freier et al., "The ups and downs of nucleic acid duplex stability: structure-stability studies on chemically-modified DNA:RNA duplexes" Nucleic Acids Research (1997) 25(22):4429-4443.

Fujisawa, "A Mutation in the Glucagon Receptor Gene (Gly40Ser): Heterogeneity in the Association with Diabetes Mellitus" Diabetologia (Apr. 1995) 983-985.

Gelling et al., "Lower blood glucose, hyperglucagonemia, and pancreatic alpha cell hyperplasia in glucagon receptor knockout mice" PNAS (2003) 100(3):1438-1443.

Hansen et al., "Glucagon Receptor mRNA Distribution in Rat Tissues" Peptides (1995) 16:1163-1166.

Jen et al., "Suppression of gene expression by targeted disruption of messenger RNA: available options and current strategies" Stem Cells. (2000) 18:307-319.

Jiang et al., "Glucagon and regulation of glucose metabolism." Am. J. Physiol. Endocrinol. Metab. (2003) 284(4):E671-E678.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Leumann, "DNA Analogues: From Supramolecular Principles to Biological Properties" Bioorganic & Medicinal Chemistry (2002) 10:841-854.

Liang et al., "Reduction in Glucagon Receptor Expression by an Antisense Oligonucleotide Ameliorates Diabetic Syndrome in db/db Mice" Diabetes (2004) 53:410.

Link, "Pharmacological regulation of hepatic glucose production" Curr. Opin. Invest. Drugs (2003) 4(4):421-429.

Lok, "The Human Glucagon Receptor Encoding Gene: Structure, cDNA Sequence and Chromosomal Localization" Elsevier Science B.V. (1994) pp. 203-209.

Macneil, "Cloning and Expression of a Human Glucagon Receptor" Biochemical and Biophysical Research Communications (1994) 198(1):328-334.

Madsen, "Advances in Non-Peptide Glucagon Receptor Antagonists" Bentham Science Publishers B.V. (1999) pp. 683-691.

Martin, "Ein neuer Zugang zu 2'-O-Alkylribonucleosiden und Eigenschaften deren Oligonucleotide" Helv. Chim. Acta (1995) 78:486-504.

New England Biolabs 1998/99 Catalog (cover page and pp. 121 and 284).

Opalinska et al., "Nucleic acid therapeutics: basic primciples and recent applications" Nature Reviews: Drug Discovery (2002) 1:503-514.

Orum et al., "Locked nucleic acids: A promising molecular family for gene-function analysis and antisense drug development" Curr. Opinion Mol. Ther. (2001) 3:239-243.

Parker et al., "Glycemic control in mice with targeted disruption of the glucagon receptor gene" Biochemical and Biophysical Research Communications (2002) 290(2):839-843.

Quesada et al., "Physiology of the pancreatic a-cell and glucagon secretion: role in glucose homeostasis and diabetes" J. Endocrinol. (2008) 199:5-19.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Shah et al., "Impact of lack of suppression of glucagon on glucose tolerance in humans" Am. J. Phsiol. Endocrinol. Metab. (1999) 277:E283-E290.

Shah et al., "Lack of suppression of glucagon contributes to postprandial hyperglycemia in subjects with type 2 diabetes mellitus." J. Clin. Endocinol. Meab. (2000) 85(11):4053-4059.

Siani, "Gly40Ser Polymorphism of the Glucagon Receptor Gene is Associated with Central Adiposity in Men" Obesity Research (2001) 9(11) 722-726.

Singh et al., "LNA (locked nucleic acids): synthesis and high-affinity nucleic acid recognition" Chem. Commun. (1998) 4:455-456.

(56) References Cited

OTHER PUBLICATIONS

Singh et al., "Synthesis of 2'-Amino-LNA: A Novel Conformationally Restricted High-Affinity Oligonucleotide Analogue with a Handle" J. Org. Chem. (1998) 63:10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26): 8362-8379.
Taylor et al., "Antisense oligonucleotides: a systematic high-throughput approach to target a validation and gene function determination" DDT (1999) 4(12).
Wahlestedt et al., "Potent and nontoxic antisense oligonucleotides containing locked nucleic acids" PNAS (2000) 97:5633-5638.
Zhou e al., "Fine Tuning of Electrostatics around the Internucleotidic Phosphate through Incorporation of Modified 2',4'-Carhocyclic-LNAs and -ENAs Leads to Significant Modulation of Antisense Properties" J. Org. Chem. (2009) 74:118-134.
Database Genseq (online) Jun. 3, 1999, "Primer for human G-protein coupled receptor genes" XP002632070, retieved from EBI accession No. GSN AAX29544 Database accession No. AAX29544.
Database Genseq (online) May 29, 2002 "Human GDMLP-1 25-mer scanning SEQ ID No. 5 sequence SEQ ID No. 14133." XP002632071, retieved from EBI accession No. GSN:ABN14141 Database accession No. ABN14141.
Database Genseq (online) Jan. 7, 2002, "Human Stat3 Amplifying RT-PCR Primer #2 Ref. WPI; 2002-034368/04," XP-002404609, Database accession No. AAD24334.
Database Genseq (online) Jan. 21, 1998, "Nucleotide Sequence of th eRT-PCR Primer A Ref. WPI; 1998-531578/45" XP-002404610, Database accession No. AAV60964.
Database Genseq (online) Jan. 16, 2004, "Novel Mutant Protein Tyrosine Kinase-Related Oligonucleotide SeqID985, Ref. WPI; 2004-718702/70." XP-002404611, Database accession No. ADT00997.
Database Genseq (online) Jan. 27, 2005, "Knock-Down Target Sequence #7049, Ref. WPI; 2004-775940/76." XP-002404612, Database accession No. ADU41870.
Database Genseq (online) Jan. 27, 1999, "Oligonucleotide Derived from Pinene Synthase Ref. WPI; 1999-120496/10," XP-002404613, Database accession No. AAX08680.
Database Genseq (online) Jan. 5, 2002, "Human Polymorphism Associated DNA Sequence #415, Ref. WPI; 2002-619265/66." XP-002404614, Database accession No. ABS60778.
Database Genseq (online) Jan. 30, 2000, "Hepatitis GB Virus PCR Primer SEQ ID No. 648," Ref. WPI; 2000-338307/29. XP-002404615, Database accession No. AAA55422.
Database Genseq (online) Jan. 20, 2002, "Human KTOM1a Portion (ABQ63232) Probe #137, Ref. WPI; 2002-479509/51." XP-002404617, Database accession No. ABQ63424.
Database Genseq (online) Jan. 20, 2002, "Oligonucleotide SEQ ID No. 21800 for Detecting SNP TSC0004359, Ref. WPI: 2001-657177/75." XP-002404618, Database accession No. ABC21783.
Database Genseq (online) Jan. 20, 2002, "DNA Oligonucleotide Sequence #5, Ref. WPI; 2002-088875/12." XP-002404712, Database accession No. ABA92515.
Database Genseq (online) Jan. 25, 2001, "Human IL4 Gene PCR Primer SEQ ID No. 78, Ref. WPI; 2001-316132/33." XP-002404621, Database accession No. AAH18819.
Database EM-PAT, Oct. 6, 1999. XP-02404619, retrieved from EBI. Database accession No. AR065230, abstract.
Database EM-PAT, Aug. 12, 2002, "Sequence 913 from patent WO0224750." XP-002404620, Database accession No. AX475692.
International Search Report for Application No. PCT/US04/12960 dated Aug. 30, 2006.
International Search Report for Application No. PCT/US04/13120 dated Jun. 27, 2005.
International Search Report for Application No. PCT/US06/36545 dated May 7, 2007.
International Search Report for Application No. PCT/US12/56249 dated Nov. 30, 2012.
European Search Report for application filed application EP 10175905.8 dated Oct. 14, 2010.
European Search Report for application EP 10181097 dated Apr. 14, 2011.

* cited by examiner

SEQUENCE LISTING

```
<160> NUMBER OF SEQ ID NOS: 122

<210> SEQ ID NO 1
<211> LENGTH: 2051
<212> TYPE: DNA
<213> ORGANISM: Homo sapien

<400> SEQUENCE: 1

agtttgcacc gaccccgatc tggcagcgcc gcgaagacga gcggtcaccg gcgcccgacc      60

cgagcgcgcc cagaggacgg cggggagcca agccgacccc cgagcagcgc cgcgcggacc     120

ctgaggctca gaggggcagc ttcaggggag gacaccccac tggccaggac gccccaggct     180

ctgctgctct gccactcagc tgccctcgga ggagcgtaca cacccaccag gactgcattg     240

ccccagctgt gcagcccctg ccagatgtgg gaggcagcta gctgcccaga ggcatgcccc     300

cctgccagcc acagcgaccc ctgctgctgt tgctgctgct gctggcctgc cagccacagg     360

tcccctccgc tcaggtgatg gacttcctgt ttgagaagtg gaagctctac ggtgaccagt     420

gtcaccacaa cctgagcctg ctgccccctc ccacggagct ggtgtgcaac agaaccttcg     480

acaagtattc ctgctggccg gacacccccg ccaataccac ggccaacatc tcctgcccct     540

ggtacctgcc ttggcaccac aaagtgcaac accgcttcgt gttcaagaga tgcgggcccg     600

acggtcagtg ggtgcgtgga ccccgggggc agccttggcg tgatgcctcc cagtgccaga     660

tggatggcga ggagattgag gtccagaagg aggtggccaa gatgtacagc agcttccagg     720

tgatgtacac agtgggctac agcctgtccc tgggggccct gctcctcgcc ttggccatcc     780

tggggggcct cagcaagctg cactgcaccc gcaatgccat ccacgcgaat ctgtttgcgt     840

ccttcgtgct gaaagccagc tccgtgctgg tcattgatgg gctgctcagg acccgctaca     900

gccagaaaat tggcgacgac ctcagtgtca gcacctggct cagtgatgga gcggtggctg     960

gctgccgtgt ggccgcggtg ttcatgcaat atggcatcgt ggccaactac tgctggctgc    1020
```

```
tggtggaggg cctgtacctg cacaacctgc tgggcctggc caccctcccc gagaggagct   1080

tcttcagcct ctacctgggc atcggctggg gtgcccccat gctgttcgtc gtcccctggg   1140

cagtggtcaa gtgtctgttc gagaacgtcc agtgctggac cagcaatgac aacatgggct   1200

tctggtggat cctgcggttc cccgtcttcc tggccatcct gatcaacttc ttcatcttcg   1260

tccgcatcgt tcagctgctc gtggccaagc tgcgggcacg gcagatgcac cacacagact   1320

acaagttccg gctggccaag tccacgctga ccctcatccc tctgctgggc gtccacgaag   1380

tggtcttcgc cttcgtgacg gacgagcacg cccagggcac cctgcgctcc gccaagctct   1440

tcttcgacct cttcctcagc tccttccagg gcctgctggt ggctgtcctc tactgcttcc   1500

tcaacaagga ggtgcagtcg gagctgcggc ggcgttggca ccgctggcgc ctgggcaaag   1560

tgctatggga ggagcggaac accagcaacc acagggcctc atcttcgccc ggccacggcc   1620

ctcccagcaa ggagctgcag tttgggaggg gtggtggcag ccaggattca tctgcggaga   1680

ccccccttggc tggtggcctc cctagattgg ctgagagccc cttctgaacc ctgctgggac   1740

cccagctagg gctggactct ggcacccaga gggcgtcgct ggacaaccca gaactggacg   1800

cccagctgag gctgggggcg ggggagccaa cagcagcccc cacctacccc ccaccccccag   1860

tgtggctgtc tgcgagattg ggcctcctct ccctgcacct gccttgtccc tggtgcagag   1920

gtgagcagag gagtccaggg cgggagtggg ggctgtgccg tgaactgcgt gccagtgtcc   1980

ccacgtatgt cggcacgtcc catgtgcatg gaaatgtcct ccaacaataa agagctcaag   2040

tggtcaccgt g                                                        2051
```

```
<210> SEQ ID NO 2
<211> LENGTH: 20001
<212> TYPE: DNA
<213> ORGANISM: Homo sapien
<220> FEATURE:
<221> NAME/KEY: misc_feature
<222> LOCATION: (1)...(20001)
<223> OTHER INFORMATION: n = A,T,C or G

<400> SEQUENCE: 2

nnnnnnnnnn nnnnnnnnnn nnnnnnnnnn nnnnnnnnnn nnnnnnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn nnnnnnnnnn nnnnnnnnnn nnnnnnnnnn nnnnnnnnnn    420

nnnnnnnnnn nnnnnnnnnn nnnnnnnnnn nnnnnnnnnn nnnnnnnnnn nnnnnnnnnn    480

nnnnnnnnnn nnnnnnnnnn nnnnnnnnnn nnnnnnnnnn nnnnnnnnnn nnnnnnnnnn    540

nnnnnnnnnn nnnnnnnnnn nnnnnnnnnn nnnnnnnnnn nnnnnnnnnn nnnnnnnnnn    600

nnnnnnnnnn nnnnnnnnnn nnnnnnnnnn nnnnnnnnnn nnnnnnnnnn nnnnnnnnnn    660

nnnnnnnnnn nnnnnnnnnn nnnnnnnnnn nnnnnnnnnn nnnnnnnnnn nnnnnnnnnn    720

nnnnnnnnnn nnnnnnnnnn nnnnnnnnnn nnnnnnnnnn nnnnnnnnnn nnnnnnnnnn    780

nnnnnnnnnn nnnnnnnnnn nnnnnnnnnn nnnnnnnnnn nnnnnnnnnn nnnnnnnnnn    840

nnnnnnnnnn nnnnnnnnnn nnnnnnnnnn nnnnnnnnnn nnnnnnnnnn nnnnnnnnnn    900
```

-continued

```
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnntacttgg ccctcctaat tgggtgttct   1020
cagtgaaaac gaggacactg ctaatatgct ttagaaaata gccctcacat tctccctgtt   1080
cccaatcccc cacttactct aagctcccca ggtagcaata attcagaagt caaattgctc   1140
agcactccta tggttcaagt gattcttgtg tctcagcctc ccaagtagct gggactacag   1200
gagcccacca ccacgcccag ttaatttttg tatttttag tagagatggg gtttcaccat   1260
gttgaccagg ctggtctcga actcctgacc tcaagtgatc cactggcctc ggcctccaaa   1320
agtgttggga ttacaggcgt gagccactgc gcccagcctc aaccttctag tgaaccctcc   1380
atgctctgtt atcttttatt cctcttggat ttttgttgtt tcttttcttt ttcttcttct   1440
ttttctttc ttttttttt tttgagatgg agtttcattc ttgttgccca ggctggagtg   1500
caatggcaca accttggctc actgcaacct tcgcctcctg ggttcaagca atttgcctgc   1560
ctcagcctcc caagtagctg ggattacagg catgtgctac catgcctggc gaattttgta   1620
tttttagtag agacagggtt tctccgtgtt ggtcgggctg atctcaaact cccgacctca   1680
ggtgatcagc ccgccttggc ctcccaaagt gctgagatta caggcatgag ccaccacacc   1740
cagccttttt gttgtttctt ctgagagatt tcttcaactc aattttccaa cccttctatt   1800
aaatttttta aattccagat attctatttg cagccggcaa ggactcttcc tgcgctctgc   1860
ttgttttcca aagcattccg ttctagtttt tatgggagca tcatcctttc atgtctctaa   1920
ggataatcag agtggttaaa atgttcttga agttttcttc tgttccctgc agtagctctg   1980
tttcctccag tttcctcttt cccaagtgat tggtctgtct catataccta gaggtcttgc   2040
tttgcattca catctaaggg caaaaggcgc taggatgcag tgcggaggtc cattcgcttt   2100
gtcgtaaggt ttgtgccttt cttagtcctg cagtggttga gtaaaacctg accatcccac   2160
accctcaaat actaagtgcc cctgggtagt gatgtggagg ggccttctta ttaatgtgag   2220
gaaatgcttg tgttataggt tgtggtgaga aacgctggtt acaaaactat atcaaagtaa   2280
aaatgtatta atgcacagta aagacacctg gaaaaaaaat gccctttaat gctcacagaa   2340
ggtctctccg aggggcagcc ccaccaccct cctgtttccc ttcctgcatt tccacgtttt   2400
tctgggccca gatgcagcct cccctcccac ccctggtccc tccgccttgg cttccggctg   2460
tcgctttcat ccctcctcct catcagcccc ttgcagaact ccagggtggg gcttctgagt   2520
ctcgctggca gtatgggctc cataagtctt gctggacacc gaaattaagt tctgcaggtg   2580
ccgtctccag aatccccagc acagatagac aaacccacat ctcaggggtg gggggtgcag   2640
acctgccccc agnnnnnnnn nnnnnnnnnn nnnnnnnnnn nnnnnnnnnn nnnnnnnnnn   2700
nnnnnnnnnn nnnnnnnnnn nnnnnnnnnn nnnnnnnnnn nnntcccagc tgccctctgt   2760
ttatatgtct caccaatgtc aagggaaacc agaactggat agcagttgaa acacatattt   2820
tgttcgggac tattgtaata ggggaaaaaa gattttagta tagacctggg ctcaactctc   2880
aatgtggcac aggcaagtgg ggatttagat ctgaggagca gggcggggtc agtgggtgga   2940
aaattactgg cacgaaacac ctgtctggag gattctggct aaacccagga aacaggaagc   3000
ttgctgaggg caggcagggt tagcagacat cgcctggggg tggcggaggc tgagaaccct   3060
acccaggtaa aatgaagctt gctgacggca gacagggtta gcagacacgg cctggaggtg   3120
gcagaggcta aggaacctac ccaggtaaaa cgaagcttgc tgacggcaga cagggttagc   3180
agacacggcc tggaggtggc agaggctaag gaacctacca aggtaaaatg aagcttgctg   3240
aaggcagcca gggtgagcag atattgcctg ggggtggcgg aaactgagga ccctacccag   3300
```

```
gtaaaaggaa gcctgctgaa ggcaggcagg gtgagcagac attgcctgtg ggtagcagag   3360
gctgaggact ctacccaggt aacaggaatc ttgcttaagg caggcaaggt gagcagacat   3420
cgcctggggg tggcggaggc tgaggactct acccagataa caggaatctt gctgcgggca   3480
gccagggtga gcagacgtcg cctgggggtg gtggaagctg aggaccctac ccaggtaaaa   3540
ggaagcttgc tgaaggcagg caaggtaagc agacatcgcc tgggggtggc ggaggctgag   3600
gaccctgatc agatatgggg ggatggaggc ttcttgccaa actgacttag cagagttctt   3660
gctgaatctg gattttataa ggcagaatgc agatgagcct gtgagaaggt tctgaagccg   3720
gactacagtt tggtcaagca aacaatcttg tcatggattc agtcatataa ataagggtca   3780
cccagcccag gggaggtgcc ccaccccatc tgttccctct ccctccccac actgagtccg   3840
aacctttcag gctttgcccc cttcacacac tccaaattta ttcttctact tctcttcctg   3900
caggtaccag actccggcca cccagcgctt acctgggact gctgggcctc tgccccgtgg   3960
ggacctgtcc tccaggaaac aaggccagac acaggagggc agggaggact cttctccagg   4020
gccggtgcgc cgtctcttca gccccatggc acttgactta ggcagagcct acagcaccct   4080
caccccagtc cctgcagcca ccaggaggtg gtccccctca tcccattagc catcaccgcc   4140
attcacagag gtctcggact gaggctggca gggggagcac catgacccaa gatcagaacc   4200
ctgttgtctg tgcctctgga gaggtggggg caggagctga gggagggttt gggtggagag   4260
gggagaagat gcagtagcag gagcagatgc tggcaggtag agacaaactt ttatgacctt   4320
tgccttctga cctttgcctc tggccactgc tccaactaaa acagaatggc cccctctggg   4380
aacagggctt cctatgggct gggaagcatg gagcccccac agtgtggcta tgcaggggag   4440
tgaggaccag gtgggggcag gcctgtgggg gtcacagagc tgggctaagc ttcagaggga   4500
agtggcccct gggaggggga atggctgggg ttaagaccct gggttcccac gcccccaaaa   4560
cagaagtaga attagggaga aaggaccccc aagaccaagg acggcaccta tcagaggagc   4620
tctccacggg caggaggtgt cccagggtga gggtggccag gacaggtcta gggaaatgca   4680
ggtggagcag gacccagaga tggattggag atgccggagg ggaggcttcc tagcgggagc   4740
ggagacaggc actgcagaca agtgtcagcg ggaggggctc tgggtgggga agaagactgg   4800
gacttggagg aagacctctc cagggagaag ggaggagggg gaaggagaag gggaggaagt   4860
gggaggagga gagtgctcat cctggaagcc acagcctcgg agagaacttt ctagaaggaa   4920
ggcatgacca tcagtgtccc aggatgctga gaggccagga aaggtgaggc ctcaaggcgc   4980
catggggttg tggtgacccc aagatcactg ggcacagagc agggatggct gggggtggaa   5040
ggggaggggc gcgggctgag gttctagggc cccaaagcca ggtgtgatgt ggctctaggg   5100
ggagtgagga aggggagaat gtccctctga gcgtgcctct tggggaaggc aggggttctg   5160
gctggggctt ctccactccc aggaaaggag gtggtgtgga aggagcgggt gggacggagg   5220
agagagcgcc ccgcggccgc aggaccagca ggtgggggac cagggtcagc gctgctggag   5280
gggccttagc gcgacaggac tggccagaga ccggggatgt ggcacagaaa gagttaaagg   5340
gcaccccagg gaccgccctg ccggtccacc catgtcaccc atgttggccc ctactccagc   5400
ccccgtctgc tctgcagggg aaggaaccgg gagccgcggt gggggcgact gggggtgtcg   5460
gtctttccag aaaatcaggc aggcatcagg aaagaagggg cgagaacccg gggacgcgag   5520
aggaaggggg cgagggggnn nnnnnnnnnn nnnnnnnnnn nnncgcgtcc cagggcgtcc   5580
cctcccggga ctgggaccca ccgcgaccac cacctgctgg gccagggtcc gcgggctcag   5640
```

```
gggtctgcag gattagggtc tgcggaacca ggacccgtgg gacaaaggtc tgtggggcgc   5700
gggtccgcgg ggtggaattc agcgcgccga gtctgcgtat ggccggggta cgaggcgctc   5760
cctgcgcagg gtgggcagga ccgaagctcg ccgggagctg cgcggagggc gggcggggac   5820
cctccggtgc cgctcccacc ccgcggggcc gcccccgagc ccgccctccg ccgccgccct   5880
cgccctcgtc gccgccggaa agtttgcacc gaccccgatc tggcagcgcc gcgaagacga   5940
gcggtcaccg gcgcccgacc cgagcgcgcc cagaggacgg cggggagcca agccgacccc   6000
cgagcagcgc cgcgcggtga gcacctgggc cgcggacccg aggggacgtt ggggagtcga   6060
cccggtgggg acagagaccg cggggcgggc gcggcggggc cgggggcgcg gggagcgggg   6120
agccggccgg gcggtctccg gggtccgggc tggtgcgctc ctcagtcccg tcagacaccc   6180
ccgttcccaa ccccggctcg gacaccaccc ggtcctgcac cgtcgggcag gtccaggggt   6240
ctcagcccct cccccgttct ctggtcctgg ggggcgcggc tgggggcggg ggtgtcgctg   6300
gccgcctggc gccctgcggc ggccacactg cagcggccac actccccact cagggccccg   6360
ggccccgccg ccctggggag cgcacaaagc gccgcggacg cgtccccgag gcgcggggtc   6420
tcaccagcgc tgtctcccct cggtgggctc ctgccccgag gactgcccgg tggcaccggc   6480
gcggcccagg atggggtgag ggtgtctgc gccccgcctg gccgctcctc ttccgcggcc   6540
cacactggcg actttgaccc cggcaagcgg gtcactgccc tgcccggctc cggccccccc   6600
ggcgccccac cacccggccg actcggccac cgggcttatg ctccgactct gaaccgactg   6660
accccggccc cctcggcgcc cgcatcctcc aaggaccggc cagggctgct ctctgccctt   6720
ggtattgggg acatcagggt tggggggtct gggtgcaccc acgcctgccc cgcccccacg   6780
gggtgagggc gcagggatag ggctttgtca acagcctgtg gcccctgatc ccgccccggt   6840
gccctgacct tccactacct tctctggttt cacaaaaaca tcccggctcc catcccggag   6900
ctcctcaaag cgtctgagag gccccttgcg gacgccctgg gagccccgct gccttcctgg   6960
accagtggcc gctccaccca tcctgggggc ccagctccag gtctgcgggt ccctcagccg   7020
cccccagtgg gaatcggtgg agcctgacgc agccaggagc gcccaagagt cacgtgttct   7080
gccagggagg acatgggaca ggacacgggg tgccagccct gcaaagcggc cggggcagtg   7140
gagctcaggt ggccctaagc cctggtggtg gctggtgtgg cccggcaggc agctgtggga   7200
gggaggaagg gggtggcatg cggtgggggt ctagagaagg cgggcagggc acctcgggag   7260
cccccccatt gggcacctcg ggaacccccc acattgggca cctcgggaac cctcccattg   7320
ggcacctcgg gaacccccca cattgggcac ctcgggaacc cccgcattgg gcacctcggg   7380
aaccctccca ttgggcacct cgggaacccc cctattgggc acctcgggaa cccccacatt   7440
gggcacctcg ggaacccccc ctattgggca ccttgggaac ccctccccta attctcagct   7500
gactccaagg cctgagaagg agcttggtca cctggactgt gaaggtggag ggtggggtcc   7560
ctggtgggtc gtcccaccta ccagctgtgt cgccggaagg gtaatacgga gcactgtggc   7620
cccggggagc cccgagtggc agctccacag ctgggagttt ctgtccactc cttcagtcaa   7680
caaacattga tcctgggctg accggggccc gggggtgtca gtgtctcctc tcgggggaga   7740
gggctgggtg agatcaacag aggagcctcc cttcttccct tcaggctggt gtcaccttca   7800
gtgatggggc agggtcccca cttgggaagt taaatcgtcg tccccgtccc aggaccacag   7860
cagcctcagc cctgctctcc aggccaggct ctctcatggg tgctcagctg gaaattggtc   7920
cccccccggc tccacccacc cctgttgggg tgaggagctg gagtctccct acccatatgg   7980
gacccaccac ccgcagggaa cggaggacgc tcacacttct gcacctcctg cctcactatc   8040
```

```
agagacccag tggagaattg cctcccacct cacctcttgt attcagaggc cctgacccct   8100
agggatccgg gactaggggt gccctatggg gagcccacct gtggcctgtg gatgctgagc   8160
tgtcgggga atcctccagg atccccagcc ccaccttccc aaccttctgt tgaggctgag   8220
gggacacaga gccccactcc tgggtcctga ctgtttcaaa gaaaggcctg gggactggg   8280
cagccaaccc ctccctcggc tcgctggggt ctccagactg gctgcccggc tggaaggtgg   8340
ggccctggca cgcgaggacc tcatgtgtgg aggcactggc ttggggggtg ctcccagtgg   8400
ctctagagtc aacatgacag gcatcgaatg gctcctgttt ctctggcaga gttggggcag   8460
agccaggctt ggccacgctg ggctctaagg ggctgtcatt ttgcccaggg agctcctggc   8520
tgggtggtcc tccccccagg gtgagcacgc gtcccccca cccccacttc gaggcgccca   8580
ggcagggaac agctcattgg ccagtgtcct tcctccttgt cccccgcctg catctccacc   8640
atccaccctg ctccagctgc cccttgtccc tctccccgtc ccctgcccag agccccaggt   8700
ctcccctgca cccctgagcc tgcccaccta gcagtgcccc tcgtccaggg cccctctggg   8760
ttgggggtgc acacagtggg gagaggcggc tcctgctgct cctcacccag cccggctcag   8820
tggccggagc cgcccaggac agtggcagta gatggggctg tttgatcagg atcagggaag   8880
ataaggcccc ttgcgtgacc ccagagctgg ggacgccaaa actgcccctc ctcccccacc   8940
cgcctgccgc tgtctccgcc agggagaggc ccctactctg tgggtccttc gccccagcac   9000
caagcctgca tggctgctca cctggctcag gaactgggga tcagcgacac acgggtcctg   9060
cctcccatcg gcccctacat gagcccaggg tccaagggct gcggttggga gctctttagc   9120
agtctgtgac gcaggtgcct gtccctgtca ttcagctgtc acactgcttg ggcatctca   9180
ggccccgtta gcggggcagc cctgggtgga gctggcccca cgcgggctca cccagccgct   9240
acctggagga ggctaaaatc caggctgtcc cgtggcagcc agcagtccag gcctgcccgg   9300
aaaccctctg ctccagctgc agccttcgcc catctccttg cccctctccc cggcttcccc   9360
ctggcactgc cttccagctg gctggccctc catctgccca gccatccatc cacacctctt   9420
attccatttg agggtgcccc aaagaagagc ccgtaacagc ccgggggctc atagccagcc   9480
actcgcggga ccccgcacat gcacgtggac ccacaggaag accctccctg cttctcccac   9540
agaattcagt tggtgcagaa actgggctct gtagcaacga aaggccgatt tgtgtagctg   9600
ttgccacccc gaactcccag ctcagatgct ggctgtggca tggggaccag ggctgtgac   9660
tcccacagcc ctggcaggca ccacggggga tgtcctcccc accctgtgcc cccaccctag   9720
gccagctcct cctccaagtc gacgcccgca gtgctaacct caaaggactg tgcagccagc   9780
ctgtggcgtc ccatgggatc caggaagccc aaccgagcct tgcacggcac ccacgaggca   9840
cctaggcacc ccggtgctgg gcagggggca cacatgtgac acagacccct gagtgtgggc   9900
cccacacact tggcctggca cagctgcaag ccagcccagc cactttgctc gctgtggcac   9960
tggggccaag tgatggaagg tccaggcacc gccaccctca cgcttggcac attggctcag  10020
gtcagcctgg caagccagct ttcccagggg ctaagaatag gtgaggagga tggtgaggaa  10080
gcagccgggg gctgtcaact gagggaggag gtcaccatct ggggaggctg gtcccccacc  10140
caagagcatt gggtcaccct gcaggaaggt ggctgccacc agcaatgaga cgaggggctc  10200
tgcgaccctc agagctgcca gccagccagc cctgggtggc aagagtgact cctcctgggg  10260
tctcctccct cctatcgccc tcttttttt ttttttttt tttgagacgg agtctcgctc  10320
tgtcacccag gctggactgc aatggcgcaa tctccgctca ctgcaagctc tgcctcccgg  10380
```

```
gttcacatca ttctcctgcc tcaagctccc gagtagctgg gactacaggc gcctgccacc  10440
acgcctggct aattttttgt atttttagta gacatggggt ttcactgtgt tagccaggat  10500
ggtctcaatc tccagacctc gtgatccacc cccctcggcc tcccaaagtg ctgggattac  10560
aggtgtgagc caccacgccc agcccccagc tccctcttta tccctaggac cctgaggctc  10620
agaggggcag cttcagggga ggacacccca ctggccagga cgccccaggc tctgctgctc  10680
tgccactcag ctgccctcgg aggagcgtac acacccacca ggactgcatt gccccagctg  10740
tgcagcccct gccagatgtg ggaggcagct agctgcccag aggcatgccc ccctgccagc  10800
cacagcgacc cctgctgctg ttgctgctgc tgctggcctg ccaggtgagg actcacagca  10860
ccctcagcac ccaggggccc tcctgtgagg actgcacact gatggctctc tgtctgcctg  10920
cctgcctgcc tgcctgtctg cctgcctgtc tgtctgtctg cccgtctgcc tgcccatctg  10980
cctgtctgtc tgcctgtccg tctgtctgtc catctgtcca tctgcctatc catctgcctg  11040
cctgtctgcc tgtccgtctg cctgtctgtc tgcctgtcca tctgtccatc tgcctatcca  11100
tctgcctgcc tgtctgtcgg cctgcctgcc tgcctgtctg tctgctgcct gtctgtccgt  11160
ctgcctgtct gcctgtccgt ctgcctgcct gtccgtctgc ctgtccgtct gcctgcctgc  11220
ctgtctgtct gcctgcctgt ctgcctgcct gtccgtctgc ctgtccgtct gcctgcctgt  11280
ctgcctgcct gtctgcctgt ctgcccgtct gcctgtctgt ctgcctgtcc gtctgcctgt  11340
ctgtccgtct gtccatctgc ctatccatct gcctgcctat ctgtctgtcc gtctgcctgc  11400
ctgtctgtct gcctgtctgc ctgtctgtct gcctgtctgt ccatctgcct atccatctac  11460
ctgcctgcct gtctgcctgt ctgtctgcct gtctgtctgc ctgcctgtct gtctgtctgt  11520
ctggttgctt gtgcatgtgt cccccagcca caggtcccct ccgctcaggt gatggacttc  11580
ctgtttgaga agtggaagct ctacggtgac cagtgtcacc acaacctgag cctgctgccc  11640
cctcccacgg gtgagccccc cacccagagc ctttcagcct gtgcctggcc tcagcacttc  11700
ctgagttctc ttcatgggaa ggttcctggg tgcttatgca gcctttgagg accccgccaa  11760
ggggccctgt cattcctcag gcccccacca ccgtgggcag gtgaggtaac gaggtaactg  11820
agccacagag ctggggactt gcctcaggcc gcagagccag gaaataacag aacggtggca  11880
ttgccccaga accggctgct gctgctgccc ccaggcccag atgggtaata ccacctacag  11940
ccccgtggag ttttcagtgg gcagacagtg ccagggcgtg gaagctggga cccaggggcc  12000
tgggagggct cgggtggaga gtgtatatca tggcctggac acttggggtg cagggagagg  12060
atagggctgg aggactcacc cgggaggcag tgcctgggtt cggatgaggg aggcagccac  12120
cactgggcag aggggggcag gtgtggcagc ctccattggg cagagggagc agatgtggca  12180
gccacaggtt tggcgatgca cctgggaagg atgaaaatgg cattggggtt cagcccccag  12240
agagggaggt gctgagagaa ggtcacggag aatgggggac cccagtgtgg gtttggggca  12300
catttgagat ggggggtctc caagggaagg tgtcctgcag agctgcaatt cagggctggg  12360
ctgggcgtgc tagcggaggc tggtccaggg gaggtggatg gtcaggtgag gaaggtggag  12420
gtcagatggg ggaggtggag gtcaagtggg ggagggagca gcccaggcca tgtcctgggc  12480
gaggtgacgg ccgagctcag gcttccagag agaggagaga ggcctgctga gggagcccct  12540
tctcccaccc tgccctgccc tgctctgccc tgccctaccc taccctgcag agctggtgtg  12600
caacagaacc ttcgacaagt attcctgctg gccggacacc cccgccaata ccacggccaa  12660
catctcctgc ccctggtacc tgccttggca ccacaaaggt acccatagag gggaggaact  12720
gtgggggggg cgggcccagg gtggggctga ccccagcctc cccccacacc cccagtgcaa  12780
```

```
caccgcttcg tgttcaagag atgcgggccc gacggtcagt gggtgcgtgg accccggggg  12840
cagccttggc gtgatgcctc ccagtgccag atggatggcg aggagattga ggtccaggtc  12900
agtgggcggc aggcaggcgc ggtggggctg gatgggaacg ggcatggggg cccctgcctg  12960
gccctcacag gccactgtaa ctcgcagaag gaggtggcca agatgtacag cagcttccag  13020
gtgatgtaca cagtgggcta cagcctgtcc ctgggggccc tgctcctcgc cttggccatc  13080
ctgggggggcc tcaggtagga ttccgccagc gcccggggcg gccgcagagg acagggagga  13140
ggacgggcgc tgactggctg tgcccacagc aagctgcact gcacccgcaa tgccatccac  13200
gcgaatctgt ttgcgtcctt cgtgctgaaa gccagctccg tgctggtcat tgatgggctg  13260
ctcaggaccc gctacagcca gaaaattggc gacgacctca gtgtcagcac ctggctcagt  13320
gatggagtga gcccccctcg gcggccccag gcaggtgggt gggtgggcag ccaggcaggt  13380
ggccacgtag ccgcgctcac actgcacctg taccaggcgg tggctggctg ccgtgtggcc  13440
gcggtgttca tgcaatatgg catcgtggcc aactactgct ggctgctggt ggagggcctg  13500
tacctgcaca acctgctggg cctggccacc ctccccgaga ggagcttctt cagcctctac  13560
ctgggcatcg gctggggtga gtgggctggc atgagagggg gttaaggcag gctgaccaag  13620
cctttgggac cacagctgct gccccccaca ggtgccccca tgctgttcgt cgtcccctgg  13680
gcagtggtca agtgtctgtt cgagaacgtc cagtgagtat gagcggctgg acagcctggg  13740
gagggaccgg ggggctgggg tgcggcgctc tggcctgagg cagggagggg ccggggatga  13800
gcctggtgcc tggggagggg gtcatttgtg accttctccc ttccttttct gagacccgaa  13860
ttagatcctg gcaaaatcgg gacgggggtg ctgaggggcg gaggggctgg gggctgtgcc  13920
ccagtatgtg agtggcctgg cctcgcaggt gctggaccag caatgacaac atgggcttct  13980
ggtggatcct gcggttcccc gtcttcctgg ccatcctggt gaggaaatga agagccagga  14040
gcgcacccca ggcccctcct cccttggcgt cctgaggctg ccccaggaga cagcagcatc  14100
ctgtctgaga gcgctgggag ggagccggca cccagacagg acaccaggac actggccagc  14160
accctggaca ctgagccagg ctgttcctcc ctggctgtgt gcccaccagc cccagggcta  14220
tgtggcccag ggcctatctt gctgccaggc ccacctgcag gagggtcagg tggggccttc  14280
caagggcaca gagctgttcc ctggggctcg ggatgcccct gactcgcacc cttctcacac  14340
agatcaactt cttcatcttc gtccgcatcg ttcagctgct cgtggccaag ctgcgggcac  14400
ggcagatgca ccacacagac tacaagttcc ggtgggtgcc gcggcagctg gcgtctcgag  14460
acctggagac cctcagggcc agagggcagc tgggggtggg gactccaagc tccacgtgga  14520
tggtgcgggc cgagggtggg ggcggtgggt gactcaggcg ctgcctctgc aggctggcca  14580
agtccacgct gaccctcatc cctctgctgg gcgtccacga agtggtcttc gccttcgtga  14640
cggacgagca cgcccagggc accctgcgct ccgccaagct cttcttcgac ctcttcctca  14700
gctccttcca ggtgcccgcc cgcccgccgg ctcccccgcc cggggcgcag tgtgccaccc  14760
ctgaccaccc tgtctctcca gggcctgctg gtggctgtcc tctactgctt cctcaacaag  14820
gaggtaggtg ggagtggggg catctgagac catcagcact ggccgtcggg gtcaggggca  14880
gagagaggca cagggatgcc agccccaccc ctgcccgggg gttggaacac gtggggccca  14940
agcctttccc tccccctgct cttattgggt gcagttgcca tggcgctggg tgtcaggccc  15000
ccaggacagg ttggcctcag ccccatcgct acggtgtcca ccgtgggggt ccccaggtgt  15060
ctgcagactg ctttccgtgg cgatgctggg tggcatagct gtgcccagca gggagcttgt  15120
```

```
gtcgctctgc accccctcaga gcggagactg ggcatctccg atgaggccca cagcaggtcc  15180
cggtggggtg gagaggacag gcaggcccta ggactggcct gccccgtccc cctccccagg  15240
tgcagtcgga gctgcggcgg cgttggcacc gctggcgcct gggcaaagtg ctatgggagg  15300
agcggaacac cagcaaccac agggcctcat cttcgcccgg ccacggccct cccagcaagg  15360
agctgcagtt tgggaggggt ggtggcagcc aggattcatc tgcggagacc cccttggctg  15420
gtggcctccc tagattggct gagagcccct tctgaaccct gctgggaccc cagctagggc  15480
tggactctgg cacccagagg gcgtcgctgg acaacccaga actggacgcc cagctgaggc  15540
tgggggcggg ggagccaaca gcagccccca cctaccccc acccccagtg tggctgtctg  15600
cgagattggg cctcctctcc ctgcacctgc cttgtccctg gtgcagaggt gagcagagga  15660
gtccagggcg ggagtggggg ctgtgccgtg aactgcgtgc cagtgtcccc acgtatgtcg  15720
gcacgtccca tgtgcatgga aatgtcctcc aacaataaag agctcaagtg gtcaccgtgc  15780
atgtcctgga aagcagggct ggaaatgctg gggccgaagc agtgggggat ggaacagcgg  15840
tgggtggtca gcgccagtgc gggctgttga agggtccccc tgctgtccca gttcactcag  15900
agttggcact ggaaccccgg aggatcccga aggcagccag cctgtgccca tctgagcagg  15960
tcctggccac cttcccatcc tggttctggc gggcagtccc cctggacgct ttggccacca  16020
gagggtcacc attcaccagc agagacgtga ggggcacagt ggctaaggcg gcatgaggca  16080
tcacagtccc ctgaccgacc ccatcagcac tggattcacc cgagggcgtc ttctccctgg  16140
aggccgtgag gacactggca cctggctcat cggcccgccc ttcctctgag cctcctggcc  16200
tccgtttcat ctcagctcca gccccctcgg gcaatttaca ggccacgtag cagattgaag  16260
cgggaagaaa tgggcctgaa cattgccgcg ggtccaggcg acggaggagg gcaggttgcc  16320
caacttctgc acaggacccg gggtgcgcca cacacacgcc agtcctcgtg ccacacagag  16380
aggtccggcc tacgccagtc ctcgtgccac acagagaggt ccggcctacg ccagtcctcg  16440
tgccacacag agaggtccgg cctacgccag tcctcgtgcc acacagagag gtccggccta  16500
cgccagtcct cgtgccacac agagaggtcc ggcctacgcc agtcctcgtg ccacacagag  16560
aggtccggcc tacgccagtc ctcttgccac ctcgtggtgg gtgggcgccc tgcttgccag  16620
ccagggagca ccaggaaaga gctgcctcct gcgtgctgga cacaggaggt gcttcagggt  16680
ggggtctccc attgtgtggg gcccaacctg agtctaaggg cccagggacc acacagcggg  16740
ggtggagaca aattcagggt agaagctgtg aggggcctgt ggtcagcccc ccgggggggtc  16800
cctgcagcag gcactgtgag acctactgag gtgtgtgcat gggctgggga aggagccagt  16860
caggtgcccc tgctctgagg agctgctggg aagtgctgct gggccctggg ggaaggggtg  16920
ctcacagccc ctgcctgggc cacgtgggct ggagccgctc aggcagagcc ggactaattg  16980
gggcaaatga ggggacagga ggcctctgag gaaaggtaaa tagaattact cacccgccag  17040
gcactggggc cctcctgggg gggccctcac cctgccaccc accacagggc ctgcatgcag  17100
cagggaggga agtgagctga ttaggcaagg ctggaccctt ctggggccct ggggttgctg  17160
tgattgggac ggcaaggcca ggagacggtc ccctgagctg cacctgctgg aggcctgtga  17220
tctcagacct taaggcttca ggccagctct acgcccctcc ggcctcaggt cctggctctc  17280
ctctgagccc tggatgcccg ggtgcctgtg tgggcacgag gctgctccga gtcagcacac  17340
ggaggtggac attctccttc atgccagctg agctcagggc tggtgactgc cctggggaaa  17400
ctgcccctca cctgggacct cctgacagcc ctccccattc ccgagtccct ctgcccttgt  17460
cctctttcac ctctgtcccg ccctcatccc taagggaact ggagcaggct ggtggagttg  17520
```

```
ggtggagttg gggactggca gggggtggac tcacccaggc aataaacact ggccctaacc  17580
aggcagtcct gcaggcaggt aggtggaggg actgtttttt ttcttttttg gagatagagt  17640
ctcactctgt tgcccaagtt ggagtgcagt ggcatgatct tggctcactg caaactccac  17700
ctcccaggtt catgtgattc tctgcctcag cctcccgagt agctgggatt ataggcgtgt  17760
gccacgacac ctggctaatt tttttttttt tttttttgag acggagtttc actctcgttg  17820
cccaggctgg agctcaatgg cgcgatctca gctcaccgca acctccgcct cccaggttca  17880
agcgattctc ctgccttagc ctccctagta gctgggatta caggcaggta tgtgatgccc  17940
ggcatcccaa aggggtatct gcaagagttg ggtgctgtgt gtgcatggct gggaggaaga  18000
tgactttgat accctggaat ctggtgtctg tggacacaaa aatactacta aaatgagagt  18060
ggagaccagg aaaaaggaag acatgaacta catgaaggac caaatctagg agagtcagaa  18120
gtgcgtcaca ggaatagggg accttgagcc agacagaagg ctcagcagag acaccctcaa  18180
ggggatgaaa gggattgagt gcactaatat ttagaggaga gagttcagga cttgattagt  18240
gactagtaca tagaaaacta aacaaatgag gctgggtgca gtggctcatg cctgtaatcc  18300
cagcactttg gggggccaag gcgggcgaat cacctgaggt caggagttcg agaccagcct  18360
ggccaacatg gtgaaacctc gtctctactg aaaatacaaa aattagccgg gcgtggtggc  18420
gggcgcctgt agtcccagct acttgggagc ctgaggcagg agaatcgctt gaacctggga  18480
ggcggaggct gctgtgagcc aagatggtgc cattgcactc caccctgggt gacagagcaa  18540
gactccgtct caaaaaaaaa aaaaaagaaa gaaaaaacca agcaaatgaa aaaagaaggc  18600
aattaataat tccaaagaaa agaaaaattt gggcagaaaa gaacaaaaca agcagaattt  18660
accatgactc agttctgaat acaaacacag acatcataat gtaaacacca acactgatgc  18720
aaccagaatc atgggagaaa aaagatctag ggagggtggt ggacgggaat atcacgtatg  18780
tactgggggt aggggagaga acaaaatggg aaaaatcaag aataattcac gttagaaata  18840
aaaatacaga gcaaaattta aaaatgcaaa gaatgaggtg aagagttcaa agtggtcacc  18900
tcggggccgg gcgcggtggc tcacgcctgt gatcccagca ctctgggagg ctgaggcggg  18960
cggatcacaa ggccaggagt ttgagaccat cctggctaac aaggagaaac cccatctcta  19020
ctaaaaatta gccaggcgtg gtggtgggcg cctgtagtcc cagctactcg ggaggctgag  19080
gcaggagaat ggcgtgaacc caggaggcgc agcttgcagt gagccgagat cgcgccactg  19140
cactccagct tgggcaacag agtgagactc cgcctcaaac aaaacaaaac aaaacaaaaa  19200
aacaaagtgg tcatctctag gcaaggtggg tgggagatgg ctagggctgc aggtccacta  19260
cgtgagctgg ctcagcctat ccccagacac cctgcactca ctcagcccgg ggtcctcccc  19320
ctgcactcac tcagccccgg gtcctcccct gcactcactc agccccgggt cctccccctg  19380
cactcactca gccccgggtc ctcccctgcc tgctctttct ctgaccctgc cctccactgt  19440
tccttttctt tctttctctc cctgttgtgt ccaggaacca ggcaccaccc tcatttcttc  19500
ttgatcaatc tttaaaaacc agcagtgctc agctaactct tcatctatct cccccgacct  19560
ggggctctgc tgaatccacg ctttagaccc agctatcagc tcggcatgta cagctggatg  19620
tccacaccga gctgctcacc ctgtccccag cttcttcctc ccactgtcca ctgcagaagc  19680
ctcctaacag gacccctgct gctaccccgg accctgcaac ccattcccac acagcagcca  19740
gatgctttga cacccgaagt ctcctatgaa tccgatgagg cctctgcacc acacctcatt  19800
ttacagaagt acaggggaaa caggggtctg ttgacaccac agagatgcag ctggccaaag  19860
```

gcagaatgtg gggtacacga ctgtcaaacg ccaggggtcc ttacacgaat ggtggaaaaa 19920
gaggggcatg ttacggatgg aggctcggga cacatgggcg ccgccttccc atgctgccag 19980
caacccacca ggaacctatt a 20001

<210> SEQ ID NO 3
<211> LENGTH: 10000
<212> TYPE: DNA
<213> ORGANISM: Macaca mulatta

<400> SEQUENCE: 3
tgctcctact ccgaaccgac cgacccagcc ctctcggcgc ccgcatcctc caaggaccgg 60
ccagggctgc tttctgccct tgctattggg cgcatgaggg ttggggggtc ggggcgcacc 120
caggccggca cccaggcctg ccccgccccc acggagtgag ggctcagggc tttgtcaaca 180
gcctgtggcc cctgatcccg ccctggtgcc ctgaccttcc gctgccttct ctggtttcac 240
aaaaacatcc cggctccgat gccggagctc ctcaaagcgt ctgagaggcc ccttgcggac 300
gccctgggag ccccgctgcc ttcctgaacc agtggccgct gcacccatcc tgggggccca 360
gctccaggtc tgcgagtccc tcagccaccc ccagtgggaa ttggtggagc ctgagggagc 420
catgagcaca caagagtcac gtgttctgcc agggcagaca tgggacagga caggggggtgc 480 cagccctgca aaggggccag ggcagtggag ctcaggtggc cccaaggcct ggtggtggct 540
ggtgtggccc ggcaggcggc tgtgggaggg aggaaggggg tggtgtgcag tggaggggct 600
aggaaaggcg ggcagggcac ctcgggagac cccctcattg ggcacctcgg gaaccccccc 660
ggcattgggc acctcgggaa ccccccgcat tgggaacctc gggaaccccc cgcattgggc 720
acctcgggaa cccccccccg cattgggcac ctcgggaacc cccccccgca ttgggcacct 780
ggggaacccc ccccgcattg ggcacctcgg gaaccccccc cgcattgggc acctcgggaa 840
cccctcccct aattcttatg actccaaggc ctgagaagga gcttggtcac ctggactgtg 900
aaggccgagg gtggggtctc tggtgggtgg cccaacctac cagcagcgtc gccagcaggg 960
taataagggg cactgcggcc atggggagcc ccgggtggca cctccacagc tgggagtttc 1020
tgtccacttc ttcagtcaac agacattgat cccgggctga cgggggcccg gggttgtcag 1080
tgtctcctgt caggggagag ggctgggtga gatcatcaga ggagcctccc ttcttccctt 1140
caggctggtg tcaccttcag tgacggggca gggtccctat ttgggaagtt aaatcatcat 1200
ccccgtccca ggaccacagc ggtctcagcc ttgctctcta ggccaggctg tctcctgggt 1260
gctcagctgg aaattggccc atccccccgg cttcacccac ccctgctggg atgaggggct 1320
ggagtctccc tacccacatg ggacccaccg cccgcaggga acagaggacc cccacactcc 1380
tacacctcct gcctcactat cagagaccca gtggagaatt gccccccacc ccacctcttg 1440
tattcagagg ccctgacccc taaggatcca ggactagggg tgccctgatg gggagcccac 1500
ctgtggcctg tggatgctga gctgttaggg gaatcctcca ggatccgcag ccccactttc 1560
ccaaccttct gttgagattg ggggggacac agagagcccc actccctctt cctccccact 1620
cctgggccct gactgcttca aagaaaggcc tgggggactg ggcagcccgc ccctccctca 1680
gctcactggg gtctccagac tgcatgcacg gctggaaggt ggggccccgg cactcgagga 1740
gcttgtgtgt ggaggcgcca tctcctctcg cactggcttg gggtgctccc cagtggctct 1800
ggggtcaaca tggcagtcat tgaatggctc ctgtttctct ggcagagttg gggcagagcc 1860
aggcttggcc acgctgggct ctaaggggct gtcattttgc ccagggagct cctggctgag 1920
ctgtcctctc cccagggtga gcacgcatgc ccctaacccc cactgcaggg cccccaggca 1980

```
gggaacagct tatcagccag tgtccttcct ccttggcccc tgcctgcatc tccaccatcc   2040
gccctgctcc agctgccgtt tgtctttctc cccgtcccct gcccagagcc ccaggcctcc   2100
cctgcacccc tgagcctgcc cacctagcag tgcccctcct ccagggcccc tcctccaggg   2160
cccctcgggg ttgggggtgc acacagcagg gagaggcggc tcctgctgct cctcacccag   2220
cccagctcag tggccagagc cgcccagggc agtggcagca gatggggctg tttgatcaga   2280
atcaggaaaa ataaggcccc ttgggtgacc ccagagctgg ggacgccaaa actgctcctc   2340
ctcccccacc cgcctgctgc tttctccacc agggagagcc ccctccctac tccgtgggtc   2400
cttcgcccca gtgctaagcc tgcatggctg ctcacctggc tcagggactg ggatcagtg   2460
atgcatgggt cctgcctccc atcggcccct acctgagccc agggtccaag ggctgcggtt   2520
ggaagcccct tagcaggctg tgacgcaggt gcctgtccct atcattcagc tgtcaccctg   2580
tttggtgcat ctcaggccct gttagcagga ggagccccag gtggtgctgg ccccacgcag   2640
gctcacccag cagctgcctg gaggaggcta aaatccaggc tgtcccatgg cagccagctg   2700
tccagcccgg cccggaaatc ctccgctcca gcggcagcct tcgcccttct cctcacccct   2760
ctccccggct tcttcctggc actgccttcc agctggccgg ccctccatct gcccagccct   2820
ccatccacac ctcttattcc gtttgagggt gccccaaaga agagctcatc gcagcctggg   2880
ggctcacagc cagcacacgg gccccacggg aagaccctcc ctgcttctcc cacagaattc   2940
agttggtgca gaaactaggc tctgcagcaa tgaaaggccg atttgtggag ctgttcccgc   3000
cccaaactcc cagctcagat gctggctctg gcctgggacc aggtgctgtg actcccgcag   3060
ccctggcaga caccacaggg gctgtcctcc ccaccctgtg ccccgactct aggccagctc   3120
ctcctccgag ccggcgctgg cagtgctaat ctcaaaggaa tgtgcagcca gcctgtagtg   3180
tcccatggga cccaggaagc ccaaccgagc cttgcatggc acccatgggg cacctaggca   3240
ccacagtgct gggcaggggc atgcatgtga cacagatccc cgagtgtggg tcccacacac   3300
ttggcctggc acagctgcaa gccagcccag ccactttgct caccgtggca ctggggccaa   3360
gtgatggaag gtctgggcac cgccaccctc aggctcggca cgttggctca ggtcagcctg   3420
gcaagccaac tttcccaggg gctaagaatg ggtgaggacc ggaaccgacg gggctgtca   3480
actgagggag gaggtcagca tctggggagg ctggtcccct gccaagagca ttgggtcacc   3540
cggcaggagg gtggctgcca acagcactga gacaaggggc tctgggaccc tcagagctgc   3600
cagccagcca gcgctgggtg gcaggaaagc cagctccact tcctactggc aaggagtgac   3660
tcctgctggg gtctcctccc tcccagctcc ctcttttttt tttttttttt tttttttgag   3720
acagtctcac tctgtctgcc agtctggagt gcagtggctc cgtcttggct cattacaagc   3780
tctgcctccc gggttcacgc cattctcctg cctcagactc ccgagtaact gggactacag   3840
gcgcccacta ccatgcccgg ctaatttttt tatttttagt agagacatgg tttcaactat   3900
tttagccagg atggtctcga tctcctgacc ttgtgatctg cctgccttga cctcccaaag   3960
ttctgggatt acaggtgtga gccaccatgc ccagccccca gctccctctt tatccgtagg   4020
actctgaggc tgagaggggc agcttaaggg gagggccccc ccactggcca gggctcccca   4080
ggctctgctg ctctgccact cagctgccct cggaggagcg cgcacaccca ccaggactgc   4140
attgccccag ccgtgcagcc cctgccagat gtgggaggca gctagctgcc cagaggcatg   4200
ccccccctgtc agccacgtcg acccctgcta ctgttgctgc tgctgctggc ctgccaggtg   4260
aggactcaca gcaccctcag cacccagggg ccctcctgag gactgcacac tgatggttct   4320
```

```
ctgcctgcct gcctgcctgc ctggctgtcc gtctgcctat ctgtccatct gcctgcctgt   4380
ccatctgtct gtctgcctat ctgtctgtct gcctgcctgt ctgcctgcct gcctatctgt   4440
ccgtctgtct gtctgtctgc ctatctgtct gtctttctgc ctgtctgcct gtctgcctat   4500
ttgtctgtct gtctgcctgt ctgcctattt ctctgcctat ctgtctgcct gtctgcctat   4560
ttgtctgtct gtctgtctgc ctatttctct gcctatctgc ctgcctgtct gcctgcctgt   4620
ctgcctgtct gcctgcctgt ctgcctgcct gcctgtctgt ctgtctgtcc atctgcctgt   4680
ctgcctatct gtctgtccat ctgcctgcct gtctgtatgg ttgcttgtgc atgtgtcccc   4740
cagccacagg ccccctccgc tcaggtgatg gacttcctgt ttgagaagtg gaaactctac   4800
ggtgaccagt gtcaccacaa cctgagcctg ctgccccctc ccacgggtga gcccccaccc   4860
agagcctttc agcctgtgcc tggcctcagc atttcctgag ctcttcatgg gaaggttcct   4920
gggtgcttat gcagcccttg aggatcccgc caaggggccc caccacctca ggccccacca   4980
ccatgggcag gtgacgtaac caggtagctg agccacagag ctggggactt gcctaaggct   5040
gcagagccag gaaataacag aacagtggaa ttgctgcgtg tccccaggcc cagatgcgta   5100
ataccgccta tagccccatg gagttttcag tgggcagaca gtgccagggc gtgggaggtg   5160
ggacccagag ggtcagcaga ggacacaggc ctgggaaggc ttgggtggag agtgcatatc   5220
atggcctgga cacttggggt gcagggcgag gctagggctg gaggacttac ctgggaggca   5280
gtgccacggt tcagacgagg gaggcagcct ccactgggca gaggggaccg ggtgtggcag   5340
ccacaggttt ggcagtgcac ctgggatgga tgaaaatggc attggggttc agcccccaga   5400
gagggaggta ctgcgagaaa gtcacggaga atgggggacc ccagtgtggg tttgggggac   5460
atctgagatg gggggttctct gagtgaaggt gtcctgcaga gctggaactc agggatgggc   5520
tgggagtgct aggggaggct ggcccagggg agatggatgg tcaggtgagg aagttggagg   5580
tcagattggg gaggtggagg tcaggtgggg gaggaagcag cccaggtcat gtcctggggg   5640
gaggtgacag ctgagctcag gcctccagag agaggtaaga ggcctgctga gggagcccct   5700
tctcccaccc tgccctgcag agctggtctg taacagaacc ttcgacaagt attcctgctg   5760
gccagacacc cctgccaata ccacggccaa catctcctgc ccctggtacc tgccttggca   5820
ccacaaaggt acccatagag ggaaggaaca gtgggagggg caggcccagg ggtggcgctg   5880
accccagcct cccccaacac acgcagtgca acaccgcttc gtgttcaaga gatgcgggcc   5940
cgatggtcag tgggtgcgtg gaccccgggg gcagccttgg cgtgacgcct ctcagtgcca   6000
gatggacggc gaggagcttg aggtccaggt cagccggcgg caggcgggcg cggtggggct   6060
ggatgggaat gggcacgggg gtccccgccc ggccctcaca ggccactgta actcgcagaa   6120
ggaggtggct aagatgtaca gcagcttcca ggtgatgtac acggtgggct acagcctgtc   6180
cctgggggcc ctgctcctcg ccttggccgt cctgggggc atcaggtagg atcccgccag   6240
tgcccggggc ggccgcagag ggcagggagg agggcggtcg ctgactggct gtccccacag   6300
caagctgcac tgcacccgca acgccatcca cgcgaacctg tttgtgtcct tcgtgctgaa   6360
ggccagctcc gtgctggtca tcgatgggct gctcaggacc cgctacagcc agaagattgg   6420
cgacgacctc agtgtcagca tctggctcag tgatggagtg agccccccgt aggcggcccc   6480
acacaggcgg gtgggcgggc agccaggcag gtggccatgt ggccacgctc acactgcacc   6540
tgtgccaggc ggtggccggc tgccgtgtgg ccgcggtgtt catgcaatat ggcgtcgtgg   6600
ccaactactg ctggctgctg gtggagggcc tgtacctgca caacctgctg ggcctggcca   6660
ccctccctga gaggagcttc ttcagcctct acctgggcat cggctggggt gagtgggccg   6720
```

```
gcacgggaag gggtcggggc aggctggcca agccttgaga ccacagctgc tgccccccac   6780
aggtgccccc atgctgttca tcatcccctg ggtggtggtc aggtgtctgt tcgagaacat   6840
ccagtgagta tgagcggccg gacggcccgg ggaaggggcc ggggggctgg ggtgtggagc   6900
tctggcccga ggcagggagg ggccggggat gagcctggtg cccggggagg gtggtcattc   6960
gtgaccttct cccttcgttt cctgaggcct gaattagata ctggcaagat cgggacgggg   7020
gtgctgaggg ctgagggggcc ggggtctgtg ccccagtttg tgagtggccc ggcctcgcag   7080
gtgctggacc agcaatgaca acatgggctt ctggtggatc ctgcggttcc ccgtcttcct   7140
ggccatcctg gtgaggaaat gaagagcaag gaccgcacgc cagggccctc ctcccttggc   7200
gtcctgaggc tgccccagga ggcagcatcc tgtctgggag ggccaggagg gagctggcac   7260
ccagacagga caccaggaca ctggccagca ccctgggcac tgagccaggc tgctcctccc   7320
tggctgggtg cccaccagcc ccagggctct gtgccagggc ctatctggct gccagaccca   7380
cctgcaggag ggtcaggtgg ggccttccaa gggcacagag ctgtcccctg gggctctggg   7440
tgcccctgac tcgtgccctt ctcacataga tcaacttctt catcttcatc cgcattgttc   7500
acctgcttgt ggccaagctg cgggcgcggg agatgcacca cacagactac aagttccggt   7560
gggtgccacg gcgggccggc gcctccggat ctggagaccc tcagggccag agggcagctg   7620
ggtgggggga ctccaagctc cacgtggatg gtgcgggccg agggcgaggg tggtgtgtga   7680
ctcgggctct gcctctgtag actggccaag tccacactga ccctcatccc cctgctgggt   7740
gtccacgaag tggtcttcgc cttcgtgacg gacgagcacg cccagggcac cctgcgcttc   7800
gccaagctct tcttcgacct cttcctcagc tccttccagg tgcctgcccg cccgcggctc   7860
ccccacccgg ggcgcagcat gccacccctg accaccgtct ctctccaggg cctgctggtg   7920
gctgtcctct actgcttcct caacaaggag gtaggtggca gtgggggcgt ctgagaccat   7980
cagccctggc cgtcagggtc aggggcagag agtggcacag ggatgccagc cccacccctg   8040
ctcaggggtt ggaacacatg tggcccaagc cttttactgg gtgccgttgc cgtggcgctg   8100
gctgtcaggc ccccaagaca ggttggcctc agccccattg ctagggtgtc cacagcgggg   8160
gtccccagat gtctgcagac tgtgctttcc gtggcgatgc tgggtggcat agctgtgccc   8220
agcagggagc ttgtgtcgct ctgcacccct cagagtggag accgggcatc tctgacgggg   8280
cccacagcag gtcccggtgg ggcggagagg acaggcagac ccccaggactg gcctgcccca   8340
ccccccgccc caggtgcagt cggaacttcg gcggcattgg caccgctggc gcctgggcaa   8400
agtgctgcag gaggagcggg gcaccagcaa ccacaaggcc ccatctgcgc ctggccaagg   8460
ccttcctggc aagaagctgc agtctgggag gggtggtggc agccaggact catctgcgga   8520
gatccccttg gctggtggcc tccctaggtt ggctgagagc cccttctcaa ctctgctggg   8580
accccagcta gggctggact caggcaccta gagggcatcg ctggacaacc cagaaccaga   8640
cgcccagctg aggctggggg caggggagcc aaaagcagcc cccgcctatc ccctacccccc   8700
agtgtggcag tccgagagat ggggcctcct ctccctgcac ctgccctgtc cctggtgcgg   8760
gggcgagctg aggagtccag ggcagaggta ggggctgtgc tgcgaactgc tcaccagtgt   8820
ccccatggat gttggcacgt gctacatgcc tggagatgtc ctccaacaat aaagagctca   8880
agtggtcacc gcgcatgtcc tggaaagcag ggctggaaat gccgggccga agcagtgggg   8940
atggaacagc agtgggtggt cagcgccagt gcgggtcgtt gaaagacccc tgctgtccca   9000
gttcacagag agttggtact ggaaccccag aggatcccga aggcagccag cctgtgccca   9060
```

```
tctgagcagg ccctggccac cttcccatcc tggttctggc gggcatcccc ctggacgctt   9120

tggccaccag agggtcacca ttcaccagca gaaatgtgag gggcacagtg gctaagggag   9180

catgaggcat cacagtcccc caacccaccc catcagcact ggattcaccc agagggtgtc   9240

tcctccctgg aggccgtgag gacactggta cctggctcac cagcccaccc ttcctctgag   9300

cctcctggcc tccgcttcat ctcagctcca gccccctcgg gcaatttgca ggccacgtag   9360

cagactgaag caggaagaaa tgggcctgaa cattgccacg ggtccaggtg acgaagcagt   9420

gcaagttgcc caaactctgc acaggaccca cggcgtgcca cacagagagg tccagcctac   9480

gccagtcctc ctgccactgc atggtgggta ggtgccctgc ttgccagcca gggagcacca   9540

ggaaagagct gcctcctgca tgttggacac aggaggtgct tgagggtggg gtctcccatt   9600

gtctggggca caccctgaat ctaagggccc agggaccaca cagcaggggt ggagacaagt   9660

ccagggtgga agcccatgag gggcctgtgg tcagtcctcg ggtggtcct tatggtaggt   9720

gctgtgagac ctgctgaagt gtgtgcatgg gctggggaag gagccagcca ggtgcccctg   9780

ctctgaggag ctgctgggag gtgccgctgg accctggggg aaggggtgct cacaggcccc   9840

gcctgggcca cgtgggctgg agccgctcag gcagagccgg actaattggg gcaaatgagg   9900

ggacaggagg cctctgagga aaggtaaata gaattactca cccaccaggc actggggccc   9960

tcctgggggg gccctcaccc tgccactcac cacagggcct                        10000
```

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4

```
gcactttgtg gtgccaaggc                                                 20
```

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 5

```
gcaccccagc cgatgcc                                                    17
```

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6

```
agccctggcc ggtcctt                                                    17
```

<210> SEQ ID NO 7
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 7

```
tcccgaggtg cccaatg                                                    17
```

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 8
ttcccgaggt gcccaat 17

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gggttcccga ggtgcccaat 20

<210> SEQ ID NO 10
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 10
gttcccgagg tgcccaa 17

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 11
ggttcccgag gtgccca 17

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 12
gggttcccga ggtgccc 17

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 13
tgatctcacc cagccct 17

<210> SEQ ID NO 14
<211> LENGTH: 17
<212> TYPE: DNA
<213> ORGANISM: Artificial Sequence
<220> FEATURE:

<223> OTHER INFORMATION: Synthetic oligonucleotide

<400> SEQUENCE: 14
aaggtgacac cagcctg 17

<210> SEQ ID NO 15
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 15
ctgaaggtga caccagc 17

<210> SEQ ID NO 16
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 16
ttccagctga gcaccca 17

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tccacaggcc acaggtgggc 20

<210> SEQ ID NO 18
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 18
gcatccacag gccacag 17

<210> SEQ ID NO 19
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 19
agcatccaca ggccaca 17

<210> SEQ ID NO 20
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 20
cagcatccac aggccac 17

<210> SEQ ID NO 21
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 21
ctcagcatcc acaggcc 17

<210> SEQ ID NO 22
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 22
agccactggg agcaccc 17

<210> SEQ ID NO 23
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 23
ggctctgccc caactct 17

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gtgagcagcc atgcaggctt 20

<210> SEQ ID NO 25
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 25
gagcagccat gcaggct 17

<210> SEQ ID NO 26
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 26
tgagcagcca tgcaggc 17

<210> SEQ ID NO 27
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 27
gccaggtgag cagccat 17

<210> SEQ ID NO 28
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 28
agggacaggc acctgcg 17

<210> SEQ ID NO 29
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 29
gcctggattt tagcctc 17

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
cggggtggca acagctacac 20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
gcaaggctcg gttgggcttc 20

<210> SEQ ID NO 32
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 32
tgcaaggctc ggttggg 17

<210> SEQ ID NO 33
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 33
gcagagcagc agagcct 17

<210> SEQ ID NO 34
<211> LENGTH: 17

<212> TYPE: DNA
<213> ORGANISM: Artificial Sequence
<220> FEATURE:
<223> OTHER INFORMATION: Synthetic oligonucleotide

<400> SEQUENCE: 34
ggcagagcag cagagcc 17

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
ggcagctgag tggcagagca 20

<210> SEQ ID NO 36
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 36
gcatgcctct gggcagc 17

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
aggcacaggc tgaaaggctc 20

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 38
aggccaggca caggctg 17

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gctgaggcca ggcacaggct 20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
ggctgcataa gcacccagga 20

<210> SEQ ID NO 41
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 41
ctgcataagc acccagg 17

<210> SEQ ID NO 42
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 42
cccagctctg tggctca 17

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gtccccagct ctgtggctca 20

<210> SEQ ID NO 44
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 44
gcaagtcccc agctctg 17

<210> SEQ ID NO 45
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 45
cgccctggca ctgtctg 17

<210> SEQ ID NO 46
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 46
gtgtccaggc catgata 17

<210> SEQ ID NO 47
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 47
aagtgtccag gccatga 17

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
cccaagtgtc caggccatga 20

<210> SEQ ID NO 49
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 49
caagtgtcca ggccatg 17

<210> SEQ ID NO 50
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 50
ccaagtgtcc aggccat 17

<210> SEQ ID NO 51
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 51
cccaagtgtc caggcca 17

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
caccccaagt gtccaggcca 20

<210> SEQ ID NO 53
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 53
ccccaagtgt ccaggcc 17

<210> SEQ ID NO 54
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 54
accccaagtg tccaggc 17

<210> SEQ ID NO 55
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 55
gcaccccaag tgtccag 17

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ccctgcaccc caagtgtcca 20

<210> SEQ ID NO 57
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 57
aaacctgtgg ctgccac 17

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
gccaaacctg tggctgccac 20

<210> SEQ ID NO 59
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 59
ggacaggctg tagccca 17

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
ggctcactcc atcactgagc 20

<210> SEQ ID NO 61
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 61
ccacctgcct ggctgcc 17

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
gtgcaggtac aggccctcca 20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ggagggtggc caggcccagc 20

<210> SEQ ID NO 64
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 64
ccagccgatg cccaggt 17

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
ggccagtgtc ctggtgtcct 20

<210> SEQ ID NO 66
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 66
gccaccagca ggccctg 17

<210> SEQ ID NO 67

<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 67
gggctgaggc caacctg 17

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
gccacccagc atcgccacgg 20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
ccctgctggg cacagctatg 20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cacaagctcc ctgctgggca 20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
gagcgacaca agctccctgc 20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
ggtgcagagc gacacaagct 20

<210> SEQ ID NO 73
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 73
ggctgccacc acccctc 17

<210> SEQ ID NO 74
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 74
ctttattgtt ggaggac 17

<210> SEQ ID NO 75
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 75
ctctttattg ttggagg 17

<210> SEQ ID NO 76
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 76
gctctttatt gttggag 17

<210> SEQ ID NO 77
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 77
agctctttat tgttgga 17

<210> SEQ ID NO 78
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 78
gagctcttta ttgttgg 17

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
acctggaagc tgctgtacat 20

<210> SEQ ID NO 80
<211> LENGTH: 17
<212> TYPE: DNA

<213> ORGANISM: Artificial Sequence
<220> FEATURE:
<223> OTHER INFORMATION: Synthetic oligonucleotide

<400> SEQUENCE: 80
gggcaatgca gtcctgg 17

<210> SEQ ID NO 81
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 81
gaaggtgaca ccagcct 17

<210> SEQ ID NO 82
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 82
gctcagcatc cacaggc 17

<210> SEQ ID NO 83
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 83
tggattttag cctcctc 17

<210> SEQ ID NO 84
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 84
gccaaacctg tggctgc 17

<210> SEQ ID NO 85
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 85
gggttcccga ggtgcccaat g 21

<210> SEQ ID NO 86
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 86
ggttcccgag gtgccc 16

<210> SEQ ID NO 87
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 87
gggttcccga ggtgcc 16

<210> SEQ ID NO 88
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 88
gaggccaggc acaggct 17

<210> SEQ ID NO 89
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 89
cggtccttgg aggatgc 17

<210> SEQ ID NO 90
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 90
gttcccgagg tgcccaatg 19

<210> SEQ ID NO 91
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 91
ggttcccgag gtgcccaat 19

<210> SEQ ID NO 92
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 92
gggttcccga ggtgcccaa 19

<210> SEQ ID NO 93
<211> LENGTH: 18
<212> TYPE: DNA
<213> ORGANISM: Artificial Sequence
<220> FEATURE:

<223> OTHER INFORMATION: Synthetic oligonucleotide

<400> SEQUENCE: 93
ggttcccgag gtgcccaa 18

<210> SEQ ID NO 94
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 94
gttcccgagg tgccca 16

<210> SEQ ID NO 95
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 95
gggttcccga ggtgccca 18

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 96
gggttcccga ggtgcccaat a 21

<210> SEQ ID NO 97
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 97
ccagctctgt ggctcag 17

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
cctggatttt agcctcctcc 20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
tgggtctctg atagtgaggc 20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
gctcagcatc cacaggccac 20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gccaagcctg gctctgcccc 20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
ctctttattg ttggaggaca 20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
tctttattgt tggaggacat 20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
ccacaggcca caggtgggct 20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
agccaggtga gcagccatgc 20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
aagtgtccag gccatgatat 20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
ccaagtgtcc aggccatgat 20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
accccaagtg tccaggccat 20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
gcaccccaag tgtccaggcc 20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
tgcaccccaa gtgtccaggc 20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
gcacatggga cgtgccgaca 20

<210> SEQ ID NO 112
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 112
gctctttatt gttggaggac 20

<210> SEQ ID NO 113
<211> LENGTH: 20

<212> TYPE: DNA
<213> ORGANISM: Artificial Sequence
<220> FEATURE:
<223> OTHER INFORMATION: Synthetic oligonucleotide

<400> SEQUENCE: 113
gagctcttta ttgttggagg 20

<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 114
agctctttat tgttggagga 20

<210> SEQ ID NO 115
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 115
ggttcccgag gtgcccaatg 20

<210> SEQ ID NO 116
<211> LENGTH: 18
<212> TYPE: DNA
<213> ORGANISM: Artificial Sequence
<220> FEATURE:
<223> OTHER INFORMATION: Primer

<400> SEQUENCE: 116
gacacccccg ccaatacc 18

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
ccgcatctct tgaacacgaa 20

<210> SEQ ID NO 118
<211> LENGTH: 15
<212> TYPE: DNA
<213> ORGANISM: Artificial Sequence
<220> FEATURE:
<223> OTHER INFORMATION: Probe

<400> SEQUENCE: 118
ttggcaccac aaagt 15

<210> SEQ ID NO 119
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 119

-continued

```
gcgtttgctc ttcttcttgc gtttttt                                          27


<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120

atctcctgcc cctggtacct                                                  20


<210> SEQ ID NO 121
<211> LENGTH: 18
<212> TYPE: DNA
<213> ORGANISM: Artificial Sequence
<220> FEATURE:
<223> OTHER INFORMATION: Primer

<400> SEQUENCE: 121

ggtccacgca cccactga                                                    18


<210> SEQ ID NO 122
<211> LENGTH: 24
<212> TYPE: DNA
<213> ORGANISM: Artificial Sequence
<220> FEATURE:
<223> OTHER INFORMATION: Probe

<400> SEQUENCE: 122

accgcttcgt gttcaagaga tgcg                                             24
```

ANTISENSE MODULATION OF GCGR EXPRESSION

RELATED APPLICATIONS

This application is claims priority under 35 U.S.C. 119(e) to U.S. Provisional Patent Application No. 61/537,007, filed Sep. 20, 2011, the contents of which is herein incorporated in its entirety.

SEQUENCE LISTING

The present application is being filed along with a Sequence Listing in electronic format. The Sequence Listing is provided as a file entitled BIOL0161USSEQ.txt created Sep. 19, 2012, which is 60 Kb in size. The information in the electronic format of the sequence listing is incorporated herein by reference in its entirety.

FIELD

Provided herein are methods, compounds, and compositions for reducing expression of GCGR mRNA and protein in an animal. Such methods, compounds, and compositions are useful, for example, to treat, prevent, delay or ameliorate diseases associated with metabolic disorders, particularly disorders associated with diabetes.

BACKGROUND

Insulin and glucagon are two pancreatic hormones involved in regulating glucose homeostasis and metabolism. Glucagon is secreted from the α-cells of the pancreatic islets and regulates glucose homeostasis through modulation of hepatic glucose production (Quesada et al., J. Endocrinol. 2008. 199: 5-19). The main function of glucagon is to counteract the actions of insulin.

Dysregulation of glucose metabolism may be caused either by defective insulin secretion and/or action, or by impaired postprandial glucagon suppression (Shah et al., Am. J. Physiol. Endocrinol. Metab. 1999. 277: E283-E290) Inhibition of postprandial glucagon secretion in diabetic subjects has been shown to substantially reduce blood glucose, suggesting that glucagon contributes significantly to the hyperglycemia seen in subjects with type 2 diabetes mellitus (Shah et al., J. Clin. Endocrinol. Metab. 2000. 85: 4053-4059).

Type 2 diabetes is characterized by impaired insulin secretion and/or action, and many subjects also exhibit inappropriate levels of circulating glucagon in the fasting and postprandial state. An increase in the glucagon/insulin ratio is likely an important determinant of the hyperglycemia seen in type 2 diabetes patients (Baron et al., Diabetes. 1987. 36: 274-283). Lack of suppression of postprandial glucagon secretion in subjects with T2DM also plays an important role in the pathogenesis of postprandial hyperglycemia (Henkel et al., Metabolism. 2005. 54: 1168-1173).

Glucagon exerts its action on target tissues via the activation of its receptor, GCGR. The glucagon receptor is a 62 kDa protein that is a member of the class B G-protein coupled family of receptors (Brubaker et al., Recept. Channels. 2002. 8: 179-88). GCGR activation leads to signal transduction by G proteins ($G_s\alpha$ and $G_q$), whereby $G_s\alpha$ activates adenylate cyclase, which causes cAMP production, resulting in an increase in levels of protein kinase A. GCGR signaling in the liver results in increased hepatic glucose production by induction of glycogenolysis and gluconeogenesis along with inhibition of glycogenesis (Jiang and Zhang. Am. J. Physiol. Endocrinol. Metab. 2003. 284: E671-E678). GCGR is also expressed in extrahepatic tissues, which includes heart, intestinal smooth muscle, kidney, brain, and adipose tissue (Hansen et al., Peptides. 1995. 16: 1163-1166).

Antisense inhibition of GCGR provides a unique advantage over traditional small molecule inhibitors in that antisense inhibitors do not rely on competitive binding of the compound to the protein and inhibit activity directly by reducing the expression of GCGR. A representative United States patent that teaches GCGR antisense inhibitors includes U.S. Pat. No. 7,750,142, of which is herein incorporated by reference in its entirety. Antisense technology is emerging as an effective means for reducing the expression of certain gene products and may therefore prove to be uniquely useful in a number of therapeutic, diagnostic, and research applications for the modulation of GCGR.

There is a currently a lack of acceptable options for treating metabolic disorders. It is therefore an object herein to provide compounds and methods for the treatment of such diseases and disorder. This invention relates to the discovery of novel, highly potent inhibitors of GCGR gene expression.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY

Provided herein are methods, compounds, and compositions for modulating expression of GCGR and treating, preventing, delaying or ameliorating diseases associated with metabolic disorders, particularly disorders associated with diabetes and/or a symptom thereof.

DETAILED DESCRIPTION

It is to be understood that both the foregoing general description and the following detailed description are exemplary and explanatory only and are not restrictive described herein, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all documents, or portions of documents, cited in this application, including, but not limited to, all patents, applications, published applications and other journal publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to GCGR is an active pharmaceutical agent.

"Active target region" or "target region" means a region to which one or more active antisense compounds is targeted. "Active antisense compounds" means antisense compounds that reduce target nucleic acid levels or protein levels.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or inflammatory obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound provided herein. For example, a first agent can be an antisense oligonucleotide targeting GCGR. "Second agent" means a second therapeutic compound described herein (e.g. a second antisense oligonucleotide targeting GCGR) and/or a non-GCGR therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Complementarity" means the capacity for pairing between nucleobases of a first nucleic acid and a second nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucagon receptor" or "GCGR" means any nucleic acid or protein of GCGR.

"GCGR expression" means the level of mRNA transcribed from the gene encoding GCGR or the level of protein translated from the mRNA. GCGR expression can be determined by art known methods such as a Northern or Western blot.

"GCGR nucleic acid" means any nucleic acid encoding GCGR. For example, in certain embodiments, a GCGR nucleic acid includes a DNA sequence encoding GCGR, a RNA sequence transcribed from DNA encoding GCGR (including genomic DNA comprising introns and exons), and a mRNA sequence encoding GCGR. "GCGR mRNA" means a mRNA encoding a GCGR protein.

"Glucose" is a monosaccharide used by cells as a source of energy and inflammatory intermediate. "Plasma glucose" refers to glucose present in the plasma.

"Hybridization" means the annealing of complementary nucleic acid molecules. In certain embodiments, complementary nucleic acid molecules include an antisense compound and a target nucleic acid.

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting an animal with metabolic" means identifying or selecting a subject having been diagnosed with a metabolic disease, or a metabolic disorder; or, identifying or selecting a subject having any symptom of a metabolic disease, including, but not limited to, metabolic syndrome, hyperglycemia, hypertriglyceridemia, hypertension increased insulin resistance, decreased insulin sensitivity, above normal body weight, and/or above normal body fat or any combination thereof. Such identification may be accomplished by any method, including but not limited to, standard clinical tests or assessments, such as measuring serum or circulating (plasma) blood-glucose, measuring serum or circulating (plasma) triglycerides, measuring blood-pressure, measuring body fat, measuring body weight, and the like.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering therapy" or "lipid lowering agent" means a therapeutic regimen provided to a subject to reduce one or more lipids in a subject. In certain embodiments, a lipid-lowering therapy is provided to reduce one or more of ApoB, total cholesterol, LDL-C, VLDL-C, IDL-C, non-HDL-C, triglycerides, small dense LDL particles, and Lp(a) in a subject. Examples of lipid-lowering therapy include statins, fibrates, and MTP inhibitors.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disease" or "metabolic disorder" refers to a condition characterized by an alteration or disturbance in metabolic function. "Metabolic" and "metabolism" are terms well known in the art and generally include the whole range of biochemical processes that occur within a living organism. Metabolic diseases or disorders include, but are not limited to, obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and the metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines "Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to GCGR is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" or "TG" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to an animal to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting GCGR expression.

Certain embodiments provide antisense compounds targeted to a GCGR nucleic acid. In certain embodiments, the GCGR nucleic acid is any of the sequences set forth in GENBANK Accession No. NM_000160.3 (incorporated herein as SEQ ID NO: 1) or GENBANK Accession No:

NW_926918.1 truncated from nucleotides 16865000 to 16885000 (incorporated herein as SEQ ID NO: 2). In certain embodiments, GCGR has the rhesus monkey sequence as set forth in SEQ ID NO: 3.

In certain embodiments, the compounds or compositions provided herein comprise a modified oligonucleotide consisting of 12 to 30 nucleosides having a nucleobase sequence complementary to an equal length portion of any of SEQ ID NOs: 1-3.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-115.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 11, 17, 31, 80, or 85.

In certain embodiments, the compound or composition provided herein is or comprises ISIS NOs: 449884, 459014, 398471, 448766, or 459157.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compound or composition is or comprises ISIS NO: 449884.

In certain embodiments, the compound or composition is or comprises ISIS NO: 459014.

In certain embodiments, the compounds or compositions provided herein comprise a modified oligonucleotide consisting of 15 to 30 nucleosides having a nucleobase sequence complementary to an equal length portion of any of SEQ ID NOs: 1-3.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-115.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 11, 17, 31, 80, or 85.

In certain embodiments, the compound or composition provided herein is or comprises ISIS NOs: 449884, 459014, 398471, 448766, or 459157.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compound or composition provided herein is or comprise ISIS NO: 449884.

In certain embodiments, the compound or composition provided herein is or comprise ISIS NO: 459014.

In certain embodiments, the compounds or compositions provided herein comprise a modified oligonucleotide consisting of 16 to 21 nucleosides having a nucleobase sequence complementary to an equal length portion of any of SEQ ID NOs: 1-3

In certain embodiments, the compounds or compositions provided herein comprise a modified oligonucleotide consisting of 16 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 4-115.

In certain embodiments, the compounds or compositions provided herein comprise a modified oligonucleotide consisting of 16 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 11, 17, 31, 80, or 85.

In certain embodiments, the compounds or compositions provided herein comprise a modified oligonucleotide consisting of 16 to 21 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 16 to 21 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 17 to 35 nucleosides having a nucleobase sequence complementary to an equal length portion of any of SEQ ID NOs: 1-3.

In certain embodiments, the compounds or compositions provided herein comprise a modified oligonucleotide consisting of 17 to 35 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 20 to 35 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein can consist of 17 to 35 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein can consist of 17 to 35 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 17 to 30 nucleosides having a nucleobase sequence complementary to an equal length portion of any of SEQ ID NOs: 1-3.

In certain embodiments, the compounds or compositions provided herein comprise a modified oligonucleotide consisting of 17 to 30 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 17 to 30 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein comprise a modified oligonucleotide consisting of 17 to 30 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 17 to 30 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 17 to 25 nucleosides having a nucleobase sequence complementary to an equal length portion of any of SEQ ID NOs: 1-3

In certain embodiments, the compounds or compositions provided herein comprise a modified oligonucleotide consisting of 17 to 25 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 17 to 25 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein comprise a modified oligonucleotide consisting of 17 to 25 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 17 to 25 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions described herein comprise a modified oligonucleotide consisting of 17 to 24 nucleosides having a nucleobase sequence complementary to an equal length portion of any of SEQ ID NOs: 1-3.

In certain embodiments, the compounds or compositions provided herein comprise a modified oligonucleotide consisting of 17 to 24 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 17 to 24 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein comprise a modified oligonucleotide consisting of 17 to 24 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 17 to 24 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 17 to 23 nucleosides having a nucleobase sequence complementary to an equal length portion of any of SEQ ID NOs: 1-3.

In certain embodiments, the compounds or compositions provided herein comprise a modified oligonucleotide consisting of 17 to 23 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 17 to 23 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein comprise a modified oligonucleotide consisting of 17 to 23 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 17 to 23 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 17 to 22 nucleosides having a nucleobase sequence complementary to an equal length portion of any of SEQ ID NOs: 1-3.

In certain embodiments, the compounds or compositions provided herein comprise a modified oligonucleotide consisting of 17 to 22 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 17 to 22 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein comprise a modified oligonucleotide consisting of 17 to 22 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 17 to 22 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 17 to 21 nucleosides having a nucleobase sequence complementary to an equal length portion of any of SEQ ID NOs: 1-3.

In certain embodiments, the compounds or compositions provided herein comprise a modified oligonucleotide consisting of 17 to 21 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 17 to 21 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein comprise a modified oligonucleotide consisting of 17 to 21 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 17 to 21 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 20 nucleosides having a nucleobase sequence complementary to an equal length portion of any of SEQ ID NOs: 1-3.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NOs: 4-115.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NOs: 11, 17, 31, 80, or 85.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NO: 11.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NO: 80

In certain embodiments, the compounds or compositions provided herein comprise a modified oligonucleotide consisting of 17 nucleosides having a nucleobase sequence complementary to an equal length portion of any of SEQ ID NOs: 1-3.

In certain embodiments, the compounds or compositions provided herein comprise a modified oligonucleotide consisting of 17 linked nucleosides and have a nucleobase sequence comprising at least 8, 9, 10, 11, 12, 13, 14, 15, 16, or 17, contiguous nucleobases of SEQ ID NOs: 4-115.

In certain embodiments, the compounds or compositions provided herein comprise a modified oligonucleotide consisting of 17 linked nucleosides and have a nucleobase sequence comprising at least 8, 9, 10, 11, 12, 13, 14, 15, 16, or 17 contiguous nucleobases of SEQ ID NOs: 11, 17, 31, 80, or 85.

In certain embodiments, the compounds or compositions provided herein comprise a modified oligonucleotide consisting of 17 linked nucleosides and have a nucleobase sequence comprising at least 8, 9, 10, 11, 12, 13, 14, 15, 16, or 17 contiguous nucleobases of SEQ ID NO: 11.

In certain embodiments, the compounds or compositions provided herein comprise a modified oligonucleotide consisting of 17 linked nucleosides and have a nucleobase sequence comprising at least 8, 9, 10, 11, 12, 13, 14, 15, 16, or 17 contiguous nucleobases of SEQ ID NO: 80

In certain embodiments, the compounds or compositions provided herein comprise a salt of the modified oligonucleotide.

In certain embodiments, the compounds or compositions provided herein further comprise a pharmaceutically acceptable carrier or diluent.

In certain embodiments, the nucleobase sequence of the modified oligonucleotide is at least 70%, 75%, 80%, 85%, 90%, 95%, 96%, 97%, 98%, 99% or 100% complementary to any one of SEQ ID NOs: 1-3 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NOs: 4-115 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NOs: 11, 17, 31, 80, or 85 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to SEQ ID NO: 11 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to SEQ ID NO: 80 as measured over the entirety of the modified oligonucleotide.

In certain embodiments, antisense compounds or modified oligonucleotides targets a region of a GCGR nucleic acid. In certain embodiments, such compounds or oligonucleotides targeted to a region of a GCGR nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 2: 6691-6707, 7267-7280, 7267-7283, 7267-7284, 7267-7285, 7267-7286, 7267-7287, 7267-7457, 7268-7284, 7268-7285, 7268-7286, 7268-7287, 7269-7285, 7269-7286, 7269-7287, 7270-7285, 7270-7286, 7270-7287, 7271-7287, 7291-7312, 7292-7308, 7292-7309, 7292-7310, 7292-7311, 7292-7312, 7293-7309, 7293-7310, 7293-7311, 7293-7312, 7294-7310, 7294-7311, 7294-7312, 7295-7310, 7295-7311, 7295-7312, 7296-7312, 7316-7332, 7316-7333, 7316-7334, 7316-7335, 7316-7336, 7317-7333, 7317-7334, 7317-7335, 7317-7336, 7318-7334, 7318-7335, 7318-7336, 7319-7334, 7319-7335, 7319-7336, 7320-7336, 7339-7405, 7339-7406, 7339-7407, 7339-7408, 7339-7409, 7341-7354, 7341-7357, 7341-7358, 7341-7359, 7341-7360, 7341-7361, 7342-7358, 7342-7359, 7342-7360, 7342-7361, 7343-7359, 7343-7360, 7343-7361, 7344-7360, 7344-7361, 7345-7361, 7347-7456, 7365-7381, 7365-7382, 7365-7383, 7365-7384, 7365-7385, 7366-7382, 7366-7383, 7366-7384, 7366-7385, 7367-7383, 7367-7384, 7367-7385, 7368-7383, 7368-7384, 7368-7385, 7369-7385, 7388-7382, 7389-7407, 7389-7408, 7389-7409, 7390-7406, 7390-7407, 7390-7408, 7390-7409, 7391-7407, 7391-7408, 7391-7409, 7392-7407, 7392-7408, 7392-7409, 7393-7409, 7413-7433, 7414-7430, 7414-7431, 7414-7432, 7414-7433, 7415-7431, 7415-7432, 7415-7433, 7416-7432, 7416-7433, 7417-7433, 7437-7453, 7437-7454, 7437-7455, 7437-7456, 7437-7457, 7438-7454, 7438-7455, 7438-7456, 7438-7457, 7439-7455, 7439-7456, 7439-7457, 7440-7455, 7440-7456, 7440-7457, 7441-7457, 7740-7756, 7782-7798, 7782-7801, 7782-7913, 7783-7799, 7785-7801, 7785-7913, 7897-7913, 8030-8049, 8132-8151, 8133-8152, 8133-8155, 8133-8156, 8133-8157, 8133-8159, 8139-8155, 8139-8156, 8139-8157, 8139-8159, 8140-8156, 8140-8157, 8140-8159, 8141-8157, 8141-8159, 8141-8160, 8143-8159, 8144-8160, 8386-8402, 8448-8464, 8454-8473, 9002-9019, 9002-9020, 9002-9021, 9002-9026, 9003-9019, 9003-9020, 9003-9021, 9003-9026, 9004-9020, 9004-9021, 9004-9026, 9008-9027, 9010-9026, 9130-9146, 9245-9264, 9246-9262, 9249-9265, 9592-9611, 9804-9823, 9808-9824, 10667-10683, 10667-10684, 10667-10695, 10668-10684, 10668-10695, 10676-10683, 10676-10684, 10676-10695, 10718-10734, 10772-10788, 11667-11686, 11667-11691, 11667-11695, 11675-11691, 11675-11695, 11676-11695, 11724-11741, 11724-11743, 11725-11741, 11725-11743, 11818-11834, 11819-11835, 11819-11838, 11819-11842, 11826-11842, 11962-11978, 12025-12044, 12025-12046, 12025-12049, 12025-12051, 12025-12052, 12026-12042, 12026-12044, 12026-12046, 12026-12047, 12026-12048, 12026-12049, 12026-12050, 12026-12051, 12026-12055, 12027-12046, 12027-12049, 12027-12051, 12027-12052, 12028-12044, 12028-12046, 12028-12047, 12028-12048, 12028-12049, 12028-12050, 12028-12051, 12028-12055, 12029-12045, 12029-12046, 12029-12047, 12029-12048, 12029-12049, 12029-12050, 12029-12051, 12029-12055, 12030-12046, 12030-12047, 12030-12048, 12030-12049, 12030-12050, 12030-12051, 12030-12055, 12031-12045, 12031-12048, 12031-12049, 12031-12050, 12031-12051, 12031-12055, 12032-12048, 12032-12049, 12032-12050, 12032-12051, 12032-12052, 12032-12055, 12033-12049, 12033-12050, 12033-12051, 12033-12052, 12033-12055, 12035-12051, 12035-12055, 12036-12055, 12175-12091, 12175-12094, 12178-12194, 13003-13022, 13034-13050, 13303-13022, 13314-13333, 13366-13382, 13490-13509, 13515-13534, 14138-14157, 14779-14795, 15007-15023, 15075-15094, 15075-15113, 15075-15121, 15075-15127, 15075-15133, 15094-15113, 15094-15121, 15094-15127, 15094-15133, 15102-15121, 15102-15127, 15102-15133, 15108-15127, 15108-15133, 15114-15133, 15374-15390, 15716-15735, 15742-15761, 15742-15762, 15743-15762, 15744-15760, 15744-15762, 15744-15763, 15744-15764, 15744-15765, 15745-15764, 15745-15765, 15746-15760, 15746-15762, 15746-15763, 15746-15764, 15746-15765, 15747-15763, 15747-15764, 15747-15765, 15748-15764, 15748-15765, and 15749-15765.

In certain embodiments, antisense compounds or modified oligonucleotides target a region of a GCGR nucleic acid. In certain embodiments, such compounds or oligonucleotides targeted to a region of a GCGR nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 2: 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, and 15743-15762.

In certain embodiments, antisense compounds or modified oligonucleotides targets a region of a GCGR nucleic acid. In certain embodiments, such compounds or oligonucleotides targeted to a region of a GCGR nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 2: 7270-7286, 7295-7311, 7319-7335, 7344-7360, 7368-7384, 7392-7408, 7416-7432, 7440-7456 and 10716-10734.

In certain embodiments, the following antisense compounds target a region of SEQ ID NO: 2, a nucleic acid encoding human GCGR and demonstrate at least 70% inhibition of a GCGR gene sequence: ISIS NOs: 325568, 310457, 449823, 450035, 449881, 449882, 398457, 449883, 449884, 449885, 450039, 449894, 449895, 450040, 398471, 449905, 449906, 449907, 449908, 449910, 449912, 398486, 449916, 449917, 449922, 450049, 450050, 448762, 448766, 450054, 449759, 449760, 436034, 450059, 448799, 449938, 448802, 398585, 449944, 449945, 448806, 450061, 449948, 449949, 449951, 398504, 449952, 449953, 449954, 448817, 449955, 449956, 449958, 448818, 449960, 448819, 449797, 448840, 449967, 448848, 448850, 449819, 448860, 449836, 450074, 448890, 448897, 448901, 448903, 448905, 449851, 449856, 449858, 449859, 449860, 449861, 315163, 459032, 459046, 459076, 459157, 459010, 459011, 459058, 459088, 459087, 459086, 459083, 459082, 459158, 448754, 448718, 448730, 448738, 436140, 398455, 398470, 398491, 398501, 398503, 398506, 398507, 398508, 304535, 304538, 304539, 436141, and 436164.

In certain embodiments, the following antisense compounds target a region of SEQ ID NO: 2, a nucleic acid encoding human GCGR and demonstrate at least 75% inhibition of a GCGR gene sequence: ISIS NOs: 325568, 310457, 449823, 450035, 449881, 449882, 398457, 449883, 449884, 449885, 450039, 449894, 449895, 450040, 398471, 449905, 449906, 449907, 449908, 449910, 449912, 398486, 449916, 449917, 449922, 450049, 450050, 448762, 448766, 450054, 449759, 449760, 450059, 448799, 449938, 448802, 398585, 449944, 449945, 448806, 450061, 449948, 449949, 449951, 398504, 449952, 449953, 449954, 448817, 449955, 449956, 449958, 448818, 449960, 448819, 449797, 448840, 449967, 448848, 448850, 449819, 448860, 449836, 450074, 448890, 448897, 448901, 448903, 448905, 449851, 449856, 449858, 449859, 449860, 449861, 459032, 459076, 459157, 459010, 459011, 459058, 459088, 459087, 459086, 459083, 459082, 459158, 448754, 448718, 448738, 436140, 398455, 398470, 398491, 398501, 398503, 398506, 398507, 398508, 304535, 304538, 304539, 436141, and 436164.

In certain embodiments, the following antisense compounds target a region of SEQ ID NO: 2, a nucleic acid encoding human GCGR and demonstrate at least 80% inhibition of a GCGR gene sequence: ISIS NOs: 310457, 449823, 450035, 449881, 449882, 398457, 449883, 449884, 449885, 450039, 449894, 449895, 450040, 398471, 449905, 449906, 449907, 449908, 449910, 449912, 398486, 449916, 449917, 449922, 450049, 450050, 448762, 448766, 450054, 449759, 449760, 450059, 448799, 449938, 448802, 398585, 449944, 449945, 448806, 450061, 449948, 449949, 449951, 398504, 449952, 449953, 449954, 448817, 449955, 449956, 449958, 448818, 449960, 448819, 449797, 448840, 449967, 448848, 448850, 449819, 449836, 450074, 448890, 448897, 448901, 448903, 448905, 449851, 449856, 449858, 449859, 449860, 449861, 459032, 459076, 459157, 459010, 459011, 459088, 459087, 459086, 459083, 459082, 459158, 448718, 436140, 398455, 398470, 398491, 398501, 398503, 398506, 398507, 398508, 304535, 304538, 304539, 436141, and 436164.

In certain embodiments, the following antisense compounds target a region of SEQ ID NO: 2, a nucleic acid encoding human GCGR and demonstrate at least 85% inhibition of a GCGR gene sequence: ISIS NOs: 310457, 449823, 449881, 449882, 398457, 449883, 449884, 449885, 450039, 449894, 449895, 449905, 449906, 449907, 449910, 398486, 449916, 449917, 449922, 450049, 448766, 449760, 450059, 449938, 448802, 398585, 449945, 448806, 450061, 449948, 449949, 449951, 398504, 449952, 449953, 449954, 448817, 449955, 449956, 449958, 449960, 448819, 449967, 448848, 449836, 450074, 448890, 448903, 449851, 449856, 449858, 449859, 449860, 459157, 459010, 459011, 459088, 459087, 459086, 459083, 459082, 459158, 436140, 398455, 398470, 398503, 398506, 398507, 398508, 304535, 304538, 304539, 436141, and 436164.

In certain embodiments, the following antisense compounds target a region of SEQ ID NO: 2, a nucleic acid encoding human GCGR and demonstrate at least 90% inhibition of a GCGR gene sequence: ISIS NOs: 449823, 398457, 449883, 449884, 449885, 449894, 449895, 449906, 398486, 449917, 449938, 449945, 448806, 450061, 449951, 398504, 449952, 449953, 449954, 448817, 449955, 449958, 449960, 448819, 448848, 450074, 449859, 459157, 459010, 459087, 459086, 459083, 459082, 459158, 436140, 398503, 398507, 304535, 304538, 304539, 436141, and 436164.

In certain embodiments, the following antisense compounds target a region of SEQ ID NO: 2, a nucleic acid encoding human GCGR and demonstrate at least 90% inhibition of a GCGR gene sequence: ISIS NOs: 398457, 449883, 398486, 448806, 448817, 448819, 459010, 459087, 459086, 398507, 304535, and 304538.

In certain embodiments, the following antisense compounds target a region of SEQ ID NO: 2, a nucleic acid encoding human GCGR and demonstrate an $IC_{50}$ value of less than 3 μM: ISIS NOs: 304535, 304538, 304539, 398455, 398457, 398470, 398471, 398486, 398491, 398501, 398503, 398504, 398506, 398507, 398508, 398585, 436034, 436140, 436141, 436164, 448718, 448730, 448738, 448754, 448762, 448766, 448799, 448802, 448806, 448817, 448818, 448819, 448840, 448848, 448850, 448860, 448890, 448897, 448901, 448903, 448905, 449884, 459009, 459010, 459011, 459014, 459024, 459032, 459040, 459046, 459058, 459063, 459076, 459082, 459083, 459086, 459087, 459088, 459157, and 459158.

In certain embodiments, the following antisense compounds target a region of SEQ ID NO: 2, a nucleic acid encoding human GCGR and demonstrate an $IC_{50}$ value of less than 1 μM: ISIS NOs: 304535, 304538, 304539, 398455, 398457, 398470, 398471, 398486, 398491, 398501, 398503, 398504, 398506, 398507, 398508, 398585, 436034, 436140, 436141, 436164, 448718, 448730, 448738, 448754, 448762, 448766, 448799, 448802, 448806, 448817, 448818, 448819, 448840, 448848, 448850, 448860, 448890, 448897, 448901, 448903, 448905, 449884, 459009, 459010, 459011, 459024, 459032, 459040, 459046, 459058, 459063, 459076, 459082, 459083, 459086, 459087, 459088, 459157, and 459158.

In certain embodiments, the following antisense compounds target a region of SEQ ID NO: 2, a nucleic acid encoding human GCGR and demonstrate an $IC_{50}$ value of less than 0.5 μM: ISIS NOs: 304535, 304538, 304539, 398455, 398457, 398470, 398471, 398486, 398491, 398501, 398503, 398504, 398506, 398507, 398508, 398585, 436034, 436140, 436141, 436164, 448718, 448730, 448738, 448754, 448762, 448799, 448802, 448806, 448817, 448818, 448819, 448840, 448848, 448850, 448860, 448890, 448897, 448901, 448903, 448905, 449884, 459009, 459010, 459011, 459024, 459040, 459046, 459058, 459063, 459076, 459082, 459083, 459086, 459087, 459088, 459157, and 459158.

In certain embodiments, the following antisense compounds target a region of SEQ ID NO: 2, a nucleic acid encoding human GCGR and demonstrate an $IC_{50}$ value of less than 0.3 μM: ISIS NOs: 304535, 304538, 398455, 398457, 398470, 398471, 398486, 398504, 398506, 398507, 436164, 448718, 448730, 448762, 446766, 448799, 448802, 448806, 448817, 448819, 448848, 448850, 448860, 448890, 448897, 448905, 449884, 459010, 459011, 459040, 459046, 459076, 459082, 459083, 459086, 459087, 459088, 459157, and 459158.

In certain embodiments, the following antisense compounds target a region of SEQ ID NO: 2, a nucleic acid encoding human GCGR and demonstrate an $IC_{50}$ value of less than 0.2 μM: ISIS NOs: 304538, 398457, 398486, 398504, 398506, 398507, 448730, 448802, 448819, 448848, 448850, 448890, 449884, 459010, 459011, 459040, 459076, 459082, 459083, 459157, and 459158.

In certain embodiments, the following antisense compounds target a region of SEQ ID NO: 2, a nucleic acid encoding human GCGR and demonstrate an $IC_{50}$ value of less than 0.1 μM: ISIS NOs: 398457, 398507, 448819, 448848, 448850, 459010, 459011, 459083, 459157, and 459158.

Certain embodiments provide compounds comprising a modified oligonucleotide consisting of 17 linked nucleosides wherein the linked nucleosides comprise at least an 8 contiguous nucleobase portion that is complementary to an equal length nucleobase portion within the region selected from nucleotides 7270-7286, 7295-7311, 7319-7335, 7344-7360, 7368-7384, 7392-7408, 7416-7432, 7440-7456 or 10716-10734 of SEQ ID NO: 2.

In certain embodiments, the modified oligonucleotide has at least a 9, at least a 10, at least an 11, at least a 12, at least a 13, at least a 14, at least a 15, or at least a 16, contiguous nucleobase portion of which is complementary to an equal length portion within the region selected from nucleotides 7270-7286, 7295-7311, 7319-7335, 7344-7360, 7368-7384, 7392-7408, 7416-7432, 7440-7456 or 10716-10734 of SEQ ID NO: 2. In certain embodiments, the modified oligonucleotide is 90%, 95%, 99%, or 100% complementary to a nucleic acid encoding human GCGR eg. SEQ ID No: 2

Certain embodiments provide compounds comprising a modified oligonucleotide consisting of at least 17 linked nucleosides 60% complementary within the region selected from nucleotides 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, or 15743-15762 of SEQ ID NO: 2.

Certain embodiments provide compounds comprising a modified oligonucleotide consisting of at least 17 linked nucleosides 70% complementary within the region selected from nucleotides 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, or 15743-15762 of SEQ ID NO: 2.

Certain embodiments provide compounds comprising a modified oligonucleotide consisting of at least 17 linked nucleosides 80% complementary within the region selected from 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-

7456, 7783-7799, 8133-8152, 8144-8160, 9804-9823, 10718-10734, or 15743-15762 of SEQ ID NO: 2.

Certain embodiments provide compounds comprising a modified oligonucleotide consisting of at least 17 linked nucleosides 90% complementary within the region selected from nucleotides 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, or 15743-15762 of SEQ ID NO: 2.

Certain embodiments provide compounds comprising a modified oligonucleotide consisting of at least 17 linked nucleosides 95% complementary within the region selected from nucleotides 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, or 15743-15762 of SEQ ID NO: 2.

Certain embodiments provide compounds comprising a modified oligonucleotide consisting of at least 17 linked nucleosides 99% complementary within the region selected from nucleotides 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, or 15743-15762 of SEQ ID NO: 2.

Certain embodiments provide compounds comprising a modified oligonucleotide consisting of at least 17 linked nucleosides 100% complementary within the region selected from nucleotides 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, or 15743-15762 of SEQ ID NO: 2.

Certain embodiments provide compounds comprising a modified oligonucleotide consisting of 17 linked nucleosides 60% complementary within nucleotides 7270-7286, 7295-7311, 7319-7335, 7344-7360, 7368-7384, 7392-7408, 7416-7432, and 7440-7456 of SEQ ID NO: 2.

Certain embodiments provide compounds comprising a modified oligonucleotide consisting of 17 linked nucleosides 70% complementary within nucleotides 7270-7286, 7295-7311, 7319-7335, 7344-7360, 7368-7384, 7392-7408, 7416-7432, and 7440-7456 of SEQ ID NO: 2.

Certain embodiments provide compounds comprising a modified oligonucleotide consisting of 17 linked nucleosides 80% complementary within nucleotides 7270-7286, 7295-7311, 7319-7335, 7344-7360, 7368-7384, 7392-7408, 7416-7432, and 7440-7456 of SEQ ID NO: 2.

Certain embodiments provide compounds comprising a modified oligonucleotide consisting of 17 linked nucleosides 90% complementary within nucleotides 7270-7286, 7295-7311, 7319-7335, 7344-7360, 7368-7384, 7392-7408, 7416-7432, and 7440-7456 of SEQ ID NO: 2.

Certain embodiments provide compounds comprising a modified oligonucleotide consisting of 17 linked nucleosides 95% complementary within nucleotides 7270-7286, 7295-7311, 7319-7335, 7344-7360, 7368-7384, 7392-7408, 7416-7432, and 7440-7456 of SEQ ID NO: 2

Certain embodiments provide compounds comprising a modified oligonucleotide consisting of 17 linked nucleosides 99% complementary within nucleotides 7270-7286, 7295-7311, 7319-7335, 7344-7360, 7368-7384, 7392-7408, 7416-7432, and 7440-7456 of SEQ ID NO: 2.

Certain embodiments provide compounds comprising a modified oligonucleotide consisting of 17 linked nucleosides 100% complementary within nucleotides 7270-7286, 7295-7311, 7319-7335, 7344-7360, 7368-7384, 7392-7408, 7416-7432, and 7440-7456 of SEQ ID NO: 2.

Certain embodiments provide compounds comprising a modified oligonucleotide consisting of 17 linked nucleosides 60% complementary within nucleotides 10718-10734 of SEQ ID NO: 2.

Certain embodiments provide compounds comprising a modified oligonucleotide consisting of 17 linked nucleosides 70% complementary within nucleotides 10718-10734 of SEQ ID NO: 2.

Certain embodiments provide compounds comprising a modified oligonucleotide consisting of 17 linked nucleosides 80% complementary within nucleotides 10718-10734 of SEQ ID NO: 2.

Certain embodiments provide compounds comprising a modified oligonucleotide consisting of 17 linked nucleosides 90% complementary within nucleotides 10718-10734 of SEQ ID NO: 2.

Certain embodiments provide compounds comprising a modified oligonucleotide consisting of 17 linked nucleosides 95% complementary within nucleotides 10718-10734 of SEQ ID NO: 2.

Certain embodiments provide compounds comprising a modified oligonucleotide consisting of 17 linked nucleosides 99% complementary within nucleotides 10718-10734 of SEQ ID NO: 2.

Certain embodiments provide compounds comprising a modified oligonucleotide consisting of 17 linked nucleosides 100% complementary within nucleotides 10718-10734 of SEQ ID NO: 2.

In certain embodiments, such compounds or oligonucleotides targeted to a region of a GCGR nucleic acid have a contiguous nucleobase portion that is complementary to an equal length nucleobase portion of the region 7270-7286, 7295-7311, 7319-7335, 7344-7360, 7368-7384, 7392-7408, 7416-7432, 7440-7456 or 10718-10734 of SEQ ID NO: 2

In certain embodiments, the following nucleotide regions of SEQ ID NO: 2, when targeted by antisense compounds or oligonucleotides, displays at least 65% inhibition: 7267-7287, 7270-7286, 7292-7312, 7295-7311, 7316-7336, 7319-7335, 7341-7361, 7344-7360, 7365-7385, 7368-7384, 7389-7409, 7392-7408, 7416-7432, 7437-7457, 7440-7456, 7783-7799, 8133-8152, 8144-8160, 9804-9823, 10718-10734, or 15743-15762.

In certain embodiments, the nucleobase sequences recited in the following SEQ ID NOs display at least 70% inhibition of a GCGR nucleic acid: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 83, 84, 85, 86, 87, 88, 90, 91, 92, 93, 95, 96, 98, 99, 100, 101, 102, 103, 104, 105, 106, 107, 108, 109, 110, 111, 112, 113, 114, and 115.

In certain embodiments, the nucleobase sequences recited in the following SEQ ID NOs display at least 75% inhibition of a GCGR nucleic acid: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 81, 84, 85, 86, 87, 88, 90, 91, 92, 93, 95, 96, 98, 99, 101, 102, 103, 104, 105, 106, 107, 108, 109, 110, 111, 112, 113, 114, and 115.

In certain embodiments, the nucleobase sequences recited in the following SEQ ID NOs display at least 80% inhibition of a GCGR nucleic acid: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 81, 84, 85, 86, 87, 90, 91, 92, 93, 95, 96, 99, 102, 103, 104, 105, 106, 107, 108, 109, 110, 111, 112, 113, 114, 115.

In certain embodiments, the nucleobase sequences recited in the following SEQ ID NOs display at least 85% inhibition of a GCGR nucleic acid: 4, 5, 7, 8, 9, 10, 11, 12, 13, 14, 15, 18, 19, 20, 22, 24, 25, 26, 27, 28, 31, 34, 36, 38, 39, 40, 42, 43, 44, 45, 46, 47, 48, 49, 50, 51, 52, 53, 54, 55, 57, 58, 61, 62, 66, 67, 68, 71, 73, 74, 75, 76, 77, 85, 86, 87, 90, 91, 92, 93, 95, 96, 102, 103, 104, 107, 108, 109, 110, 111, 112, 113, 114, 115.

In certain embodiments, the nucleobase sequences recited in the following SEQ ID NOs display at least 90% inhibition of a GCGR nucleic acid: 5, 9, 10, 11, 12, 14, 15, 19, 24, 26, 38, 42, 43, 44, 47, 48, 49, 50, 51, 52, 53, 55, 57, 58, 62, 67, 76, 85, 86, 91, 92, 93, 95, 96, 102, 107, 109, 111, 112, 113, 114, and 115.

In certain embodiments, the nucleobase sequences recited in the following SEQ ID NOs display at least 95% inhibition of a GCGR nucleic acid: 9, 10, 24, 43, 52, 58, 86, 91, 92, 109, 111, and 112.

In certain embodiments, the compounds provided herein have a greater therapeutic potential than ISIS NOs: 315163, 325568, and 310457 (Disclosed in U.S. Pat. No. 7,399,853 and US Published Patent Application No. US2007-0087987, incorporated herein by reference). In certain embodiments, the compounds provided herein have better in vivo inhibition over ISIS NOs: 315163, 325568, and 310457. In certain embodiments, the compounds provided herein have a better tolerability profile than ISIS NOs: 315163, 325568, and 310457.

In certain embodiments, the compound provided herein consists of a single-stranded modified oligonucleotide.

In certain embodiments, the modified oligonucleotide consists of 8, 9, 10, 11, 12, 13, 14, 15, 16, 17, 18, 19, 20, 21, 22, 23, 24, 25, 26, 27, 28, 29, 30, 31, 32, 33, 34 or 35 linked nucleosides. In certain embodiments, the modified oligonucleotide consists of 21 linked nucleosides. In certain embodiments, the modified oligonucleotide consists of 20 linked nucleosides. In certain embodiments, the modified oligonucleotide consists of 19 linked nucleosides. In certain embodiments, the modified oligonucleotide consists of 18 linked nucleosides. In certain embodiments, the modified oligonucleotide consists of 17 linked nucleosides. In certain embodiments, the modified oligonucleotide consists of 16 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of ten linked deoxynucleosides, the 5' wing segment consisting of five linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 17 linked nucleosides, the gap segment consisting of ten linked deoxynucleosides, the 5' wing segment consisting of three linked nucleosides, the 3' wing segment consisting of four linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 21 linked nucleosides, the gap segment consisting of ten linked deoxynucleosides, the 5' wing segment consisting of five linked nucleosides, the 3' wing segment consisting of six linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NOs: 1-3, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NO: 2, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 4, 17, 24, 30, 31, 35, 37, 39, 40, 43, 48, 52, 56, 58, 60, 62, 63, 65, 68, 69, 70, 71, 72, 79, 79, 79, 98, 99, 100, 101, 102, 103, 104, 105, 106, 107, 108, 109, 110, 111, 112, 113, 114, and 115, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 17 or 31 wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 16 contiguous nucleobases of SEQ ID NO: 17, wherein the modified oligonucleotide comprises: a) a gap segment consisting of ten linked deoxynucleosides; b) a 5' wing segment consisting of four linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 16 contiguous nucleobases of SEQ ID NO: 31, wherein the modified oligonucleotide comprises: a) a gap segment consisting of ten linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 8 contiguous nucleobases complementary to an equal length portion of any of SEQ ID NOs: 1-3, wherein the modified oligonucleotide comprises: a) a gap segment consisting of ten linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 8 contiguous nucleobases complementary to an equal length portion of any of SEQ ID NO: 2, wherein the modified oligonucleotide comprises: a) a gap segment consisting of ten linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 16 contiguous nucleobases of SEQ ID NOs: 5, 6, 7, 8, 9, 10, 11, 12, 13, 14, 15, 16, 18, 19, 20, 21, 22, 23, 25, 26, 27, 28, 29, 32, 33, 34, 36, 38, 41, 42, 44, 45, 46, 47, 49, 50, 51, 53, 54, 55, 57, 59, 61, 64, 66, 67, 73, 74, 75, 76, 77, 78, 80, 81, 82, 83, 84, 88, 89, and 97, wherein the modified oligonucleotide comprises: a) a gap segment consisting of ten linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 16 contiguous nucleobases of SEQ ID NOs: 11 or 80, wherein the modified oligonucleotide comprises: a) a gap segment consisting of ten linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 16 contiguous nucleobases of SEQ ID NO: 11, wherein the modified oligonucleotide comprises: a) a gap segment consisting of ten linked deoxynucleosides; b) a 5' wing segment consisting of four linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 17 linked nucleosides having a nucleobase sequence comprising at least 16 contiguous nucleobases of SEQ ID NO: 80, wherein the modified oligonucleotide comprises: a) a gap segment consisting of ten linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 21 linked nucleosides having a nucleobase sequence comprising at least 20 contiguous nucleobases of SEQ ID NOs: 85 and 96, wherein the modified oligonucleotide comprises: a) a gap segment consisting of ten linked deoxynucleosides; b) a 5' wing segment consisting of five linked nucleosides; and c) a 3' wing segment consisting of six linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 21 linked nucleosides having a nucleobase sequence comprising at least 20 contiguous nucleobases of SEQ ID NOs: 85 wherein the modified oligonucleotide comprises: a) a gap segment consisting of ten linked deoxynucleosides; b) a 5' wing segment consisting of five linked nucleosides; and c) a 3' wing segment consisting of six linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

Certain embodiments provide methods, compounds, and compositions for inhibiting GCGR expression.

Certain embodiments provide a method of reducing GCGR expression in an animal comprising administering to the animal a compound as described herein. In certain embodiments, the compound comprises a modified oligonucleotide 12 to 30 linked nucleosides in length targeted to GCGR. In certain embodiments, the compound comprises a modified oligonucleotide 15 to 30 linked nucleosides in length targeted to GCGR. In certain embodiments, the compound comprises a modified oligonucleotide 18 to 21 linked nucleosides in length targeted to GCGR. In certain embodiments, the compound comprises a modified oligonucleotide 17 to 35 linked nucleosides in length targeted to GCGR. In certain embodiments, the compound comprises a modified oligonucleotide 17 to 25 linked nucleosides in length targeted to GCGR. In certain embodiments, the compound comprises a modified oligonucleotide 17 to 24 linked nucleosides in length targeted to GCGR. In certain embodiments, the compound comprises a modified oligonucleotide 17 to 23 linked nucleosides in length targeted to GCGR. In certain embodiments, the compound comprises a modified oligonucleotide 17 to 22 linked nucleosides in length targeted to GCGR. In certain embodiments, the compound comprises a modified oligonucleotide 17 to 21 linked nucleosides in length targeted to GCGR. In certain embodiments, the compound comprises a modified oligonucleotide 17 linked nucleosides in length targeted to GCGR. In certain embodiments, the compound comprises a modified oligonucleotide 20 linked nucleosides in length targeted to GCGR. In certain embodiments, the compound comprises a modified oligonucleotide 21 linked nucleosides in length targeted to GCGR.

Certain embodiments provide a method of preventing, ameliorating or treating a metabolic disease in an animal comprising administering to the animal a compound as described herein. In certain embodiments, the compound comprises a modified oligonucleotide 12 to 30 linked nucleosides in length targeted to GCGR. In certain embodiments, the compound comprises a modified oligonucleotide 17 linked nucleosides in length targeted to GCGR. Examples of metabolic diseases or disorders include, but are not limited to diabetes, hyperglycemia, prediabetes, obesity, non-alcoholic fatty liver disease (NAFLD), metabolic syndrome, insulin resistance, diabetic dyslipidemia, or hypertriglyceridemia or a combination thereof.

Certain embodiments provide a method of preventing, ameliorating or treating obesity in an animal comprising administering to the animal a compound as described herein. In certain embodiments, the compound comprises a modified oligonucleotide 12 to 30 linked nucleosides in length targeted to GCGR. In certain embodiments, the compound comprises a modified oligonucleotide 17 linked nucleosides in length targeted to GCGR. In certain embodiments, the compound comprises a modified oligonucleotide 20 linked nucleosides in length targeted to GCGR. In certain embodiments, the compound comprises a modified oligonucleotide 21 linked nucleosides in length targeted to GCGR. In certain embodiments, the compound or composition comprises the compound of ISIS NOs: 449884, 459014, 398471, 448766, or 459157. In certain embodiments, the compound or composition comprises the compound of ISIS NO: 449884. In certain embodiments, the compound or composition comprises the compound of ISIS NO: 459014.

Certain embodiments provide a method of preventing, ameliorating or treating diabetes in an animal comprising administering to the animal a compound as described herein. In certain embodiments, the compound comprises a modified oligonucleotide 12 to 30 linked nucleosides in length targeted to GCGR. In certain embodiments, the compound comprises a modified oligonucleotide 17 linked nucleosides in length targeted to GCGR. In certain embodiments, the compound comprises a modified oligonucleotide 20 linked nucleosides in length targeted to GCGR. In certain embodiments, the compound comprises a modified oligonucleotide 21 linked nucleosides in length targeted to GCGR. In certain embodiments, the compound or composition comprises the compound of ISIS NOs: 449884, 459014, 398471, 448766, or 459157. In certain embodiments, the compound or composition comprises the compound of ISIS NO: 449884. In certain embodiments, the compound or composition comprises the compound of ISIS NO: 459014.

Certain embodiments provide a method of reducing body weight in an animal comprising administering to the animal a compound as described herein. In certain embodiments, the compound comprises a modified oligonucleotide 12 to 30 linked nucleosides in length targeted to GCGR. In certain embodiments, the compound comprises a modified oligonucleotide 17 linked nucleosides in length targeted to GCGR. In certain embodiments, reduction of body weight in an animal prevents, ameliorates or treats a metabolic disease. In certain embodiments, reduction of body weight in an animal prevents, ameliorates or treats diabetes. In certain embodiments, reduction of body weight in an animal prevents, ameliorates or treats obesity. In certain embodiments, reduction of body weight in an animal prevents, ameliorates or treats metabolic syndrome. In certain embodiments, reduction of body weight in an animal prevents, ameliorates or treats insulin resistance. In certain embodiments, reduction of body weight in an animal prevents, ameliorates or treats hyperglycemia. In certain embodiments, reduction of body weight in an animal prevents, ameliorates or treats NAFLD. In certain embodiments, reduction of body weight in an animal prevents, ameliorates or treats diabetic dyslipidemia. In certain embodiments, the glucose levels are reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing glucose levels in an animal comprising administering to the animal a compound as described herein. In certain embodiments, the compound comprises a modified oligonucleotide 12 to 30 linked nucleosides in length targeted to GCGR. In certain embodiments, the compound comprises a modified oligonucleotide 17 linked nucleosides in length targeted to GCGR. In certain embodiments, reduction of glucose levels in an animal prevents, ameliorates or treats a metabolic disease. In certain embodiments, reduction of glucose levels in an animal prevents, ameliorates or treats diabetes. In certain embodiments, reduction of glucose levels in an animal prevents, ameliorates or treats obesity. In certain embodiments, reduction of glucose levels in an animal prevents, ameliorates or treats metabolic syndrome. In certain embodiments, reduction of glucose levels in an animal prevents, ameliorates or treats insulin resistance. In certain embodiments, reduction of glucose levels in an animal prevents, ameliorates or treats hyperglycemia. In certain embodiments, reduction of glucose levels in an animal prevents, ameliorates or treats NAFLD. In certain embodiments, reduction of glucose levels in an animal prevents, ameliorates or treats diabetic dyslipidemia. In certain embodiments, the glucose level is reduced by at least 5%, 10%, 20%, 30%, 35%, 40%, 45%, 50%, 55%, 60%, 65%, 70%, 75%, 80%, 85%, 90%, 95% or 100%.

In certain embodiments, GCGR has the human sequence as set forth in any of the GENBANK Accession Numbers: GENBANK Accession No. NM_000160.3 (incorporated herein as SEQ ID NO: 1) or GENBANK Accession No: NW_926918.1 truncated from nucleotides 16865000 to 16885000 (incorporated herein as SEQ ID NO: 2). In certain embodiments, GCGR has the rhesus monkey sequence as set forth in SEQ ID NO: 3.

In certain embodiments, the compounds or compositions provided herein comprise a salt thereof, and a pharmaceutically acceptable carrier or diluent. In certain embodiments, the composition comprises a modified oligonucleotide consisting of 17 to 35 linked nucleosides and having a nucleobase sequence comprising at least 17 contiguous nucleobases of a nucleobase sequence recited in SEQ ID NOs: 11, 17, 31, 80, or 85 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NOs: 11, 17, 31, 80, or 85 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NOs: 11, 17, 31, 80, or 85 or a salt thereof and a pharmaceutically acceptable carrier or diluent.

In certain embodiments, the compounds or compositions provided herein comprise a salt thereof, and a pharmaceutically acceptable carrier or diluent. In certain embodiments, the composition comprises a modified oligonucleotide consisting of 17 to 35 linked nucleosides and having a nucleobase sequence comprising at least 17 contiguous nucleobases of a nucleobase sequence recited in SEQ ID NO: 11 or a salt thereof and a pharmaceutically acceptable carrier or diluent. In certain embodiments, the composition comprises a modified oligonucleotide consisting of 17 to 25 linked nucleosides and having a nucleobase sequence comprising at least 17 contiguous nucleobases of a nucleobase sequence recited in SEQ ID NO: 16 or a salt thereof and a pharmaceutically acceptable carrier or diluent. In certain embodiments, the composition comprises a modified oligonucleotide consisting of 17 linked nucleosides and having a nucleobase sequence comprising at least 17 contiguous nucleobases of a nucleobase sequence recited in SEQ ID NO: 16 or a salt thereof and a pharmaceutically acceptable carrier or diluent.

In certain embodiments, the compounds or compositions provided herein comprise a salt thereof, and a pharmaceutically acceptable carrier or diluent. In certain embodiments, the composition comprises a modified oligonucleotide consisting of 17 to 35 linked nucleosides and having a nucleobase sequence comprising at least 17 contiguous nucleobases of a nucleobase sequence recited in SEQ ID NO: 80 or a salt thereof and a pharmaceutically acceptable carrier or diluent. In certain embodiments, the composition comprises a modified oligonucleotide consisting of 17 to 25 linked nucleosides and having a nucleobase sequence comprising at least 17 contiguous nucleobases of a nucleobase sequence recited in SEQ ID NO: 45 or a salt thereof and a pharmaceutically acceptable carrier or diluent. In certain embodiments, the composition comprises a modified oligonucleotide consisting of 17 linked nucleosides and having a nucleobase sequence comprising at least 17 contiguous nucleobases of a nucleobase sequence recited in SEQ ID NO: 45 or a salt thereof and a pharmaceutically acceptable carrier or diluent.

Certain embodiments provide a method for treating an animal with a GCGR related disease or condition comprising: a) identifying said animal with the GCGR related disease or condition, and b) administering to said animal a therapeutically effective amount of a compound comprising a modified oligonucleotide consisting of 12 to 30 linked nucleosides and having a nucleobase sequence at least 90% complementary to any of SEQ ID NOs: 1-3 as measured over the entirety of said modified oligonucleotide. In certain embodiments, the therapeutically effective amount of the compound administered to the animal treats or reduces the GCGR related disease or condition, or a symptom thereof, in the animal. In certain embodiments, the GCGR related disease or condition is obesity. In certain embodiments, the GCGR related disease or condition is diabetes.

Certain embodiments provide a method for treating an animal with a GCGR related disease or condition comprising: a) identifying said animal with the GCGR related disease or condition, and b) administering to said animal a therapeutically effective amount of a compound comprising a modified oligonucleotide consisting of 17 linked nucleosides and having a nucleobase sequence at least 100% complementary to any of SEQ ID NOs: 1-3 as measured over the entirety of said modified oligonucleotide. In certain embodiments, the therapeutically effective amount of the compound administered to the animal treats or reduces the GCGR related disease or condition, or a symptom thereof, in the animal. In certain embodiments, the GCGR related disease or condition is obesity. In certain embodiments, the GCGR related disease or condition is diabetes.

Certain embodiments provide methods of treating, preventing, or ameliorating a metabolic disease. In certain embodiments the metabolic disease is obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide methods comprising administering a compound as described herein to an animal. In certain embodiments, the method comprises administering to an animal a modified oligonucleotide consisting of 17 to 35 linked nucleosides and having a nucleobase sequence comprising at least 20 contiguous nucleobases of a nucleobase sequence recited in SEQ ID NOs: 11, 17, 31, 80, or 85.

Certain embodiments provide methods comprising administering a compound as described herein to an animal. In certain embodiments, the method comprises administering to an animal a modified oligonucleotide consisting of 17 to 35 linked nucleosides and having a nucleobase sequence comprising at least 17 contiguous nucleobases of a nucleobase sequence recited in SEQ ID NO: 1, 17, 31, 80, or 85.

Certain embodiments provide methods comprising administering a compound as described herein to an animal. In certain embodiments, the method comprises administering to an animal a modified oligonucleotide consisting of 17 to 35 linked nucleosides and having a nucleobase sequence comprising at least 17 contiguous nucleobases of a nucleobase sequence selected from among the nucleobase sequences recited in SEQ ID NO: 11.

Certain embodiments provide methods comprising administering a compound as described herein to an animal. In certain embodiments, the method comprises administering to an animal a modified oligonucleotide consisting of 17 to 35 linked nucleosides and having a nucleobase sequence comprising at least 17 contiguous nucleobases of a nucleobase sequence selected from among the nucleobase sequences recited in SEQ ID NO: 80

In certain embodiments, the animal is a human.

In certain embodiments, the administering prevents, treats, ameliorates, or slows progression of a metabolic disease as described herein.

In certain embodiments, the administering prevents, treats, ameliorates, or slows progression of obesity as described herein.

In certain embodiments, the administering prevents, treats, ameliorates, or slows progression of diabetes as described herein.

In certain embodiments, the compound is co-administered with a second agent.

In certain embodiments, the compound and the second agent are administered concomitantly.

In certain embodiments, the administering is parenteral administration.

Certain embodiments further provide a method to reduce GCGR mRNA or protein expression in an animal comprising administering to the animal a compound or composition as described herein to reduce GCGR mRNA or protein expression in the animal. In certain embodiments, the animal is a human. In certain embodiments, reducing GCGR mRNA or protein expression prevents, treats, ameliorates, or slows progression of metabolic disease. In certain embodiments, the metabolic disease or condition is diabetes. In certain embodiments, the metabolic disease or condition is obesity.

Certain embodiments provide a method for treating a human with a metabolic disease comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with obesity comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with diabetes comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Further provided is a method for reducing or preventing metabolic disease comprising administering to a human a therapeutically effective amount compound or composition as described herein, thereby reducing or preventing metabolic disease.

Further provided is a method for reducing or preventing obesity comprising administering to a human a therapeutically effective amount compound or composition as described herein, thereby reducing or preventing diabetes.

Further provided is a method for reducing or preventing diabetes comprising administering to a human a therapeutically effective amount compound or composition as described herein, thereby reducing or preventing diabetes.

Further provided is a method for ameliorating a symptom of metabolic disease, comprising administering to a human in need thereof a compound comprising a modified oligonucleotide consisting of 17 to 35 linked nucleosides, wherein said modified oligonucleotide specifically hybridizes to SEQ ID NO: 1, 2, or 3, thereby ameliorating a symptom of metabolic disease in the human.

Further provided is a method for ameliorating a symptom of diabetes, comprising administering to a human in need thereof a compound comprising a modified oligonucleotide consisting of 17 to 35 linked nucleosides, wherein said modified oligonucleotide specifically hybridizes to SEQ ID NO: 1, 2, or 3, thereby ameliorating a symptom of diabetes in the human.

Further provided is a method for ameliorating a symptom of metabolic disease, comprising administering to a human in need thereof a compound comprising a modified oligonucleotide consisting of 12 to 30 linked nucleosides, wherein said modified oligonucleotide specifically hybridizes to SEQ ID NO: 1, 2, or 3, thereby ameliorating a symptom of metabolic disease in the human.

Further provided is a method for ameliorating a symptom of diabetes, comprising administering to a human in need thereof a compound comprising a modified oligonucleotide consisting of 12 to 30 linked nucleosides, wherein said modified oligonucleotide specifically hybridizes to SEQ ID NO: 1, 2, or 3, thereby ameliorating a symptom of diabetes in the human.

Further provided is a method for ameliorating a symptom of metabolic disease, comprising administering to a human in need thereof a compound comprising a modified oligonucleotide consisting of 17 linked nucleosides, wherein said modified oligonucleotide specifically hybridizes to SEQ ID NO: 1, 2, or 3, thereby ameliorating a symptom of metabolic disease in the human.

Further provided is a method for ameliorating a symptom of diabetes, comprising administering to a human in need thereof a compound comprising a modified oligonucleotide consisting of 17 linked nucleosides, wherein said modified oligonucleotide specifically hybridizes to SEQ ID NO: 1, 2, or 3, thereby ameliorating a symptom of diabetes in the human.

Further provided is a method for reducing the rate of progression of a symptom associated with metabolic disease, comprising administering to a human in need thereof a compound comprising a modified oligonucleotide consisting of 17 to 35 linked nucleosides, wherein said modified oligonucleotide specifically hybridizes to SEQ ID NO: 1, 2, or 3, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 17 to 35 linked nucleosides, wherein said modified oligonucleotide specifically hybridizes to SEQ ID NO: 1, 2, or 3, thereby reducing the rate of progression a symptom of diabetes in the human.

Further provided is a method for reducing the rate of progression of a symptom associated with metabolic disease, comprising administering to a human in need thereof a compound comprising a modified oligonucleotide consisting of 12 to 30 linked nucleosides, wherein said modified oligonucleotide specifically hybridizes to SEQ ID NO: 1, 2, or 3, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 12 to 30 linked nucleosides, wherein said modified oligonucleotide specifically hybridizes to SEQ ID NO: 1, 2, or 3, thereby reducing the rate of progression a symptom of diabetes in the human.

Further provided is a method for reducing the rate of progression of a symptom associated with metabolic disease, comprising administering to a human in need thereof a compound comprising a modified oligonucleotide consisting of 17 linked nucleosides, wherein said modified oligonucleotide specifically hybridizes to SEQ ID NO: 1, 2, or 3, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 17 linked nucleosides, wherein said modified oligonucleotide specifically hybridizes to SEQ ID NO: 1, 2, or 3, thereby reducing the rate of progression a symptom of diabetes in the human.

Also provided are methods and compounds for the preparation of a medicament for the treatment, prevention, or amelioration of metabolic disease.

Also provided are methods and compounds for the preparation of a medicament for the treatment, prevention, or amelioration of obesity.

Also provided are methods and compounds for the preparation of a medicament for the treatment, prevention, or amelioration of diabetes.

Also provided are methods and compounds for the preparation of a medicament for the treatment, prevention, or amelioration of metabolic syndrome.

Certain embodiments provide the use of a compound as described herein in the manufacture of a medicament for treating, ameliorating, or preventing metabolic disease.

Certain embodiments provide the use of a compound as described herein in the manufacture of a medicament for treating, ameliorating, or preventing obesity.

Certain embodiments provide the use of a compound as described herein in the manufacture of a medicament for treating, ameliorating, or preventing diabetes.

Certain embodiments provide the use of a compound as described herein in the manufacture of a medicament for treating, ameliorating, or preventing metabolic syndrome.

Certain embodiments provide a compound as described herein for use in treating, preventing, or ameliorating metabolic disease as described herein by combination therapy with an additional agent or therapy as described herein. Agents or therapies can be co-administered or administered concomitantly.

Certain embodiments provide a compound as described herein for use in treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating obesity as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein in a patient who is subsequently administered an additional agent or therapy as described herein.

Certain embodiments provide the use of a compound as described herein in the manufacture of a medicament for treating, preventing, or ameliorating obesity as described herein in a patient who is subsequently administered an additional agent or therapy as described herein.

Certain embodiments provide the use of a compound as described herein in the manufacture of a medicament for treating, preventing, or ameliorating diabetes as described herein in a patient who is subsequently administered an additional agent or therapy as described herein.

Certain embodiments provide the use of a compound as described herein in the manufacture of a medicament for treating, preventing, or ameliorating metabolic syndrome as described herein in a patient who is subsequently administered an additional agent or therapy as described herein.

Certain embodiments provide a kit for treating, preventing, or ameliorating metabolic disease as described herein wherein the kit comprises:

(i) a compound as described herein; and alternatively (ii) an additional agent or therapy as described herein.

Certain embodiments provide a kit for treating, preventing, or ameliorating obesity as described herein wherein the kit comprises:

(i) a compound as described herein; and alternatively (ii) an additional agent or therapy as described herein.

Certain embodiments provide a kit for treating, preventing, or ameliorating diabetes as described herein wherein the kit comprises:

(i) a compound as described herein; and alternatively (ii) an additional agent or therapy as described herein.

Certain embodiments provide a kit for treating, preventing, or ameliorating metabolic syndrome as described herein wherein the kit comprises:

(i) a compound as described herein; and alternatively (ii) an additional agent or therapy as described herein.

A kit as described herein may further include instructions for using the kit to treat, prevent, or ameliorate metabolic disease as described herein by combination therapy as described herein. In certain embodiments, the metabolic disease is obesity. In certain embodiments, the metabolic disease is diabetes.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a GCGR nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 50, 15 to 30, 18 to 21, 20 to 80, 20 to 35, 20 to 30, 20 to 29, 20 to 28, 20 to 27, 20 to 26, 20 to 25, 20 to 24, 20 to 23, 20 to 22, 20 to 21 or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a GCGR nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, wings may include several modified sugar moieties, including, for example 2'-MOE and constrained ethyl. In certain embodiments, wings may include several modified and unmodified sugar moieties. In certain embodiments, wings may include various combinations of 2'-MOE nucleosides, constrained ethyl nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same, in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, antisense compounds targeted to a GCGR nucleic acid possess a 3-10-4 gapmer motif.

In certain embodiments, antisense compounds targeted to a GCGR nucleic acid possess a 5-10-5 gapmer motif.

In certain embodiments, antisense compounds targeted to a GCGR nucleic acid possess a 5-10-6 gapmer motif.

In certain embodiments, antisense compounds targeted to a GCGR nucleic acid possess a 3-10-3 gapmer motif.

In certain embodiments, antisense compounds targeted to a GCGR nucleic acid possess a 4-10-4 gapmer motif.

In certain embodiments, antisense compounds targeted to a GCGR nucleic acid possess a 4-10-5 gapmer motif.

Target Nucleic Acids, Target Regions and Nucleotide Sequences

In certain embodiments, the GCGR nucleic acid is any of the sequences set forth in GENBANK Accession No. NM_000160.3 (incorporated herein as SEQ ID NO: 1), GENBANK Accession No. NW_926918.1 truncated from nucleotides 16865000 to 16885000 (incorporated herein as SEQ ID NO: 2); and the rhesus monkey sequence as set forth in SEQ ID NO: 3.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for GCGR can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in GCGR mRNA levels are indicative of inhibition of GCGR expression. Reductions in levels of a GCGR protein are also indicative of inhibition of target mRNA expression. Further, phenotypic changes are indicative of inhibition of GCGR expression. In certain embodiments, reduced glucose levels, reduced lipid levels, and reduced body weight can be indicative of inhibition of GCGR expression. In certain embodiments, amelioration of symptoms associated with metabolic disease can be indicative of inhibition of GCGR expression. In certain embodiments, amelioration of symptoms associated with diabetes can be indicative of inhibition of GCGR expression. In certain embodiments, reduction of insulin resistance is indicative of inhibition of GCGR expression. In certain embodiments, reduction of diabetes biomarkers can be indicative of inhibition of GCGR expression.

Hybridization

In some embodiments, hybridization occurs between an antisense compound disclosed herein and a GCGR nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a GCGR nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a GCGR nucleic acid).

An antisense compound may hybridize over one or more segments of a GCGR nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a GCGR nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a GCGR nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a GCGR nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a GCGR nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. In certain embodiments, the antisense compounds are complementary to at least a 16 nucleobase portion of a target segment. In certain embodiments, the antisense compounds are complementary to at least a 17 nucleobase portion of a target segment. In certain embodiments, the antisense compounds are complementary to at least a 18 nucleobase portion of a target segment. In certain embodiments, the antisense compounds are complementary to at least a 19 nucleobase portion of a target segment. In certain embodiments, the antisense compounds are complementary to at least a 20 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 91%, 92%, 93%, 94%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a GCGR nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substitutent groups (including 5' and 2' substituent groups); bridging of non-geminal ring atoms to form bicyclic nucleic acids (BNA); replacement of the ribosyl ring oxygen atom with S, N(R), or C(R1)(R)2 (R═H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US200510130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-$OCH_3$, and 2'-O($CH_2$)2$OCH_3$ substituent groups. The substituent at the 2' position can also be selected from allyl, amino, azido, thio, O-allyl, O—$C_1$-$C_{10}$ alkyl, $OCF_3$, O$(CH_2)_2SCH_3$, O$(CH_2)_2$—O—N(Rm)(Rn), and O—$CH_2$—C(═O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-($CH_2$)—O-2' (LNA); 4'-($CH_2$)—S-2; 4'-$(CH_2)_2$—O-2' (ENA); 4'-CH($CH_3$)—O-2' and 4'-CH($CH_2OCH_3$)—O-2', and analogs thereof (see, U.S. Pat. No. 7,399,845, issued on Jul. 15, 2008); 4'-C($CH_3$)($CH_3$)—O-2', and analogs thereof (see, published PCT International Application WO2009/006478, published Jan. 8, 2009); 4'-$CH_2$—N($OCH_3$)-2', and analogs thereof (see, published PCT International Application WO2008/150729, published Dec. 11, 2008); 4'-$CH_2$—O—N($CH_3$)-2' (see, published U.S. Patent Application US2004/0171570, published Sep. 2, 2004); 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, Chattopadhyaya, et al., *J. Org. Chem.*, 2009, 74, 118-134); and 4'-$CH_2$—C(═$CH_2$)-2', and analogs thereof (see, published PCT International Application WO 2008/154401, published on Dec. 8, 2008). Also see, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(=$NR_a$)—, —C(=O)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —$[C(R_a)(R_b)]_n$—, —$[C(R_a)(R_b)]_n$—O—, —$C(R_aR_b)$—N(R)—O— or, —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2', and 4'-$CH_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-Methyleneoxy (4'-$CH_2$—O-2') BNA, (B) β-D-Methyleneoxy (4'-$CH_2$—O-2') BNA, (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-$CH(CH_3)$—O-2') BNA, (G) methylene-thio (4'-$CH_2$—S-2') BNA, (H) methylene-amino (4'-CH2-N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

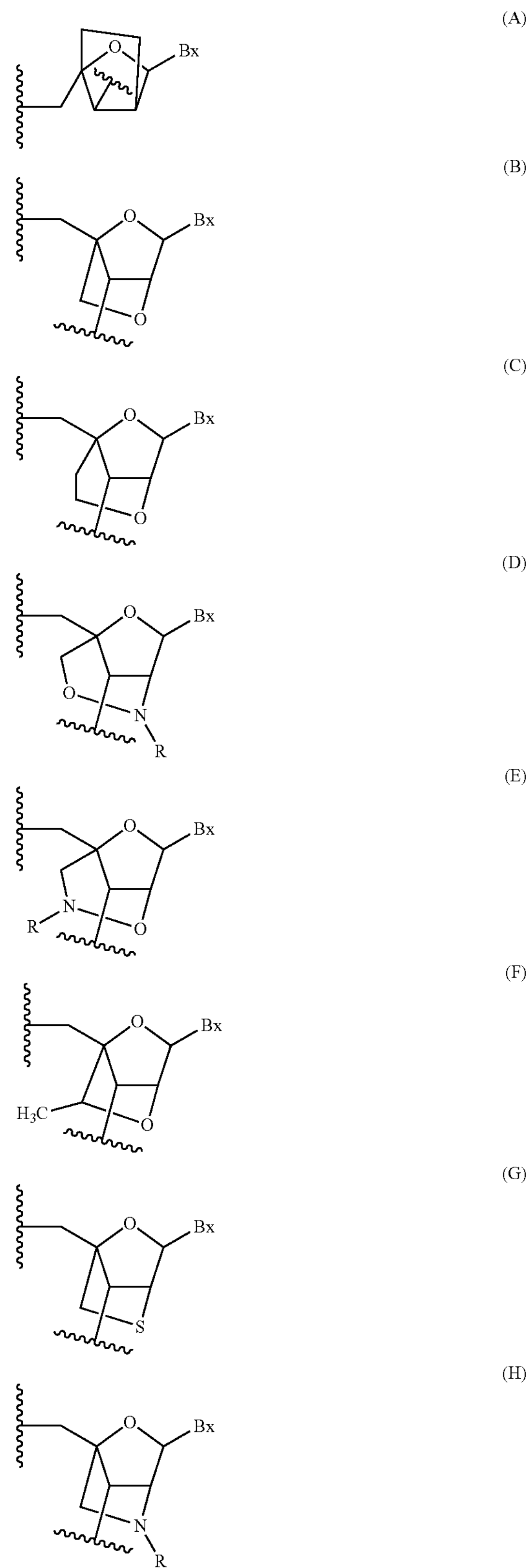

-continued (I)

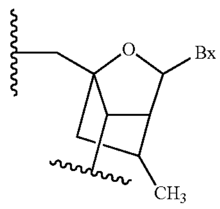

(J)

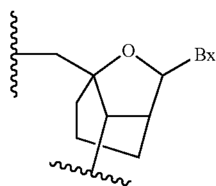

wherein Bx is the base moiety and R is, independently, H, a protecting group or $C_1$-$C_{12}$ alkyl.

In certain embodiments, bicyclic nucleoside having Formula I:

I

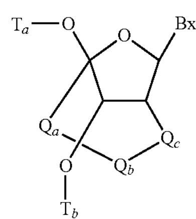

wherein:

Bx is a heterocyclic base moiety;

-$Q_a$-$Q_b$-$Q_c$- is —$CH_2$—N($R_c$)—$CH_2$—, —C(═O)—N($R_c$)—$CH_2$—, —$CH_2$—O—N($R_c$)—, —$CH_2$—N($R_c$)—O—, or —N($R_c$)—O—$CH_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

II

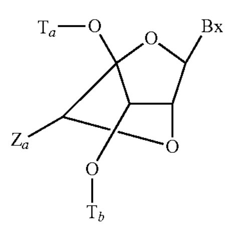

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(═X)$J_c$, and $NJ_eC$(═X)$NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

III

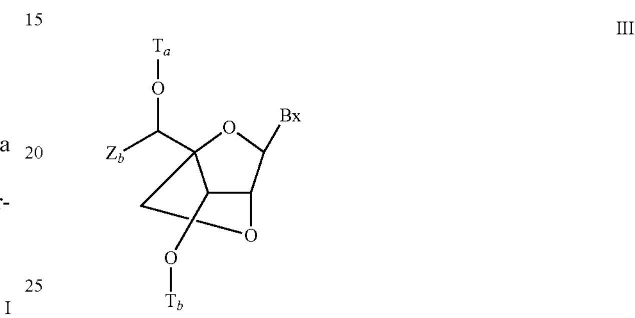

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(═O)—).

In certain embodiments, bicyclic nucleoside having Formula IV:

IV

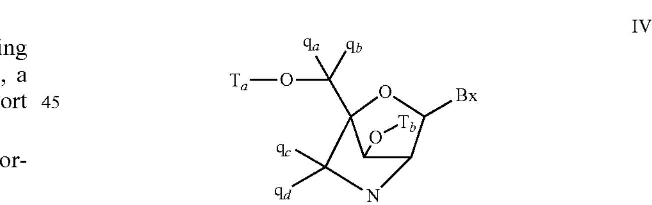

wherein:

Bx is a heterocyclic base moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

V

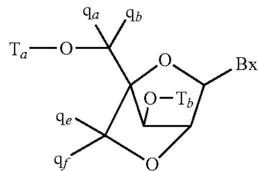

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(═O)$OJ_j$, C(═O)$NJ_jJ_k$, C(═O)$J_j$, O—C(═O)$NJ_jJ_k$, N(H)C(═NH)$NJ_jJ_k$, N(H)C(═O)$NJ_jJ_k$ or N(H)C(═S)$NJ_jJ_k$;

or $q_e$ and $q_f$ together are ═C($q_g$)($q_h$);

$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

VI

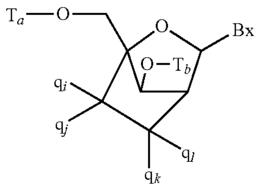

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(═O)$OJ_j$, C(═O)$NJ_jJ_k$, C(═O)$J_j$, O—C(═O)$NJ_jJ_k$, N(H)C(═NH)$NJ_jJ_k$, N(H)C(═O)$NJ_jJ_k$, or N(H)C(═S)$NJ_jJ_k$; and $q_i$ and $q_j$ or $q_l$ and $q_k$ together are ═C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-$(CH_2)_3$-2' bridge and the alkenyl analog, bridge 4'-CH═CH—$CH_2$-2', have been described (see, e.g., Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F—HNA), or those compounds having Formula X:

Formula X:

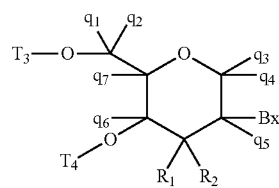

wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-$OCH_3$" or "2'-O-methyl" each refers to a sugar comprising an $OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a GCGR nucleic acid comprise one or more modified nucleobases. In certain embodiments, gap-widened antisense oligonucleotides targeted to a GCGR nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a GCGR nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a GCGR nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of GCGR nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE 2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a GCGR nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a GCGR nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of GCGR nucleic acids can be assessed by measuring GCGR protein levels. Protein levels of GCGR can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat GCGR are commercially available.

In Vivo Testing of Antisense Compounds

Antisense compounds, for example, antisense oligonucleotides, are tested in animals to assess their ability to inhibit expression of GCGR and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in GCGR nucleic acid expression are measured. Changes in GCGR protein levels are also measured.

Certain Indications

In certain embodiments, provided herein are methods of treating an individual comprising administering one or more pharmaceutical compositions as described herein. In certain embodiments, the individual has metabolic related disease.

As shown in the examples below, compounds targeted to GCGR, as described herein, have been shown to reduce the severity of physiological symptoms of metabolic related diseases, including metabolic syndrome, diabetes mellitus, insulin resistance, diabetic dyslipidemia, hypertriglyceridemia, obesity and weight gain. In certain of the experiments, the compounds reduced blood glucose levels, e.g., the animals continued to experience symptoms, but the symptoms were less severe compared to untreated animals. In other experiments, however, the compounds appear to reduce the symptoms of diabetes; e.g., animals treated for a longer period of time experienced less severe symptoms than those administered the compounds for a shorter period of time. In other experiments, however, the compounds appear to inhibit weight gain; e.g., animals treated for a longer period of time experienced less severe symptoms than those administered the compounds for a shorter period of time. In other experiments, however, the compounds appear to inhibit hypertriglyceridemia; e.g., animals treated for a longer period of time experienced less severe signs and/or symptoms than those administered the compounds for a shorter period of time. The ability of the compounds exemplified below to restore function therefore demonstrates that symptoms of the disease may be reversed by treatment with a compound as described herein.

Diabetes mellitus is characterized by numerous physical and physiological signs and/or symptoms. Any symptom known to one of skill in the art to be associated with Type 2 diabetes can be ameliorated or otherwise modulated as set forth above in the methods described above. In certain embodiments, the symptom or sign is a physical symptom or sign such as increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums. In certain embodiments, the symptom or sign is a physiological symptom or sign selected from the group consisting of increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical symptom or sign is increased glucose levels. In certain embodiments, the sign or symptom is weight gain. In certain embodiments, the symptom is frequent urination. In certain embodiments, the symptom is unusual thirst. In certain embodiments, the symptom is extreme hunger. In certain embodiments, the symptom is extreme fatigue. In certain embodiments, the symptom is blurred vision. In certain embodiments, the symptom is frequent infections. In certain embodiments, the symptom is tingling or numbness at the extremities. In certain embodiments, the symptom is dry and itchy skin. In certain embodiments, the sign or symptom is weight loss. In certain embodiments, the symptom is slow-healing sores. In certain embodiments, the symptom is swollen gums. In certain embodiments, the symptom or sign is increased insulin resistance. In certain embodiments, the symptom or sign is increased glucose levels. In certain embodiments, the symptom or sign is increased fat mass. In certain embodiments, the symptom or sign is decreased metabolic rate. In certain embodiments, the symptom or sign is decreased glucose clearance. In certain embodiments, the symptom or sign is decreased glucose tolerance. In certain embodiments, the symptom or sign is decreased insulin sensitivity. In certain embodiments, the symptom or sign is decreased hepatic insulin sensitivity. In certain embodiments, the symptom or sign is increased adipose tissue size and weight. In certain embodiments, the symptom or sign is increased body fat. In certain embodiments, the sign or symptom is increased body weight.

In certain embodiments, provided are methods of treating an individual comprising administering one or more pharmaceutical compositions as described herein. In certain embodiments, the individual has metabolic related disease.

In certain embodiments, administration of an antisense compound targeted to a GCGR nucleic acid results in reduction of GCGR expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to GCGR are used for the preparation of a medicament for treating a patient suffering or susceptible to metabolic related disease.

In certain embodiments, the methods described herein include administering a compound comprising a modified oligonucleotide having a contiguous nucleobases portion as described herein of a sequence recited in SEQ ID NO: 11 (ISIS 449884).

In certain embodiments, the methods described herein include administering a compound comprising a modified oligonucleotide having a contiguous nucleobases portion as described herein of a sequence recited in SEQ ID NO: 80 (ISIS 459014).

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, the second compound is administered prior to administration of a pharmaceutical composition described herein. In certain embodiments, the second compound is administered following administration of a pharmaceutical composition described herein. In certain embodiments, the second compound is administered at the same time as a pharmaceutical composition described herein. In certain embodiments, the dose of a co-administered second compound is the same as the dose that would be administered if the second compound was administered alone. In certain embodiments, the dose of a co-administered second compound is lower than the dose that would be administered if the second compound was administered alone. In certain embodiments, the dose of a co-administered second compound is greater than the dose that would be administered if the second compound was administered alone.

In certain embodiments, the co-administration of a second compound enhances the effect of a first compound, such that co-administration of the compounds results in an effect that is greater than the effect of administering the first compound alone. In certain embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

In certain embodiments, second agents include, but are not limited to, a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose-lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose-lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is ISIS 113715.

In a certain embodiment, glucose-lowering therapy is therapeutic lifestyle change.

In certain embodiments, second agents include, but are not limited to, lipid-lowering agents. The lipid-lowering agent can include, but is not limited to atorvastatin, simvastatin, rosuvastatin, and ezetimibe. In certain such embodiments, the lipid-lowering agent is administered prior to administration of a pharmaceutical composition described herein. In certain such embodiments, the lipid-lowering agent is administered following administration of a pharmaceutical composition described herein. In certain such embodiments the lipid-lowering agent is administered at the same time as a pharmaceutical composition described herein. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, second agents include, but are not limited to an anti-obesity drug or agent. Such anti-obesity agents include but are not limited to Orlistat, Sibutramine, or Rimonabant, and may be administered as described above as adipose or body weight lowering agents. In certain embodiments, the antisense compound may be co-administered with appetite suppressants. Such appetite suppressants include but are not limited to diethylpropion tenuate, mazindol, orlistat, phendimetrazine, phentermine, and sibutramine and may be administered as described herein. In certain embodiment, the anti-obesity agents are CNS based such as, but not limited to, sibutramine or GLP-1 based such as, but not limited to, liraglutide.

Formulations

The compounds provided herein may also be admixed, conjugated or otherwise associated with other molecules, molecule structures or mixtures of compounds, as for example, liposomes, receptor-targeted molecules, or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds provided herein can be include in a pharmaceutical composition or formulation. The pharmaceutical composition can include any pharmaceutically acceptable salts, esters, or salts of such esters, or any other compound which, upon administration to an animal, including a human, is capable of providing (directly or indirectly) the biologically active metabolite or residue thereof.

The term “pharmaceutically acceptable salts” refers to physiologically and pharmaceutically acceptable salts of the compounds provided herein: i.e., salts that retain the desired biological activity of the parent compound and do not impart undesired toxicological effects thereto. The term “pharmaceutically acceptable salt” includes a salt prepared from pharmaceutically acceptable non-toxic acids or bases, including inorganic or organic acids and bases. For oligonucleotides, preferred examples of pharmaceutically acceptable salts and their uses are further described in U.S. Pat. No. 6,287,860, which is incorporated herein in its entirety. Sodium salts have been shown to be suitable forms of oligonucleotide drugs.

The term “pharmaceutically acceptable derivative” encompasses, but is not limited to, pharmaceutically acceptable salts, solvates, hydrates, esters, prodrugs, polymorphs, isomers, isotopically labeled variants of the compounds described herein.

The pharmaceutical compositions described herein may be administered in a number of ways depending upon whether local or systemic treatment is desired and upon the area to be treated. Administration may be parenteral. Parenteral administration includes, but is not limited to subcutaneous, intravenous or intramuscular injection or infusion.

Parenteral administration, is preferred to target GCGR expression in the liver and plasma. Oligonucleotides with at least one 2'-O-methoxyethyl modification are believed to be particularly useful for parenteral administration.

The pharmaceutical formulations described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both.

The compositions described herein may also be formulated as suspensions in aqueous, non-aqueous or mixed media. The suspension may also contain stabilizers.

Pharmaceutical compositions described herein include, but are not limited to, solutions, emulsions, and liposome-containing formulations. The pharmaceutical compositions and formulations described herein may comprise one or more penetration enhancers, carriers, excipients or other active or inactive ingredients.

Formulations include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Liposomes and their uses are further described in U.S. Pat. No. 6,287,860, which is incorporated herein in its entirety.

In another embodiment, formulations include saline formulations. In certain embodiments, a formulation consists of the compounds described herein and saline. In certain embodiments, a formulation consists essentially of the compounds described herein and saline. In certain embodiments, the saline is pharmaceutically acceptable grade saline. In certain embodiments, the saline is buffered saline. In certain embodiments, the saline is phosphate buffered saline (PBS).

In certain embodiments, a formulation excludes liposomes. In certain embodiments, the formulation excludes sterically stabilized liposomes. In certain embodiments, a formulation excludes phospholipids. In certain embodiments, the formulation consists essentially of the compounds described herein and saline and excludes liposomes.

The pharmaceutical formulations and compositions may also include surfactants. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. Penetration enhancers and their uses are further described in U.S. Pat. No. 6,287,860, which is incorporated herein in its entirety.

One of skill in the art will recognize that formulations are routinely designed according to their intended use, i.e. route of administration.

Compositions and formulations for parenteral administration, including subcutaneous, intravenous, and intramuscular injection or infusion may include sterile aqueous solutions which may also contain buffers, diluents and other suitable additives such as, but not limited to, penetration enhancers, carrier compounds and other pharmaceutically acceptable carriers or excipients.

In another related embodiment, compositions provided herein may contain one or more antisense compounds, particularly oligonucleotides, targeted to a first nucleic acid and one or more additional antisense compounds targeted to a second nucleic acid target. Alternatively, compositions provided herein may contain two or more antisense compounds targeted to different regions of the same nucleic acid target. Numerous examples of antisense compounds are known in the art. Two or more combined compounds may be used together or sequentially.

Dosing

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or at desired intervals. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

Certain Compounds

About seven hundred and seventy seven newly designed and previously disclosed antisense compounds of various lengths, motifs and backbone composition were tested for their effect on human GCGR mRNA in vitro in several cell types (Example 1). The new compounds were compared with previously designed compounds, including ISIS 310457, ISIS 315163, and ISIS 325568 which have previously been determined to be some of the most potent antisense compounds in vitro (see e.g., U.S. Patent Publication No. U.S. Pat. No. 7,399,853 and US Published Patent Application No. US2007-0087987). Of the about seven hundred and seventy seven newly designed and previously designed antisense compounds, only those compounds which were selected for further study based on in vitro potency are presented. The selected compounds were tested for dose dependent inhibition in cynomolgus primary hepatocytes and HepG2 cells (Examples 5-13). Of the 120 compounds tested by dose response assays, 33 antisense oligonucleotides were selected for in vivo tolerability assays.

The final selected 33 oligonucleotides, ISIS 304538 (SEQ ID NO: 112), ISIS 304539 (SEQ ID NO: 113), ISIS 325568 (SEQ ID NO: 4), ISIS 398457 (SEQ ID NO: 9), ISIS 398471 (SEQ ID NO: 17), ISIS 398486 (SEQ ID NO: 24), ISIS 398491 (SEQ ID NO: 105), ISIS 398506 (SEQ ID NO: 108), ISIS 398507 (SEQ ID NO: 109), ISIS 398508 (SEQ ID NO: 110), ISIS 436034 (SEQ ID NO: 35), ISIS 436140 (SEQ ID NO: 102), ISIS 436141 (SEQ ID NO: 114), ISIS 448718 (SEQ ID NO: 99), ISIS 448730 (SEQ ID NO: 100), ISIS 448754 (SEQ ID NO: 98), ISIS 448766 (SEQ ID NO: 31), ISIS 448817 (SEQ ID NO: 52), ISIS 448818 (SEQ ID NO: 56), ISIS 448819 (SEQ ID NO: 58), ISIS 448848 (SEQ ID NO: 62), ISIS 448860 (SEQ ID NO: 65), ISIS 448890 (SEQ ID NO: 68), ISIS 449884 (SEQ ID NO: 11), ISIS 449954 (SEQ ID NO: 51), ISIS 449956 (SEQ ID NO: 54), ISIS 459014 (SEQ ID NO: 80), ISIS 459024 (SEQ ID NO: 89), ISIS 459032 (SEQ ID NO: 81), ISIS 459040 (SEQ ID NO: 82), ISIS 459046 (SEQ ID NO: 83), ISIS 459076 (SEQ ID NO: 84), and ISIS 459157 (SEQ ID NO: 85), were tested for tolerability in a CD1 mouse model, as well as a Sprague-Dawley rat model. The compounds are complementary to the regions 548-567, 2016-2035, and 2018-2037 of SEQ ID NO: 1, and 6682-6698, 7267-7283, 7270-7286, 7292-7308, 7295-7311, 7316-7332, 7317-7333, 7319-7335, 7341-7357, 7344-7360, 7365-7381, 7368-7384, 7389-7405, 7392-7408, 7416-7432, 7437-7453, 7440-7456, 7783-7799, 8030-8049, 8133-8152, 8141-8160, 8144-8160, 9002-9021, 9008-9027, 9245-9264, 9246-9262, 9804-9823, 10676-10695, 10718-10734, 12030-12049, 12031-12050, 12031-12047, 12032-12051, 12033-12052, 12033-12049, 12036-12055, 12175-12194, 12178-12194, 13490-13509, 14138-14157, 15075-15094, 15743-15762, 15744-15763, 15745-15764, and 15746-15765 of SEQ ID NO: 2.

In the in vivo models, body weights and organ weights, liver function markers (such as alanine transaminase, aspartate transaminase and bilirubin), and kidney function markers (such as BUN and creatinine) were measured. In the mouse model, ISIS 304538, ISIS 325568, ISIS 398457, ISIS 398471, ISIS 398491, ISIS 436140, ISIS 448754, ISIS 448766, ISIS 448818, ISIS 449884, ISIS 449956, ISIS 459014, ISIS 459024, ISIS 459032, ISIS 459040, ISIS 459046, ISIS 459076, and ISIS 459157 were tolerable in terms of transaminase levels (Example 11). In the Sprague-Dawley rat model, ISIS 325568, ISIS 398457, ISIS 398471, ISIS 398491, ISIS 436140, ISIS 448730, ISIS 448754, ISIS 448817, ISIS 448818, ISIS 448848, ISIS 449884, ISIS 449956, ISIS 459014, ISIS 459032, ISIS 459040, ISIS 459046, ISIS 459076, and ISIS 459157 were deemed tolerable in terms of levels of both liver function and kidney function markers (Example 12).

Nine compounds, ISIS 325568 (SEQ ID NO: 4), ISIS 398471 (SEQ ID NO: 17), ISIS 436140 (SEQ ID NO: 102), ISIS 448766 (SEQ ID NO: 31), ISIS 449884 (SEQ ID NO: 11), ISIS 459014 (SEQ ID NO: 80), ISIS 459032 (SEQ ID NO: 81), ISIS 459040 (SEQ ID NO: 82), and ISIS 459157 (SEQ ID NO: 85), were selected from the tolerability models and assayed for long-term effects on tolerability in a CD/1GS rat model for 13 weeks (Example 13). Organ weights, liver function markers (such as alanine transaminase, aspartate transaminase and bilirubin), and kidney function markers (such as BUN and creatinine) were measured. The nine compounds were also tested for their viscosity, which was found to be optimal for all the oligonucleotides (Example 14)

ISIS 449884, which demonstrated very good tolerability in all three in vivo models, was tested for its half-life in CD1 mouse liver (Example 15). The half-life of ISIS 449884 was calculated to be 15 days.

Final evaluation of these studies (Examples 11-15) led to the selection of eight oligonucleotides having a nucleobase sequence of SEQ ID NO: 17 (ISIS 398471), 102 (ISIS 436140), 31 (ISIS 448766), 11 (ISIS 449884), 80 (ISIS 459014), 81 (ISIS 459032), 82 (ISIS 459040) or 85 (ISIS 459157). The compounds are complementary to the regions 7267-7283, 7270-7286, 7292-7308, 7295-7311, 7316-7332, 7319-7335, 7341-7357, 7344-7360, 7437-7453, 7365-7381, 7368-7384, 7389-7405, 7392-7408, 7416-7432, 7440-7456, 7783-7799, 8133-8152, 8144-8160, 9804-9823, 10718-10734, 15743-15762 of SEQ ID NO: 2. In certain embodiments, the compounds targeting the listed regions, as further described herein, comprise a modified oligonucleotide having some nucleobase portion of the sequence recited in the SEQ ID NOs, as further described herein, In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif, as indicated by the ISIS NOs: 398471, 436140, 448766, 449884, 459014, 459032, 459040, and 459157.

These eight compounds were tested for activity, pharmacokinetic profile and tolerability in cynomolgus monkeys (Example 16). Treatment with some of the compounds caused reduction of GCGR mRNA expression in liver tissue. Specifically, treatment with ISIS 449884, ISIS 459157, and ISIS 325568 caused significant reduction of GCGR mRNA expression in liver tissue, compared to the PBS control. It was noted that ISIS 449884 caused the highest reduction of GCGR mRNA expression compared to the PBS control. Increased glucagon levels are a consequence of inhibition of GCGR mRNA levels. Treatment with ISIS 325568, ISIS 448766, ISIS 459157, and ISIS 449884 caused significant increases in plasma glucagon levels, with ISIS 449884 causing the highest increase. Hence, in terms of activity, ISIS 449884 was the most effective in the monkey study. Treatment with the compounds was well tolerated in the monkeys, in particular, treatment with ISIS 449884.

Accordingly, provided herein are antisense compounds with any one or more of the improved characteristics. In certain embodiments, the compounds as described herein are efficacious by virtue of having at least one of an in vitro $IC_{50}$ of less than 0.1 μM, less than 0.2 μM, less than 0.4 μM, less than 0.35 μM, less than 0.3 μM, less than 2.5 μM, less than 2.0 μM, less than 1.5 μM, less than 1.0 μM, when delivered to a HepG2 cell line using electroporation as described in Examples 8-11. In a certain such embodiments, the compounds are complementary to one or more of the regions 548-567, 2016-2035, and 2018-2037 of SEQ ID NO: 1, and 6682-6698, 7267-7283, 7270-7286, 7292-7308, 7295-7311, 7316-7332, 7317-7333, 7319-7335, 7341-7357, 7344-7360, 7365-7381, 7368-7384, 7389-7405, 7392-7408, 7416-7432, 7437-7453, 7440-7456, 7783-7799, 8030-8049, 8133-8152, 8141-8160, 8144-8160, 9002-9021, 9008-9027, 9245-9264, 9246-9262, 9804-9823, 10676-10695, 10718-10734, 12030-12049, 12031-12050, 12031-12047, 12032-12051, 12033-12052, 12033-12049, 12036-12055, 12175-12194, 12178-12194, 13490-13509, 14138-14157, 15075-15094, 15743-15762, 15744-15763, 15745-15764, and 15746-15765 of SEQ ID NO: 2.

In certain embodiments, the compounds as described herein are highly tolerable, as demonstrated by having at least one of an increase an ALT or AST value of no more than about 100 fold, about 60 fold, about 50 fold, about 40 fold, about 30 fold, about 25 fold, about 10 fold, about 5 fold, about 4 fold, about 3 fold, or about 2 fold over saline treated animals; or an increase in liver, spleen or kidney weight of no more than about 30%, about 20%, about 15%, about 12%, about 10%, about 5% or about 2% as described in the Examples. In certain such embodiments, the compounds are complementary to one or more of the regions 7267-7283, 7270-7286, 7292-7308, 7295-7311, 7316-7332, 7319-7335, 7341-7357, 7344-7360, 7437-7453, 7365-7381, 7368-7384, 7389-7405, 7392-7408, 7416-7432, 7440-7456, 7783-7799, 8133-8152, 8144-8160, 9804-9823, 10718-10734, 15743-15762 of SEQ ID NO: 2

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human Glucagon Receptor (GCGR) in HepG2 Cells

Antisense oligonucleotides were designed targeting a GCGR nucleic acid and were tested for their effects on GCGR mRNA in vitro. ISIS 310457, which was described in an earlier publication (WO 2007/035771) was also tested. Cultured HepG2 cells at a density of 40,000 cells per well were transfected using electroporation with 4,000 nM antisense oligonucleotide. After a treatment period of approximately 24 hours, RNA was isolated from the cells and GCGR mRNA levels were measured by quantitative real-time PCR. Human primer probe set RTS1508 (forward sequence GACACCCCCGCCAATACC, designated herein as SEQ ID NO: 116; reverse sequence CCGCATCTCTTGAACACGAA, designated herein as SEQ ID NO: 117; probe sequence TTGGCACCACAAAGT, designated herein as SEQ ID NO: 118) was used to measure mRNA levels. GCGR mRNA levels were adjusted according to total RNA content, as measured by RIBOGREEN®. Results are presented as percent inhibition of GCGR, relative to untreated control cells. A total of 309 oligonucleotides were tested. Only those oligonucleotides which were selected for dose response assays are shown in Table 1.

The newly designed chimeric antisense oligonucleotides in Table 1 were designed as 3-10-4 MOE gapmers or 5-10-5 MOE gapmers. The 3-10-4 MOE gapmers are 17 nucleosides in length, wherein the central gap segment comprises of ten 2'-deoxynucleosides and is flanked by a wing segment on the 5' direction comprising three nucleosides and by a wing segment on the 3' direction comprising four nucleosides. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 1 is targeted to either the human GCGR mRNA, designated herein as SEQ ID NO: 1 (GENBANK Accession No. NM_000160.3) or the human GCGR genomic sequence, designated herein as SEQ ID NO: 2 (GENBANK Accession No. NW_926918.1 truncated from nucleotides 16865000 to 16885000). 'n/a' indicates that the antisense oligonucleotide does not target that particular gene sequence.

TABLE 1

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 310457 | 548 | 564 | GCACTTTGTGGTGCCAAGGC | 88 | 5-10-5 | n/a | n/a | 4 |
| 449823 | 1098 | 1114 | GCACCCCAGCCGATGCC | 91 | 3-10-4 | n/a | n/a | 5 |
| 450035 | n/a | n/a | AGCCCTGGCCGGTCCTT | 82 | 3-10-4 | 6691 | 6707 | 6 |
| 449881 | n/a | n/a | TCCCGAGGTGCCCAATG | 89 | 3-10-4 | 7267<br>7292<br>7316<br>7341<br>7365<br>7389<br>7437 | 7283<br>7308<br>7332<br>7357<br>7381<br>7405<br>7453 | 7 |
| 449882 | n/a | n/a | TTCCCGAGGTGCCCAAT | 87 | 3-10-4 | 7268<br>7293<br>7317<br>7342<br>7366<br>7390<br>7414<br>7438 | 7284<br>7309<br>7333<br>7358<br>7382<br>7406<br>7430<br>7454 | 8 |
| 398457 | n/a | n/a | GGGTTCCCGAGGTGCCCAAT | 95 | 3-10-4 | 7268<br>7293<br>7317<br>7342<br>7366<br>7390<br>7414<br>7438 | 7287<br>7312<br>7336<br>7361<br>7385<br>7409<br>7433<br>7457 | 9 |

TABLE 1-continued

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 449883 | n/a | n/a | GTTCCCGAGGTGCCCAA | 98 | 3-10-4 | 7269 | 7285 | 10 |
| | | | | | | 7294 | 7310 | |
| | | | | | | 7318 | 7334 | |
| | | | | | | 7343 | 7359 | |
| | | | | | | 7367 | 7383 | |
| | | | | | | 7391 | 7407 | |
| | | | | | | 7415 | 7431 | |
| | | | | | | 7439 | 7455 | |
| 449884 | n/a | n/a | GGTTCCCGAGGTGCCCA | 94 | 3-10-4 | 7270 | 7286 | 11 |
| | | | | | | 7295 | 7311 | |
| | | | | | | 7319 | 7335 | |
| | | | | | | 7344 | 7360 | |
| | | | | | | 7368 | 7384 | |
| | | | | | | 7392 | 7408 | |
| | | | | | | 7416 | 7432 | |
| | | | | | | 7440 | 7456 | |
| 449885 | n/a | n/a | GGGTTCCCGAGGTGCCC | 93 | 3-10-4 | 7271 | 7287 | 12 |
| | | | | | | 7296 | 7312 | |
| | | | | | | 7320 | 7336 | |
| | | | | | | 7345 | 7361 | |
| | | | | | | 7369 | 7385 | |
| | | | | | | 7393 | 7409 | |
| | | | | | | 7417 | 7433 | |
| | | | | | | 7441 | 7457 | |
| 450039 | n/a | n/a | TGATCTCACCCAGCCCT | 88 | 3-10-4 | 7740 | 7756 | 13 |
| 449894 | n/a | n/a | AAGGTGACACCAGCCTG | 92 | 3-10-4 | 7782 | 7798 | 14 |
| 449895 | n/a | n/a | CTGAAGGTGACACCAGC | 90 | 3-10-4 | 7785 | 7801 | 15 |
| 450040 | n/a | n/a | TTCCAGCTGAGCACCCA | 84 | 3-10-4 | 7897 | 7913 | 16 |
| 398471 | n/a | n/a | TCCACAGGCCACAGGTGGGC | 80 | 5-10-5 | 8133 | 8152 | 17 |
| 449905 | n/a | n/a | GCATCCACAGGCCACAG | 85 | 3-10-4 | 8139 | 8155 | 18 |
| 449906 | n/a | n/a | AGCATCCACAGGCCACA | 90 | 3-10-4 | 8140 | 8156 | 19 |
| 449907 | n/a | n/a | CAGCATCCACAGGCCAC | 85 | 3-10-4 | 8141 | 8157 | 20 |
| 449908 | n/a | n/a | CTCAGCATCCACAGGCC | 84 | 3-10-4 | 8143 | 8159 | 21 |
| 449910 | n/a | n/a | AGCCACTGGGAGCACCC | 85 | 3-10-4 | 8386 | 8402 | 22 |
| 449912 | n/a | n/a | GGCTCTGCCCCAACTCT | 82 | 3-10-4 | 8448 | 8464 | 23 |
| 398486 | n/a | n/a | GTGAGCAGCCATGCAGGCTT | 95 | 5-10-5 | 9002 | 9021 | 24 |
| 449916 | n/a | n/a | GAGCAGCCATGCAGGCT | 86 | 3-10-4 | 9003 | 9019 | 25 |
| 449917 | n/a | n/a | TGAGCAGCCATGCAGGC | 90 | 3-10-4 | 9004 | 9020 | 26 |
| 449922 | n/a | n/a | GCCAGGTGAGCAGCCAT | 86 | 3-10-4 | 9010 | 9026 | 27 |
| 450049 | n/a | n/a | AGGGACAGGCACCTGCG | 87 | 3-10-4 | 9130 | 9146 | 28 |
| 450050 | n/a | n/a | GCCTGGATTTTAGCCTC | 84 | 3-10-4 | 9249 | 9265 | 29 |
| 448762 | n/a | n/a | CGGGGTGGCAACAGCTACAC | 80 | 5-10-5 | 9592 | 9611 | 30 |
| 448766 | n/a | n/a | GCAAGGCTCGGTTGGGCTTC | 86 | 5-10-5 | 9804 | 9823 | 31 |
| 450054 | n/a | n/a | TGCAAGGCTCGGTTGGG | 82 | 3-10-4 | 9808 | 9824 | 32 |
| 449759 | 176 | 192 | GCAGAGCAGCAGAGCCT | 80 | 3-10-4 | 10667 | 10683 | 33 |
| 449760 | 177 | 193 | GGCAGAGCAGCAGAGCC | 88 | 3-10-4 | 10668 | 10684 | 34 |

TABLE 1-continued

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 436034 | 185 | 204 | GGCAGCTGAGTGGCAGAGCA | 72 | 5-10-5 | 10676 | 10695 | 35 |
| 450059 | 281 | 297 | GCATGCCTCTGGGCAGC | 88 | 3-10-4 | 10772 | 10788 | 36 |
| 448799 | n/a | n/a | AGGCACAGGCTGAAAGGCTC | 80 | 5-10-5 | 11667 | 11686 | 37 |
| 449938 | n/a | n/a | AGGCCAGGCACAGGCTG | 92 | 3-10-4 | 11675 | 11691 | 38 |
| 448802 | n/a | n/a | GCTGAGGCCAGGCACAGGCT | 87 | 5-10-5 | 11676 | 11695 | 39 |
| 398585 | n/a | n/a | GGCTGCATAAGCACCCAGGA | 87 | 5-10-5 | 11724 | 11743 | 40 |
| 449944 | n/a | n/a | CTGCATAAGCACCCAGG | 84 | 3-10-4 | 11725 | 11741 | 41 |
| 449945 | n/a | n/a | CCCAGCTCTGTGGCTCA | 90 | 3-10-4 | 11819 | 11835 | 42 |
| 448806 | n/a | n/a | GTCCCCAGCTCTGTGGCTCA | 96 | 5-10-5 | 11819 | 11838 | 43 |
| 450061 | n/a | n/a | GCAAGTCCCCAGCTCTG | 91 | 3-10-4 | 11826 | 11842 | 44 |
| 449948 | n/a | n/a | CGCCCTGGCACTGTCTG | 88 | 3-10-4 | 11962 | 11978 | 45 |
| 449949 | n/a | n/a | GTGTCCAGGCCATGATA | 88 | 3-10-4 | 12026 | 12042 | 46 |
| 449951 | n/a | n/a | AAGTGTCCAGGCCATGA | 93 | 3-10-4 | 12028 | 12044 | 47 |
| 398504 | n/a | n/a | CCCAAGTGTCCAGGCCATGA | 91 | 5-10-5 | 12028 | 12047 | 48 |
| 449952 | n/a | n/a | CAAGTGTCCAGGCCATG | 90 | 3-10-4 | 12029 | 12045 | 49 |
| 449953 | n/a | n/a | CCAAGTGTCCAGGCCAT | 91 | 3-10-4 | 12030 | 12046 | 50 |
| 449954 | n/a | n/a | CCCAAGTGTCCAGGCCA | 92 | 3-10-4 | 12031 | 12047 | 51 |
| 448817 | n/a | n/a | CACCCCAAGTGTCCAGGCCA | 98 | 5-10-5 | 12031 | 12050 | 52 |
| 449955 | n/a | n/a | CCCCAAGTGTCCAGGCC | 94 | 3-10-4 | 12032 | 12048 | 53 |
| 449956 | n/a | n/a | ACCCCAAGTGTCCAGGC | 89 | 3-10-4 | 12033 | 12049 | 54 |
| 449958 | n/a | n/a | GCACCCCAAGTGTCCAG | 93 | 3-10-4 | 12035 | 12051 | 55 |
| 448818 | n/a | n/a | CCCTGCACCCCAAGTGTCCA | 83 | 5-10-5 | 12036 | 12055 | 56 |
| 449960 | n/a | n/a | AAACCTGTGGCTGCCAC | 93 | 3-10-4 | 12175 | 12191 | 57 |
| 448819 | n/a | n/a | GCCAAACCTGTGGCTGCCAC | 95 | 5-10-5 | 12175 | 12194 | 58 |
| 449797 | 733 | 749 | GGACAGGCTGTAGCCCA | 83 | 3-10-4 | 13034 | 13050 | 59 |
| 448840 | n/a | n/a | GGCTCACTCCATCACTGAGC | 82 | 5-10-5 | 13314 | 13333 | 60 |
| 449967 | n/a | n/a | CCACCTGCCTGGCTGCC | 89 | 3-10-4 | 13366 | 13382 | 61 |
| 448848 | 1024 | 1043 | GTGCAGGTACAGGCCCTCCA | 92 | 5-10-5 | 13490 | 13509 | 62 |
| 448850 | 1049 | 1068 | GGAGGGTGGCCAGGCCCAGC | 80 | 5-10-5 | 13515 | 13534 | 63 |
| 449819 | 1093 | 1109 | CCAGCCGATGCCCAGGT | 82 | 3-10-4 | 13559 | 13575 | 64 |
| 448860 | n/a | n/a | GGCCAGTGTCCTGGTGTCCT | 79 | 5-10-5 | 14138 | 14157 | 65 |
| 449836 | 1467 | 1483 | GCCACCAGCAGGCCCTG | 87 | 3-10-4 | 14779 | 14795 | 66 |
| 450074 | n/a | n/a | GGGCTGAGGCCAACCTG | 91 | 3-10-4 | 15007 | 15023 | 67 |
| 448890 | n/a | n/a | GCCACCCAGCATCGCCACGG | 86 | 5-10-5 | 15075 | 15094 | 68 |
| 448897 | n/a | n/a | CCCTGCTGGGCACAGCTATG | 83 | 5-10-5 | 15094 | 15113 | 69 |
| 448901 | n/a | n/a | CACAAGCTCCCTGCTGGGCA | 82 | 5-10-5 | 15102 | 15121 | 70 |

TABLE 1-continued

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 448903 | n/a | n/a | GAGCGACACAAGCTCCCTGC | 86 | 5-10-5 | 15108 | 15127 | 71 |
| 448905 | n/a | n/a | GGTGCAGAGCGACACAAGCT | 81 | 5-10-5 | 15114 | 15133 | 72 |
| 449851 | 1646 | 1662 | GGCTGCCACCACCCCTC | 88 | 3-10-4 | 15374 | 15390 | 73 |
| 449856 | 2016 | 2032 | CTTTATTGTTGGAGGAC | 85 | 3-10-4 | 15744 | 15760 | 74 |
| 449858 | 2018 | 2034 | CTCTTTATTGTTGGAGG | 85 | 3-10-4 | 15746 | 15762 | 75 |
| 449859 | 2019 | 2035 | GCTCTTTATTGTTGGAG | 91 | 3-10-4 | 15747 | 15763 | 76 |
| 449860 | 2020 | 2036 | AGCTCTTTATTGTTGGA | 88 | 3-10-4 | 15748 | 15764 | 77 |
| 449861 | 2021 | 2037 | GAGCTCTTTATTGTTGG | 81 | 3-10-4 | 15749 | 15765 | 78 |

Example 2

Antisense Inhibition of Human Glucagon Receptor (GCGR) in HepG2 Cells

Additional antisense oligonucleotides were designed to target a GCGR nucleic acid and were tested for their effects on GCGR mRNA in vitro. ISIS 315163 (ACCTGGAAGCTGCTGTACAT (SEQ ID NO 79); start site on SEQ ID NO: 1 is 702; start site on SEQ ID NO: 2 is 13003), which was described in an earlier publication (WO 2004/096016) was also tested. Cultured HepG2 cells at a density of 40,000 cells per well were transfected using electroporation with 1,000 nM antisense oligonucleotide. After a treatment period of approximately 24 hours, RNA was isolated from the cells and GCGR mRNA levels were measured by quantitative real-time PCR using human primer probe set RTS1508. GCGR mRNA levels were adjusted according to total RNA content, as measured by RIBOGREEN®. Results are presented as percent inhibition of GCGR, relative to untreated control cells. A total of 156 antisense oligonucleotides were tested. Only those oligonucleotides which were selected for dose response assays are shown in Table 2.

The newly designed chimeric antisense oligonucleotides in Table 2 were designed as 3-10-3 MOE, 3-10-4 MOE 4-10-4 MOE, 4-10-5 MOE, or 5-10-6 MOE gapmers. The 3-10-3 MOE gapmers are 16 nucleosides in length, wherein the central gap segment comprises of ten 2'-deoxynucleosides and is flanked by wing segments on the 5' direction and the 3' direction comprising three nucleosides each. The 3-10-4 MOE gapmers are 17 nucleosides in length, wherein the central gap segment comprises of ten 2'-deoxynucleosides and is flanked by a wing segment on the 5' direction comprising three nucleosides and by a wing segment on the 3' direction comprising four nucleosides. The 4-10-4 MOE gapmers are 18 nucleosides in length, wherein the central gap segment comprises of ten 2'-deoxynucleosides and is flanked by wing segments on the 5' direction and the 3' direction comprising four nucleosides each. The 4-10-5 MOE gapmers are 19 nucleosides in length, wherein the central gap segment comprises of ten 2'-deoxynucleosides and is flanked by a wing segment on the 5' direction comprising four nucleosides and by a wing segment on the 3' direction comprising five nucleosides. The 5-10-6 MOE gapmers are 21 nucleosides in length, wherein the central gap segment comprises of ten 2'-deoxynucleosides and is flanked by a wing segment on the 5' direction comprising five nucleosides and by a wing segment on the 3' direction comprising six nucleosides. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted in the human gene sequence. Each gapmer listed in Table 2 is targeted to either the human GCGR mRNA, designated herein as SEQ ID NO: 1 (GENBANK Accession No. NM_000160.3) or the human GCGR genomic sequence, designated herein as SEQ ID NO: 2 (GENBANK Accession No. NW_926918.1 truncated from nucleotides 16865000 to 16885000). 'n/a' indicates that the antisense oligonucleotide does not target that particular gene sequence.

TABLE 2

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 315163 | 702 | 721 | ACCTGGAAGCTGCTGTACAT | 38 | 5-10-5 | 13003 | 13022 | 79 |
| 459014 | 227 | 243 | GGGCAATGCAGTCCTGG | 62 | 3-10-4 | 10718 | 10734 | 80 |

TABLE 2-continued

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 459032 | n/a | n/a | GAAGGTGACACCAGCCT | 83 | 3-10-4 | 7783 | 7799 | 81 |
| 459040 | n/a | n/a | GCTCAGCATCCACAGGC | 63 | 3-10-4 | 8144 | 8160 | 82 |
| 459046 | n/a | n/a | TGGATTTTAGCCTCCTC | 73 | 3-10-4 | 9246 | 9262 | 83 |
| 459076 | n/a | n/a | GCCAAACCTGTGGCTGC | 84 | 3-10-4 | 12178 | 12194 | 84 |
| 459157 | n/a | n/a | GGGTTCCCGAGGTGCCCAATG | 92 | 5-10-6 | 7267<br>7292<br>7316<br>7341<br>7365<br>7389<br>7437 | 7287<br>7312<br>7336<br>7361<br>7385<br>7409<br>7457 | 85 |
| 459010 | n/a | n/a | GGTTCCCGAGGTGCCC | 100 | 3-10-3 | 7271<br>7296<br>7320<br>7345<br>7369<br>7393<br>7417<br>7441 | 7286<br>7311<br>7335<br>7360<br>7384<br>7408<br>7432<br>7456 | 86 |
| 459011 | n/a | n/a | GGGTTCCCGAGGTGCC | 89 | 3-10-3 | 7272<br>7297<br>7321<br>7346<br>7370<br>7394<br>7418<br>7442 | 7287<br>7312<br>7336<br>7361<br>7385<br>7409<br>7433<br>7457 | 87 |
| 459058 | n/a | n/a | GAGGCCAGGCACAGGCT | 75 | 3-10-4 | 11676 | 11692 | 88 |
| 459024 | n/a | n/a | CGGTCCTTGGAGGATGC | 63 | 3-10-4 | 6682 | 6698 | 89 |
| 459088 | n/a | n/a | GTTCCCGAGGTGCCCAATG | 89 | 4-10-5 | 7267<br>7292<br>7316<br>7341<br>7365<br>7389<br>7437 | 7285<br>7310<br>7334<br>7359<br>7383<br>7407<br>7455 | 90 |
| 459087 | n/a | n/a | GGTTCCCGAGGTGCCCAAT | 95 | 4-10-5 | 7268<br>7293<br>7317<br>7342<br>7366<br>7390<br>7414<br>7438 | 7286<br>7311<br>7335<br>7360<br>7384<br>7408<br>7432<br>7456 | 91 |
| 459086 | n/a | n/a | GGGTTCCCGAGGTGCCCAA | 96 | 4-10-5 | 7269<br>7294<br>7318<br>7343<br>7367<br>7391<br>7415<br>7439 | 7287<br>7312<br>7336<br>7361<br>7385<br>7409<br>7433<br>7457 | 92 |
| 459083 | n/a | n/a | GGTTCCCGAGGTGCCCAA | 91 | 4-10-4 | 7269<br>7294<br>7318<br>7343<br>7367<br>7391<br>7415<br>7439 | 7286<br>7311<br>7335<br>7360<br>7384<br>7408<br>7432<br>7456 | 93 |

TABLE 2-continued

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 459009 | n/a | n/a | GTTCCCGAGGTGCCCA | 61 | 3-10-3 | 7270 | 7285 | 94 |
| | | | | | | 7295 | 7310 | |
| | | | | | | 7319 | 7334 | |
| | | | | | | 7344 | 7359 | |
| | | | | | | 7368 | 7383 | |
| | | | | | | 7392 | 7407 | |
| | | | | | | 7416 | 7431 | |
| | | | | | | 7440 | 7455 | |
| 459082 | n/a | n/a | GGGTTCCCGAGGTGCCCA | 91 | 4-10-4 | 7270 | 7287 | 95 |
| | | | | | | 7295 | 7312 | |
| | | | | | | 7319 | 7336 | |
| | | | | | | 7344 | 7361 | |
| | | | | | | 7368 | 7385 | |
| | | | | | | 7392 | 7409 | |
| | | | | | | 7416 | 7433 | |
| | | | | | | 7440 | 7457 | |
| 459158 | n/a | n/a | GGGTTCCCGAGGTGCCCAATA | 94 | 5-10-6 | 7413 | 7433 | 96 |
| 459063 | n/a | n/a | CCAGCTCTGTGGCTCAG | 62 | 3-10-4 | 11818 | 11834 | 97 |

Example 3

Antisense Inhibition of Human Glucagon Receptor (GCGR) in HepG2 Cells

Additional antisense oligonucleotides were designed targeting a GCGR nucleic acid and were tested for their effects on GCGR mRNA in vitro. ISIS 315163 was also tested. ISIS 325568, which has been described in a previous publication (WO 2007/035771) was also tested. Cultured HepG2 cells at a density of 40,000 cells per well were transfected using electroporation with 2,000 nM antisense oligonucleotide. After a treatment period of approximately 24 hours, RNA was isolated from the cells and GCGR mRNA levels were measured by quantitative real-time PCR using human primer probe set RTS1508. GCGR mRNA levels were adjusted according to total RNA content, as measured by RIBOGREEN®. Results are presented as percent inhibition of GCGR, relative to untreated control cells. A total of 78 antisense oligonucleotides were tested. Only those oligonucleotides which were selected for dose response assays are shown in Table 3.

The newly designed chimeric antisense oligonucleotides in Table 3 were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 3 is targeted to either the human GCGR mRNA, designated herein as SEQ ID NO: 1 (GENBANK Accession No. NM_000160.3) or the human GCGR genomic sequence, designated herein as SEQ ID NO: 2 (GENBANK Accession No. NW_926918.1 truncated from nucleotides 16865000 to 16885000). 'n/a' indicates that the antisense oligonucleotide does not target that particular gene sequence.

TABLE 3

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 315163 | 702 | 721 | ACCTGGAAGCTGCTGTACAT | 42 | 5-10-5 | 13003 | 13022 | 79 |
| 325568 | 548 | 567 | GCACTTTGTGGTGCCAAGGC | 58 | 2-16-2 | n/a | n/a | 4 |
| 448754 | n/a | n/a | CCTGGATTTAGCCTCCTCC | 79 | 5-10-5 | 9245 | 9264 | 98 |

TABLE 3-continued

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 448718 | n/a | n/a | TGGGTCTCTGATAGTGAGGC | 81 | 5-10-5 | 8030 | 8049 | 99 |
| 448730 | n/a | n/a | GCTCAGCATCCACAGGCCAC | 74 | 5-10-5 | 8141 | 8160 | 100 |
| 448738 | n/a | n/a | GCCAAGCCTGGCTCTGCCCC | 76 | 5-10-5 | 8454 | 8473 | 101 |

Example 4

Antisense Inhibition of Human Glucagon Receptor (GCGR) in HepG2 Cells

Additional antisense oligonucleotides were designed targeting a GCGR nucleic acid and were tested for their effects on GCGR mRNA in vitro. ISIS 315163 and ISIS 325568 were also tested. Cultured HepG2 cells at a density of 40,000 cells per well were transfected using electroporation with 5,000 nM antisense oligonucleotide. After a treatment period of approximately 24 hours, RNA was isolated from the cells and GCGR mRNA levels were measured by quantitative real-time PCR using human primer probe set RTS1508. GCGR mRNA levels were adjusted according to total RNA content, as measured by RIBOGREEN®. Results are presented as percent inhibition of GCGR, relative to untreated control cells. A total of 234 antisense oligonucleotides were tested. Only those oligonucleotides which were selected for dose response assays are shown in Table 4.

The newly designed chimeric antisense oligonucleotides in Table 4 were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. “Start site” indicates the 5'-most nucleoside to which the gapmer is targeted in the human gene sequence. “Stop site” indicates the 3'-most nucleoside to which the gapmer is targeted human gene sequence. Each gapmer listed in Table 4 is targeted to either the human GCGR mRNA, designated herein as SEQ ID NO: 1 (GENBANK Accession No. NM_000160.3) or the human GCGR genomic sequence, designated herein as SEQ ID NO: 2 (GENBANK Accession No. NW_926918.1 truncated from nucleotides 16865000 to 16885000). ‘n/a’ indicates that the antisense oligonucleotide does not target that particular gene sequence.

TABLE 4

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 315163 | 702 | 721 | AC CTGGAAGCTGCTGTACAT | 71 | 5-10-5 | 13003 | 13022 | 79 |
| 325568 | 548 | 567 | GCACTTTGTGGTGCCAAGGC | 79 | 2-16-2 | n/a | n/a | 4 |
| 436140 | 2015 | 2034 | CTCTTTATTGTTGGAGGACA | 93 | 5-10-5 | 15743 | 15762 | 102 |
| 398455 | 2014 | 2033 | TCTTTATTGTTGGAGGACAT | 89 | 5-10-5 | 15742 | 15761 | 103 |
| 398470 | n/a | n/a | CCACAGGCCACAGGTGGGCT | 85 | 5-10-5 | 8132 | 8151 | 104 |
| 398491 | n/a | n/a | AGCCAGGTGAGCAGCCATGC | 81 | 5-10-5 | 9008 | 9027 | 105 |
| 398501 | n/a | n/a | AAGTGTCCAGGCCATGATAT | 84 | 5-10-5 | 12025 | 12044 | 106 |
| 398503 | n/a | n/a | CCAAGTGTCCAGGCCATGAT | 92 | 5-10-5 | 12027 | 12046 | 107 |
| 398506 | n/a | n/a | ACCCCAAGTGTCCAGGCCAT | 89 | 5-10-5 | 12030 | 12049 | 108 |
| 398507 | n/a | n/a | GCACCCCAAGTGTCCAGGCC | 97 | 5-10-5 | 12032 | 12051 | 109 |
| 398508 | n/a | n/a | TGCACCCCAAGTGTCCAGGC | 87 | 5-10-5 | 12033 | 12052 | 110 |
| 304535 | 1988 | 2007 | GCACATGGGACGTGCCGACA | 98 | 5-10-5 | 15716 | 15735 | 111 |
| 304538 | 2016 | 2035 | GCTCTTTATTGTTGGAGGAC | 95 | 5-10-5 | 15744 | 15763 | 112 |
| 304539 | 2018 | 2037 | GAGCTCTTTATTGTTGGAGG | 92 | 5-10-5 | 15746 | 15765 | 113 |

TABLE 4-continued

Inhibition of human GCGR mRNA levels by chimeric antisense oligonucleotides targeted to SEQ ID NO: 1 and SEQ ID NO: 2

| ISIS NO | SEQ ID NO: 1 Start Site | SEQ ID NO: 1 Stop Site | Sequence | % inhibition | Motif | SEQ ID NO: 2 Start Site | SEQ ID NO: 2 Stop Site | SEQ ID NO |
|---|---|---|---|---|---|---|---|---|
| 436141 | 2017 | 2036 | AGCTCTTTATTGTTGGAGGA | 93 | 5-10-5 | 15745 | 15764 | 114 |
| 436164 | n/a | n/a | GGTTCCCGAGGTGCCCAATG | 92 | 5-10-5 | 7267 | 7286 | 115 |
| | | | | | | 7292 | 7311 | |
| | | | | | | 7316 | 7335 | |
| | | | | | | 7341 | 7360 | |
| | | | | | | 7365 | 7384 | |
| | | | | | | 7389 | 7408 | |
| | | | | | | 7437 | 7456 | |

Example 5

Dose-Dependent Antisense Inhibition of Human GCGR in Cynomolgus Primary Hepatocytes Gapmers from Example 1 exhibiting significant in vitro inhibition of human GCGR were tested under various conditions in cynomolgus primary hepatocytes. Cells were plated at a density of 24,000 cells per well and transfected using electroporation with 0.4 μM, 1.1 μM, 3.3 μM, and 10.0 μM concentrations of antisense oligonucleotide, as specified in Table 5. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells.

The half maximal inhibitory concentration ($IC_{50}$) of each oligonucleotide is also presented in Table 5 and was calculated by plotting the concentrations of oligonucleotides used versus the percent inhibition of GCGR mRNA expression achieved at each concentration, and noting the concentration of oligonucleotide at which 50% inhibition of GCGR mRNA expression was achieved compared to the control. As illustrated in Table 5, GCGR mRNA levels were significantly reduced in a dose-dependent manner in antisense oligonucleotide treated cells.

TABLE 5

Dose-dependent antisense inhibition of human GCGR in cynomolgus primary hepatocytes using electroporation

| ISIS No | 0.4 μM | 1.1 μM | 3.3 μM | 10.0 μM | $IC_{50}$ (μM) |
|---|---|---|---|---|---|
| 315163 | 23 | 39 | 73 | 88 | 2.0 |
| 398457 | 64 | 69 | 71 | 68 | <0.3 |
| 449759 | 24 | 47 | 75 | 85 | 1.3 |
| 449760 | 43 | 49 | 77 | 86 | 0.7 |
| 449797 | 38 | 54 | 69 | 93 | 0.8 |
| 449819 | 30 | 36 | 56 | 85 | 1.7 |
| 449823 | 29 | 31 | 43 | 82 | 2.5 |
| 449836 | 29 | 37 | 62 | 85 | 1.6 |
| 449851 | 14 | 36 | 73 | 93 | 1.6 |
| 449856 | 0 | 39 | 70 | 88 | 2.1 |
| 449858 | 16 | 27 | 65 | 86 | 2.1 |
| 449859 | 57 | 76 | 92 | 96 | <0.3 |
| 449860 | 41 | 66 | 86 | 91 | 0.5 |

TABLE 5-continued

Dose-dependent antisense inhibition of human GCGR in cynomolgus primary hepatocytes using electroporation

| ISIS No | 0.4 μM | 1.1 μM | 3.3 μM | 10.0 μM | $IC_{50}$ (μM) |
|---|---|---|---|---|---|
| 449881 | 27 | 49 | 67 | 70 | 1.5 |
| 449882 | 33 | 33 | 53 | 71 | 2.3 |
| 449883 | 63 | 66 | 75 | 76 | <0.3 |
| 449884 | 64 | 77 | 74 | 71 | <0.3 |
| 449885 | 67 | 74 | 71 | 76 | <0.3 |
| 449894 | 55 | 56 | 74 | 78 | <0.3 |
| 449895 | 44 | 60 | 71 | 72 | 0.5 |
| 449905 | 47 | 59 | 65 | 69 | 0.4 |
| 449906 | 52 | 66 | 75 | 80 | <0.3 |
| 449907 | 35 | 36 | 62 | 70 | 1.8 |
| 449908 | 21 | 48 | 67 | 69 | 1.8 |
| 449910 | 7 | 16 | 51 | 61 | 4.8 |
| 449912 | 21 | 45 | 66 | 60 | 2.3 |
| 449916 | 16 | 40 | 55 | 55 | 3.9 |
| 449917 | 45 | 67 | 72 | 71 | 0.3 |
| 449922 | 39 | 48 | 60 | 67 | 1.3 |
| 449938 | 5 | 22 | 44 | 41 | >10.0 |
| 449944 | 6 | 0 | 25 | 62 | 7.0 |
| 449945 | 22 | 36 | 57 | 64 | 2.8 |
| 449948 | 0 | 19 | 45 | 60 | 5.2 |
| 449949 | 0 | 16 | 41 | 52 | 7.8 |
| 449951 | 26 | 40 | 55 | 61 | 2.9 |
| 449952 | 21 | 28 | 52 | 62 | 3.8 |
| 449953 | 15 | 22 | 49 | 59 | 4.8 |
| 449954 | 0 | 53 | 60 | 58 | 3.4 |
| 449955 | 30 | 43 | 61 | 66 | 1.9 |
| 449956 | 10 | 40 | 52 | 64 | 3.3 |
| 449958 | 17 | 46 | 54 | 67 | 2.6 |
| 449960 | 10 | 22 | 46 | 63 | 4.7 |
| 449967 | 0 | 16 | 36 | 49 | 9.8 |
| 450035 | 0 | 35 | 41 | 60 | 5.0 |
| 450039 | 18 | 30 | 51 | 60 | 4.2 |
| 450040 | 0 | 21 | 41 | 66 | 4.7 |
| 450049 | 22 | 27 | 59 | 68 | 2.9 |
| 450050 | 28 | 22 | 49 | 61 | 4.7 |
| 450054 | 0 | 11 | 22 | 25 | >10.0 |
| 450059 | 11 | 41 | 64 | 78 | 2.1 |
| 450061 | 13 | 29 | 49 | 60 | 4.4 |
| 450074 | 15 | 27 | 40 | 61 | 5.4 |

Example 6

Dose-Dependent Antisense Inhibition of Human GCGR in HepG2 Cells

Gapmers from Example 5 exhibiting significant in vitro inhibition of GCGR mRNA were selected and tested at various doses in HepG2 cells. Cells were plated at a density of 40,000 cells per well and transfected using electroporation with 0.12 μM, 0.37 μM, 1.11 μM, 3.33 μM and 10.00 μM concentrations of antisense oligonucleotide, as specified in Table 6. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells.

The half maximal inhibitory concentration ($IC_{50}$) of each oligonucleotide is also presented in Table 6. As illustrated in Table 6, GCGR mRNA levels were significantly reduced in a dose-dependent manner in antisense oligonucleotide treated cells.

TABLE 6

Dose-dependent antisense inhibition of human GCGR in HepG2 cells using electroporation

| ISIS No | 0.12 μM | 0.37 μM | 1.11 μM | 3.33 μM | 10.00 μM | $IC_{50}$ (μM) |
|---|---|---|---|---|---|---|
| 315163 | 0 | 3 | 26 | 62 | 88 | 2.2 |
| 398457 | 47 | 81 | 94 | 97 | 97 | <0.1 |
| 449760 | 0 | 26 | 64 | 91 | 97 | 0.8 |
| 449797 | 0 | 16 | 42 | 84 | 95 | 1.2 |
| 449819 | 0 | 17 | 40 | 79 | 93 | 1.3 |
| 449851 | 4 | 28 | 65 | 94 | 97 | 0.7 |
| 449859 | 36 | 51 | 89 | 95 | 95 | 0.2 |
| 449860 | 30 | 53 | 77 | 86 | 94 | 0.3 |
| 449882 | 0 | 19 | 57 | 85 | 97 | 1.0 |
| 449883 | 7 | 49 | 84 | 92 | 96 | 0.5 |
| 449884 | 67 | 87 | 95 | 94 | 97 | <0.1 |
| 449885 | 44 | 83 | 77 | 97 | 95 | <0.1 |
| 449894 | 1 | 34 | 78 | 87 | 98 | 0.7 |
| 449895 | 0 | 31 | 29 | 84 | 95 | 1.1 |
| 449906 | 12 | 26 | 67 | 93 | 95 | 0.7 |

Example 7

Dose-Dependent Antisense Inhibition of Human GCGR in HepG2 Cells

Gapmers from Example 5 exhibiting significant in vitro inhibition of GCGR mRNA were further selected and tested at various doses in HepG2 cells. Cells were plated at a density of 40,000 cells per well and transfected using electroporation with 0.04 μM, 0.12 μM, 0.37 μM, 1.11 μM, 3.33 μM and 10.00 μM concentrations of antisense oligonucleotide, as specified in Table 7. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells.

The half maximal inhibitory concentration ($IC_{50}$) of each oligonucleotide is also presented in Table 7.

GCGR mRNA levels were significantly reduced in a dose-dependent manner in antisense oligonucleotide treated cells. 'n/a' denotes that there is no data for that ISIS oligonucleotide for that particular concentration. ISIS 398457, ISIS 449884, and ISIS 449954, which caused significant reduction of GCGR mRNA levels, were selected for further studies. Significantly, ISIS 449884 demonstrated an $IC_{50}$ ten to fifty times lower than the benchmark ISIS 315163 in head-to-head studies presented in Examples 5-7.

TABLE 7

Dose-dependent antisense inhibition of human GCGR in HepG2 cells using electroporation

| ISIS No | 0.04 μM | 0.12 μM | 0.37 μM | 1.11 μM | 3.33 μM | 10.00 μM | $IC_{50}$ (μM) |
|---|---|---|---|---|---|---|---|
| 315163 | 22 | 9 | 22 | 45 | 67 | 93 | 1.5 |
| 398457 | 36 | 62 | 88 | 99 | 99 | 100 | 0.1 |
| 449856 | 8 | 24 | 49 | 73 | 92 | 95 | 0.4 |
| 449858 | 28 | 27 | 41 | 80 | 93 | 97 | 0.3 |
| 449859 | 16 | 40 | 72 | 89 | 97 | 98 | 0.2 |
| 449860 | 32 | 38 | 46 | 78 | 94 | 98 | 0.2 |
| 449883 | 25 | 27 | 68 | 92 | 98 | 100 | 0.2 |
| 449884 | 42 | 59 | 93 | 99 | 100 | n/a | <0.04 |
| 449885 | 18 | 60 | 84 | 97 | 98 | n/a | 0.1 |
| 449894 | 8 | 31 | 44 | 83 | 96 | 99 | 0.3 |
| 449951 | 0 | 32 | 62 | 86 | 98 | 99 | 0.4 |
| 449954 | 9 | 40 | 57 | 86 | 99 | 99 | 0.2 |

Example 8

Dose-Dependent Antisense Inhibition of Human GCGR in Cynomolgus Primary Hepatocytes Gapmers from studies described in Examples 1-7 were further tested at various doses in cynomolgus primary hepatocytes. Cells were plated at a density of 35,000 cells per well and transfected using electroporation with 750 nM, 1,500 nM, 3,000 nM, 6,000 nM, and 12,000 nM concentrations of antisense oligonucleotide, as specified in Table 8. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells. As illustrated in Table 8, GCGR mRNA levels were significantly reduced in antisense oligonucleotide treated cells.

TABLE 8

Dose-dependent antisense inhibition of human GCGR in cynomolgus primary hepatocytes using electroporation

| ISIS No | 750.0 nM | 1500.0 nM | 3000.0 nM | 6000.0 nM | 12000.0 nM |
|---|---|---|---|---|---|
| 398457 | 85 | 89 | 92 | 89 | 85 |
| 398471 | 78 | 85 | 87 | 85 | 87 |
| 436140 | 81 | 93 | 96 | 97 | 96 |
| 448754 | 44 | 59 | 80 | 80 | 81 |
| 448766 | 79 | 90 | 88 | 87 | 83 |
| 448818 | 19 | 13 | 58 | 64 | 76 |
| 449884 | 89 | 92 | 89 | 87 | 90 |
| 459014 | 51 | 63 | 79 | 82 | 84 |
| 459032 | 78 | 85 | 88 | 88 | 87 |
| 459040 | 70 | 77 | 81 | 89 | 83 |
| 459046 | 34 | 38 | 65 | 61 | 80 |
| 459076 | 31 | 39 | 67 | 79 | 77 |
| 459157 | 89 | 87 | 88 | 88 | 86 |

Example 9

Dose-Dependent Antisense Inhibition of Human GCGR in Cynomolgus Primary Hepatocytes Gapmers from Example 8 exhibiting significant in vitro inhibition of human GCGR were further selected and tested at various doses in cynomolgus primary hepatocytes. ISIS 325568 (GCACTTTGTGGTGCCAAGGC (SEQ ID NO: 4), target start site 548 on SEQ ID NO: 1), which was described in an earlier publication (BIOL066USL) was also tested. Cells were plated at a density of 35,000 cells per well and transfected using electroporation with 0.006 μM, 0.020 μM, 0.063 μM, 0.200 μM, 0.632 μM, 2.000 μM, 6.325 μM, and 20.000 μM concentrations of antisense oligonucleotide, as specified in Table 9. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells.

The half maximal inhibitory concentration ($IC_{50}$) of each oligonucleotide is also presented in Table 9. GCGR mRNA levels were significantly reduced in a dose-dependent manner in antisense oligonucleotide treated cells.

TABLE 9

Dose-dependent antisense inhibition of human GCGR in cynomolgus primary hepatocytes using electroporation

| ISIS No | 0.006 μM | 0.020 μM | 0.063 μM | 0.200 μM | 0.632 μM | 2.000 μM | 6.325 μM | 20.000 μM | $IC_{50}$ (μM) |
|---|---|---|---|---|---|---|---|---|---|
| 325568 | 0 | 0 | 0 | 0 | 0 | 42 | 75 | 93 | 3.1 |
| 398471 | 0 | 4 | 7 | 24 | 62 | 65 | 65 | 59 | 0.4 |
| 448766 | 5 | 0 | 0 | 2 | 28 | 51 | 57 | 34 | 0.6 |
| 449884 | 0 | 12 | 61 | 59 | 71 | 68 | 72 | 62 | 0.1 |
| 459014 | 1 | 0 | 2 | 23 | 15 | 47 | 69 | 74 | 2.6 |
| 459032 | 0 | 6 | 4 | 33 | 55 | 68 | 72 | 61 | 0.5 |
| 459157 | 0 | 12 | 29 | 69 | 69 | 72 | 73 | 62 | 0.1 |

Based on the inhibition data, ISIS 398471, ISIS 448766, ISIS 449884, ISIS 459014, ISIS 459032, and ISIS 459157 were selected for in vivo testing in a mouse model.

TABLE 10

Dose-dependent antisense inhibition of human GCGR in HepG2 cells using electroporation

| ISIS No | 0.12 μM | 0.37 μM | 1.11 μM | 3.33 μM | 10.00 μM | $IC_{50}$ (μM) |
|---|---|---|---|---|---|---|
| 398455 | 35 | 57 | 81 | 94 | 94 | 0.2 |
| 398457 | 33 | 79 | 91 | 97 | 98 | 0.1 |
| 398470 | 37 | 48 | 86 | 92 | 96 | 0.2 |
| 398471 | 33 | 50 | 86 | 92 | 87 | 0.2 |
| 398486 | 50 | 47 | 85 | 91 | 98 | 0.1 |
| 398491 | 25 | 61 | 73 | 96 | 92 | 0.3 |
| 398501 | 35 | 43 | 85 | 98 | 98 | 0.3 |
| 398503 | 21 | 58 | 80 | 97 | 99 | 0.3 |
| 398504 | 51 | 57 | 91 | 92 | 98 | 0.1 |
| 398506 | 40 | 71 | 96 | 98 | 99 | 0.1 |
| 398507 | 59 | 85 | 97 | 98 | n/a | <0.1 |
| 398508 | 22 | 48 | 90 | 94 | 98 | 0.3 |
| 398585 | 25 | 57 | 84 | 88 | 93 | 0.3 |
| 436034 | 34 | 56 | 61 | 81 | 92 | 0.3 |

Based on the inhibition results, ISIS 398457, ISIS 398471, ISIS 398486, ISIS 398491, ISIS 398506, ISIS 398507, ISIS 398508, and ISIS 436034 were selected for testing in a mouse model.

Example 10

Dose-Dependent Antisense Inhibition of Human GCGR in HepG2 Cells

Gapmers from studies described in Examples 1, 4, and 9 were further tested at various doses in HepG2 cells. Cells were plated at a density of 40,000 cells per well and transfected using electroporation with 0.12 μM, 0.37 μM, 1.11 μM, 3.33 μM, and 10.00 μM concentrations of antisense oligonucleotide, as specified in Table 10. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells. As illustrated in Table 10, GCGR mRNA levels were significantly reduced in antisense oligonucleotide treated cells.

Example 11

Dose-Dependent Antisense Inhibition of Human GCGR in HepG2 Cells

Gapmers from the study described in Example 4 were further tested at various doses in HepG2 cells. Cells were plated at a density of 40,000 cells per well and transfected using electroporation with 0.04 μM, 0.12 μM, 0.37 μM, 1.11 μM, 3.33 μM, and 10.00 μM concentrations of antisense oligonucleotide, as specified in Table 11. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells. GCGR mRNA levels were significantly reduced in antisense oligonucleotide treated cells.

TABLE 11

| Dose-dependent antisense inhibition of human GCGR in HepG2 cells using electroporation | | | | | | | |
|---|---|---|---|---|---|---|---|
| ISIS No | 0.04 μM | 0.12 μM | 0.37 μM | 1.11 μM | 3.33 μM | 10.00 μM | $IC_{50}$ (μM) |
| 304535 | 21 | 31 | 55 | 90 | 99 | 96 | 0.2 |
| 304538 | 27 | 42 | 73 | 91 | 100 | 95 | 0.1 |
| 304539 | 15 | 33 | 56 | 87 | 95 | 93 | 0.3 |
| 436140 | 4 | 27 | 57 | 85 | 94 | 95 | 0.3 |
| 436141 | 19 | 27 | 64 | 84 | 92 | 95 | 0.3 |
| 436164 | 12 | 37 | 75 | 94 | 94 | 96 | 0.2 |

Based on the inhibition results, ISIS 304538, ISIS 304539, ISIS 436140 and ISIS 436141 were selected for testing in a mouse model.

Example 12

Dose-Dependent Antisense Inhibition of Human GCGR in HepG2 Cells

Gapmers from the study described in Examples 1, 3, 8 and 9 were further tested at various doses in HepG2 cells. Cells were plated at a density of 40,000 cells per well and transfected using electroporation with 0.12 μM, 0.37 μM, 1.11 μM, 3.33 μM, and 10.00 μM concentrations of antisense oligonucleotide, as specified in Table 12. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells. GCGR mRNA levels were significantly reduced in antisense oligonucleotide treated cells.

TABLE 12

| Dose-dependent antisense inhibition of human GCGR in HepG2 cells using electroporation | | | | | | |
|---|---|---|---|---|---|---|
| ISIS No | 0.12 μM | 0.37 μM | 1.11 μM | 3.33 μM | 10.00 μM | $IC_{50}$ (μM) |
| 448718 | 35 | 64 | 74 | 90 | 92 | 0.2 |
| 448730 | 44 | 67 | 87 | 94 | 85 | 0.1 |
| 448738 | 31 | 52 | 75 | 95 | 97 | 0.3 |
| 448754 | 40 | 47 | 81 | 95 | 96 | 0.3 |
| 448762 | 43 | 62 | 75 | 96 | 97 | 0.2 |
| 448766 | 36 | 59 | 88 | 94 | 85 | 0.2 |
| 448799 | 42 | 53 | 92 | 96 | 99 | 0.2 |
| 448802 | 43 | 70 | 88 | 97 | 93 | 0.1 |
| 448806 | 39 | 60 | 82 | 97 | 96 | 0.2 |
| 448817 | 35 | 62 | 95 | 88 | 92 | 0.2 |
| 448818 | 29 | 52 | 74 | 97 | 98 | 0.3 |
| 448819 | 73 | 89 | 97 | n/a | 93 | <0.1 |
| 448840 | 31 | 58 | 80 | 83 | 98 | 0.3 |
| 448848 | 71 | 92 | 98 | 98 | 99 | <0.1 |
| 448850 | 54 | 60 | 74 | 88 | 94 | <0.1 |
| 448860 | 41 | 58 | 73 | 92 | 98 | 0.2 |
| 448890 | 49 | 60 | 83 | 94 | 99 | 0.1 |
| 448897 | 50 | 52 | 80 | 92 | 97 | 0.2 |
| 448901 | 29 | 58 | 81 | 91 | 99 | 0.3 |
| 448903 | 32 | 48 | 73 | 91 | 99 | 0.3 |
| 448905 | 43 | 49 | 76 | 89 | 97 | 0.2 |

Based on the inhibition results, ISIS 448718, ISIS 448730, ISIS 448754, ISIS 448766, ISIS 448817, ISIS 448818, ISIS 448819, ISIS 448848, ISIS 448860, and ISIS 448890 were selected for testing in a mouse model.

Example 13

Dose-Dependent Antisense Inhibition of Human GCGR in HepG2 Cells

Gapmers from the study described in Examples 1, 2, 8, and 9 were further tested at various doses in HepG2 cells. Cells were plated at a density of 40,000 cells per well and transfected using electroporation with 0.12 μM, 0.37 μM, 1.11 μM, 3.33 μM, and 10.00 μM concentrations of antisense oligonucleotide, as specified in Table 13. After a treatment period of approximately 16 hours, RNA was isolated from the cells and GCGR mRNA levels were measured by quantitative real-time PCR. Human GCGR primer probe set RTS1508 was used to measure mRNA levels. GCGR mRNA levels were adjusted according to total RNA content, as measured by RIBOGREEN®. Results are presented as percent inhibition of GCGR, relative to untreated control cells. GCGR mRNA levels were significantly reduced in antisense oligonucleotide treated cells.

TABLE 13

| Dose-dependent antisense inhibition of human GCGR in HepG2 cells using electroporation | | | | | | |
|---|---|---|---|---|---|---|
| ISIS No | 0.12 μM | 0.37 μM | 1.11 μM | 3.33 μM | 10.00 μM | $IC_{50}$ (μM) |
| 398457 | 62 | 84 | 95 | 98 | 97 | <0.1 |
| 459009 | 26 | 47 | 80 | 96 | 97 | 0.3 |
| 459010 | 56 | 90 | 96 | 98 | 97 | <0.1 |
| 459011 | 46 | 81 | 97 | 95 | 96 | <0.1 |
| 459024 | 29 | 56 | 74 | 89 | 95 | 0.3 |
| 459032 | 40 | 61 | 74 | 97 | 98 | 0.2 |
| 459040 | 48 | 65 | 84 | 96 | 95 | 0.1 |
| 459046 | 36 | 54 | 77 | 96 | 98 | 0.2 |
| 459058 | 21 | 46 | 88 | 95 | 98 | 0.3 |
| 459063 | 34 | 42 | 79 | 97 | 99 | 0.3 |
| 459076 | 32 | 72 | 84 | 98 | 99 | 0.1 |
| 459082 | 46 | 71 | 92 | 97 | 97 | 0.1 |
| 459083 | 53 | 71 | 90 | 96 | 97 | <0.1 |
| 459086 | 24 | 72 | 92 | 96 | 97 | 0.2 |
| 459087 | 23 | 67 | 94 | 97 | 98 | 0.2 |
| 459088 | 34 | 61 | 86 | 95 | 98 | 0.2 |
| 459157 | 50 | 74 | 92 | 97 | 97 | <0.1 |
| 459158 | 54 | 81 | 94 | 97 | 99 | <0.1 |

Based on the inhibition results, ISIS 459024, ISIS 459032, ISIS 459040, ISIS 459046, ISIS 459076, and ISIS 459157 were selected for testing in a mouse model.

Example 14

Tolerability of Antisense Oligonucleotides Targeting Human GCGR in CD1 Mice

CD1® mice (Charles River, Mass.) are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of six-week old male CD1 mice were injected subcutaneously twice a week for 6 weeks with 50 mg/kg of ISIS 304538, ISIS 304539, ISIS 325568, ISIS 398457, ISIS 398471, ISIS 398486, ISIS 398491, ISIS 398506, ISIS 398507, ISIS 398508, ISIS 436034, ISIS 436140, ISIS 436141, ISIS 448718, ISIS 448730, ISIS 448754, ISIS 448766, ISIS 448817, ISIS 448818, ISIS 448819, ISIS 448848, ISIS 448860, ISIS 448890, ISIS 449884, ISIS 449954, ISIS 449956, ISIS 459014, ISIS 459024, ISIS 459032, ISIS 459040, ISIS 459046, ISIS 459076, and ISIS 459157. One group of six-week old male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 14. ISIS oligonucleotides that caused changes in the levels of any of the liver or kidney function markers outside the expected range for antisense oligonucleotides were excluded in further studies.

TABLE 14

Effect of antisense oligonucleotide treatment on plasma chemistry markers in CD1 mice plasma at week 6

| | ALT (IU/L) | AST (IU/L) | Bilirubin (mg/dL) | Albumin (mg/dL) | BUN (mg/dL) |
|---|---|---|---|---|---|
| PBS | 26 | 37 | 0.20 | 3.2 | 24 |
| ISIS 304538 | 71 | 93 | 0.18 | 3.4 | 24 |
| ISIS 304539 | 151 | 126 | 0.21 | 3.4 | 22 |
| ISIS 325568 | 47 | 67 | 0.20 | 3.1 | 18 |
| ISIS 398457 | 26 | 45 | 0.28 | 3.6 | 25 |
| ISIS 398471 | 33 | 46 | 0.21 | 3.6 | 28 |
| ISIS 398486 | 447 | 381 | 0.22 | 3.5 | 28 |
| ISIS 398491 | 56 | 54 | 0.20 | 3.3 | 28 |
| ISIS 398506 | 884 | 823 | 0.35 | 3.4 | 25 |
| ISIS 398507 | 2381 | 895 | 0.28 | 3.9 | 24 |
| ISIS 398508 | 643 | 227 | 0.20 | 3.4 | 25 |
| ISIS 436034 | 1481 | 696 | 0.38 | 3.4 | 23 |
| ISIS 436140 | 40 | 62 | 0.20 | 3.0 | 25 |
| ISIS 436141 | 232 | 163 | 0.20 | 3.3 | 21 |
| ISIS 448718 | 378 | 221 | 0.20 | 2.9 | 25 |
| ISIS 448730 | 852 | 398 | 1.40 | 3.5 | 27 |
| ISIS 448754 | 71 | 84 | 0.20 | 3.4 | 28 |
| ISIS 448766 | 47 | 46 | 0.26 | 3.5 | 23 |
| ISIS 448817 | 211 | 144 | 0.25 | 3.6 | 24 |
| ISIS 448818 | 33 | 52 | 0.17 | 3.1 | 23 |
| ISIS 448819 | 196 | 188 | 0.25 | 3.5 | 23 |
| ISIS 448848 | 1677 | 855 | 0.61 | 3.1 | 17 |
| ISIS 448860 | 951 | 536 | 0.22 | 3.3 | 20 |
| ISIS 448890 | 402 | 345 | 0.17 | 3.0 | 18 |
| ISIS 449884 | 38 | 51 | 0.23 | 3.5 | 23 |
| ISIS 449954 | 1465 | 1229 | 0.28 | 3.7 | 23 |
| ISIS 449956 | 55 | 63 | 0.17 | 2.9 | 21 |
| ISIS 459014 | 27 | 50 | 0.17 | 3.2 | 22 |
| ISIS 459024 | 52 | 54 | 0.23 | 3.3 | 22 |
| ISIS 459032 | 50 | 55 | 0.22 | 3.2 | 21 |
| ISIS 459040 | 37 | 70 | 0.14 | 3.1 | 22 |
| ISIS 459046 | 41 | 81 | 0.19 | 3.0 | 20 |
| ISIS 459076 | 33 | 50 | 0.21 | 3.0 | 22 |
| ISIS 459157 | 25 | 43 | 0.21 | 3.2 | 21 |

Example 15

Tolerability of Antisense Oligonucleotides Targeting Human GCGR in Sprague-Dawley Rats Sprague-Dawley rats are a multipurpose model used for safety and efficacy evaluations. The rats were treated with ISIS antisense oligonucleotides from the study described in Example 14 and evaluated for changes in the levels of various plasma chemistry markers.

Treatment

Seven week old male Sprague-Dawley rats were maintained on a 12-hour light/dark cycle and fed ad libitum with Purina normal rat chow, diet 5001. Groups of four Sprague-Dawley rats each were injected subcutaneously twice a week for 4 weeks with 50 mg/kg of ISIS 304538, ISIS 304539, ISIS 325568, ISIS 398457, ISIS 398471, ISIS 398486, ISIS 398491, ISIS 398506, ISIS 398507, ISIS 398508, ISIS 436034, ISIS 436140, ISIS 436141, ISIS 448718, ISIS 448730, ISIS 448754, ISIS 448766, ISIS 448817, ISIS 448818, ISIS 448819, ISIS 448848, ISIS 448860, ISIS 448890, ISIS 449884, ISIS 449954, ISIS 449956, ISIS 459014, ISIS 459024, ISIS 459032, ISIS 459040, ISIS 459046, ISIS 459076, and ISIS 459157. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured and the results are presented in Table 16 expressed in IU/L. Plasma levels of bilirubin, were also measured using the same clinical chemistry analyzer and the results are also presented in Table 16. ALT and AST were also expressed as fold-increase over that of the PBS control, and are presented in Table 17. ISIS oligonucleotides that caused changes in the levels of any markers of liver function outside the expected range for antisense oligonucleotides were excluded in further studies.

TABLE 16

Effect of antisense oligonucleotide treatment on liver function in Sprague-Dawley rats

| | ALT (IU/L) | AST (IU/L) | Bilirubin (mg/dL) |
|---|---|---|---|
| PBS | 49 | 74 | 0.13 |
| ISIS 304538 | 127 | 206 | 0.17 |
| ISIS 304539 | 48 | 70 | 0.10 |
| ISIS 325568 | 66 | 89 | 0.13 |
| ISIS 398457 | 59 | 98 | 0.10 |
| ISIS 398471 | 57 | 78 | 0.10 |
| ISIS 398486 | 778 | 734 | 0.28 |
| ISIS 398491 | 121 | 211 | 0.13 |
| ISIS 398506 | 236 | 287 | 0.57 |
| ISIS 398507 | 424 | 231 | 0.25 |
| ISIS 398508 | 305 | 302 | 0.31 |
| ISIS 436034 | 338 | 385 | 0.30 |
| ISIS 436140 | 58 | 92 | 0.13 |
| ISIS 436141 | 55 | 108 | 0.15 |
| ISIS 448718 | 99 | 115 | 0.13 |
| ISIS 448730 | 92 | 110 | 0.13 |
| ISIS 448754 | 131 | 79 | 0.10 |
| ISIS 448766 | 70 | 102 | 0.10 |
| ISIS 448817 | 102 | 169 | 0.16 |
| ISIS 448818 | 92 | 188 | 0.19 |
| ISIS 448819 | 261 | 211 | 0.11 |
| ISIS 448848 | 105 | 125 | 0.14 |
| ISIS 448860 | 203 | 248 | 0.79 |
| ISIS 448890 | 224 | 204 | 0.22 |
| ISIS 449884 | 134 | 121 | 0.15 |
| ISIS 449954 | 548 | 706 | 1.19 |
| ISIS 449956 | 100 | 133 | 0.21 |
| ISIS 459014 | 64 | 138 | 0.16 |
| ISIS 459024 | 150 | 182 | 2.38 |
| ISIS 459032 | 109 | 109 | 0.11 |
| ISIS 459040 | 67 | 95 | 0.11 |
| ISIS 459046 | 60 | 127 | 0.09 |
| ISIS 459076 | 57 | 114 | 0.14 |
| ISIS 459157 | 52 | 85 | 0.15 |

TABLE 17

| Fold-increase over the PBS control of ALT and AST in the Sprague-Dawley rat treatment groups | | |
|---|---|---|
| ISIS No | ALT | AST |
| 304538 | 4.1 | 3.6 |
| 304539 | 0.8 | 0.8 |
| 325568 | 1.2 | 1.4 |
| 398457 | 0.9 | 1.1 |
| 398471 | 0.9 | 0.9 |
| 398486 | 12.2 | 8.3 |
| 398491 | 1.9 | 2.4 |
| 398506 | 7.6 | 5.0 |
| 398507 | 13.6 | 4.0 |
| 398508 | 9.8 | 5.3 |
| 436034 | 10.8 | 6.7 |
| 436140 | 1.9 | 1.6 |
| 436141 | 1.8 | 1.9 |
| 448718 | 3.2 | 2.0 |
| 448730 | 1.4 | 1.2 |
| 448754 | 2.1 | 0.9 |
| 448766 | 1.1 | 1.2 |
| 448817 | 2.0 | 2.4 |
| 448818 | 1.9 | 2.4 |
| 448819 | 5.0 | 3.0 |
| 448848 | 2.0 | 1.8 |
| 448860 | 4.1 | 3.2 |
| 448890 | 4.5 | 2.6 |
| 449884 | 2.6 | 1.7 |
| 449954 | 11.1 | 9.0 |
| 449956 | 2.0 | 1.7 |
| 459014 | 1.3 | 1.8 |
| 459024 | 3.1 | 2.3 |
| 459032 | 2.1 | 1.6 |
| 459040 | 1.3 | 1.4 |
| 459046 | 1.1 | 1.8 |
| 459076 | 1.2 | 1.5 |
| 459157 | 1.0 | 1.2 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in Table 18, expressed in mg/dL.

TABLE 18

| Effect of antisense oligonucleotide treatment on kidney function markers (mg/dL) in Sprague-Dawley rats | | |
|---|---|---|
| | BUN (mg/dL) | Creatinine (mg/dL) |
| PBS | 16 | 0.27 |
| ISIS 304538 | 18 | 0.35 |
| ISIS 304539 | 21 | 0.32 |
| ISIS 325568 | 15 | 0.31 |
| ISIS 398457 | 18 | 0.32 |
| ISIS 398471 | 19 | 0.33 |
| ISIS 398486 | 20 | 0.34 |
| ISIS 398491 | 21 | 0.32 |
| ISIS 398506 | 18 | 0.44 |
| ISIS 398507 | 16 | 0.33 |
| ISIS 398508 | 18 | 0.41 |
| ISIS 436034 | 17 | 0.33 |
| ISIS 436140 | 16 | 0.42 |
| ISIS 436141 | 25 | 0.42 |
| ISIS 448718 | 17 | 0.4 |
| ISIS 448730 | 21 | 0.35 |
| ISIS 448754 | 23 | 0.36 |
| ISIS 448766 | 21 | 0.35 |
| ISIS 448817 | 17 | 0.33 |
| ISIS 448818 | 20 | 0.52 |
| ISIS 448819 | 16 | 0.31 |
| ISIS 448848 | 19 | 0.34 |
| ISIS 448860 | 25 | 0.38 |
| ISIS 448890 | 19 | 0.39 |
| ISIS 449884 | 16 | 0.34 |
| ISIS 449954 | 19 | 0.45 |
| ISIS 449956 | 30 | 0.52 |
| ISIS 459014 | 20 | 0.45 |
| ISIS 459024 | 25 | 0.59 |
| ISIS 459032 | 13 | 0.22 |
| ISIS 459040 | 21 | 0.33 |
| ISIS 459046 | 19 | 0.3 |
| ISIS 459076 | 21 | 0.39 |
| ISIS 459157 | 17 | 0.31 |

Example 16

Tolerability of Antisense Oligonucleotides Targeting Human GCGR in CD/IGS Rats

CD/IGS rats are a multipurpose model used for safety and efficacy evaluations. The rats were treated with ISIS antisense oligonucleotides selected from the study described in Examples 14 and 15 and evaluated for changes in the levels of various plasma chemistry markers.

Treatment

Ten-twelve week old male CD/IGS rats were maintained on a 12-hour light/dark cycle and fed ad libitum with Purina normal rat chow, diet 5001. Groups of four CD/IGS rats each were injected subcutaneously twice a week for 13 weeks with 30 mg/kg of ISIS 325568, ISIS 398471, ISIS 436140, ISIS 448766, ISIS 449884, ISIS 459014, ISIS 459032, ISIS 459040, and ISIS 459157. A group of 6 rats was injected subcutaneously twice a week for 13 weeks with PBS and served as a control group. Blood samples were collected at various time points. Forty eight hours after the last dose, body weights were taken, rats were euthanized and organs and plasma were harvested for further analysis.

Organ Weights

Liver, heart, lungs, spleen and kidney weights were measured at the end of the study, and are presented in Table 19. ISIS oligonucleotides that caused any changes in organ weights outside the expected range for antisense oligonucleotides were excluded from further studies.

TABLE 19

| Organ weights of CD/IGS rats after antisense oligonucleotide treatment at week 13 expressin grams (g) | | | | | |
|---|---|---|---|---|---|
| | Heart | Liver | Lung | Spleen | Kidney |
| PBS | 1.8 | 21.3 | 1.9 | 1.0 | 4.1 |
| ISIS 325568 | 1.3 | 16.9 | 2.6 | 2.1 | 3.6 |
| ISIS 398471 | 1.6 | 19.8 | 2.1 | 1.6 | 3.3 |
| ISIS 436140 | 1.4 | 22.7 | 2.4 | 2.4 | 4.9 |
| ISIS 448766 | 1.5 | 22.6 | 2.2 | 2.3 | 3.4 |
| ISIS 449884 | 1.6 | 19.0 | 2.0 | 1.3 | 3.3 |
| ISIS 459014 | 1.6 | 16.4 | 1.9 | 1.0 | 3.2 |
| ISIS 459032 | 1.6 | 33.3 | 2.8 | 6.1 | 4.0 |
| ISIS 459040 | 1.5 | 18.7 | 2.7 | 2.3 | 4.5 |
| ISIS 459157 | 1.4 | 19.4 | 2.1 | 1.5 | 3.3 |

Liver Function

To evaluate the effect of ISIS oligonucleotides on hepatic function, levels of various plasma chemistry markers were measured on week 8.5 (day 57) and week 13 (day 90) using an automated clinical chemistry analyzer (Hitachi Olympus AU400e, Melville, N.Y.). Plasma levels of ALT (alanine transaminase) and AST (aspartate transaminase) were measured and the results are presented in Tables 20 and 21, expressed in IU/L. Plasma levels of bilirubin and BUN were also measured using the same clinical chemistry analyzer and the results are also presented in Tables 20 and 21. ISIS oligonucleotides that caused changes in the levels of any of the liver function markers outside the expected range for antisense oligonucleotides were excluded in further studies.

TABLE 20

Effect of antisense oligonucleotide treatment on liver function markers in CD/IGS rats on day 57

| | ALT IU/L | AST IU/L | Bilirubin mg/dL | BUN mg/dL |
|---|---|---|---|---|
| Saline | 28 | 48 | 0.12 | 12.7 |
| 325568 | 38 | 59 | 0.09 | 16.7 |
| 398471 | 29 | 49 | 0.10 | 10.4 |
| 436140 | 28 | 45 | 0.08 | 11.0 |
| 448766 | 31 | 64 | 0.08 | 13.2 |
| 449884 | 45 | 55 | 0.11 | 12.1 |
| 459014 | 27 | 44 | 0.13 | 23.2 |
| 459032 | 98 | 172 | 0.23 | 14.6 |
| 459040 | 25 | 43 | 0.08 | 14.1 |
| 459157 | 26 | 48 | 0.09 | 15.8 |

TABLE 21

Effect of antisense oligonucleotide treatment on liver function markers in CD/IGS rats on day 80

| | ALT | AST | Bilirubin | BUN |
|---|---|---|---|---|
| PBS | 47 | 71 | 0.22 | 17.9 |
| ISIS 325568 | 57 | 102 | 0.15 | 19.6 |
| ISIS 398471 | 59 | 88 | 0.18 | 18.8 |
| ISIS 436140 | 43 | 70 | 0.19 | 23.3 |
| ISIS 448766 | 77 | 168 | 0.18 | 22.3 |
| ISIS 449884 | 95 | 105 | 0.23 | 20.1 |
| ISIS 459014 | 58 | 108 | 0.26 | 21.4 |
| ISIS 459032 | 221 | 422 | 0.53 | 18.3 |
| ISIS 459040 | 56 | 98 | 0.16 | 14.1 |
| ISIS 459157 | 67 | 138 | 0.34 | 19.4 |

Kidney Function

To evaluate the effect of ISIS oligonucleotides on kidney function, total urine protein and urine creatinine levels were measured, and the ratio of total urine protein to creatinine was evaluated. The results are presented in Table 22.

TABLE 22

Effect of antisense oligonucleotide treatment on urine protein/creatinine ratio in the kidney of CD/IGS rats

| | pre-dose | week 8 | week 12 |
|---|---|---|---|
| PBS | 1.1 | 0.7 | 0.7 |
| ISIS 325568 | 1.1 | 3.6 | 5.2 |
| ISIS 398471 | 0.8 | 4.4 | 4.6 |
| ISIS 436140 | 1.1 | 5.4 | 15.6 |
| ISIS 448766 | 0.9 | 5.4 | 7.0 |
| ISIS 449884 | 0.9 | 3.2 | 3.7 |
| ISIS 459014 | 1.0 | 3.6 | 3.3 |
| ISIS 459032 | 1.0 | 4.5 | 6.0 |
| ISIS 459040 | 0.8 | 4.8 | 5.6 |
| ISIS 459157 | 1.2 | 3.3 | 4.1 |

Example 17

Measurement of Viscosity of ISIS Antisense Oligonucleotides Targeting Human GCGR The viscosity of select antisense oligonucleotides from the study described in Example 16 was measured with the aim of screening out antisense oligonucleotides which have a viscosity more than 40 cP. Oligonucleotides having a viscosity greater than 40 cP would be too viscous to be administered to any subject.

ISIS oligonucleotides (32-35 mg) were weighed into a glass vial, 120 μL of water was added and the antisense oligonucleotide was dissolved into solution by heating the vial at 50° C. Part of (75 μL) the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in Table 23 and indicate that all the antisense oligonucleotides solutions are optimal in their viscosity under the criterion stated above.

TABLE 23

Viscosity and concentration of ISIS antisense oligonucleotides targeting human GCGR

| ISIS No. | Motif | Viscosity (cP) | Concentration (mg/mL) |
|---|---|---|---|
| 398471 | 5-10-5 | 27 | 173 |
| 436140 | 5-10-5 | 6 | 162 |
| 448766 | 5-10-5 | 4 | 142 |
| 449884 | 3-10-4 | 4 | 145 |
| 459014 | 3-10-4 | 9 | 167 |
| 459032 | 3-10-4 | 7 | 154 |
| 459040 | 3-10-4 | 11 | 157 |
| 459157 | 5-10-6 | 5 | 144 |

Example 18

Pharmacokinetics of Antisense Oligonucleotide in CD1 Mouse Liver

CD1 mice were treated with ISIS 449884 and the oligonucleotide half-life as well as the elapsed time for oligonucleotide degradation and elimination from the liver was evaluated.

Treatment

A group of ten CD1 mice was injected subcutaneously twice per week for 2 weeks with 50 mg/kg of ISIS 449884. Groups of five mice each were sacrificed 3 days and 56 days following the final dose. Livers were harvested for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 119) was added prior to extraction. Tissue sample concentrations were calculated using calibration curves, with a lower limit of quantitation (LLOQ) of approximately 1.14 μg/g. Half-lives were then calculated using WinNonlin software (PHARSIGHT).

The results are presented in Table 24, expressed as μg/g liver tissue. The half-life of ISIS 449884 was calculated as 15.1 days.

TABLE 24

Oligonucleotide concentration of ISIS 449884 in the liver of CD1 mice

| | Full length concentration (μg/g) |
|---|---|
| Day 3 | 118.7 |
| Day 56 | 10.9 |

Example 19

Effect of ISIS Antisense Oligonucleotides Targeting Human GCGR in Cynomolgus Monkeys Cynomolgus monkeys were treated with ISIS antisense oligonucleotides selected from studies described in Examples 14-18. Antisense oligonucleotide efficacy and tolerability, as well as their pharmacokinetic profile in the liver and kidney, were evaluated. The human antisense oligonucleotides tested are also cross-reactive with the rhesus genomic sequence (designated herein as SEQ ID NO: 3). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 3 is presented in Table 25. "Start site" indicates the 5'-most nucleotide to which the gapmer is targeted in the rhesus monkey gene sequence.

TABLE 25

Antisense oligonucleotides complementary to SEQ ID NO: 3

| Start Site | Sequence | ISIS No | Motif | SEQ ID NO |
|---|---|---|---|---|
| 1495 | TCCACAGGCCACAGGTGGGC | 398471 | 5-10-5 | 17 |
| 8857 | CTCTTTATTGTTGGAGGACA | 436140 | 5-10-5 | 102 |
| 3196 | GCAAGGCTCGGTTGGGCTTC | 448766 | 5-10-5 | 31 |
| 639<br>666<br>716<br>744<br>799<br>826 | GGTTCCCGAGGTGCCCA | 449884 | 3-10-4 | 11 |
| 4131 | GGGCAATGCAGTCCTGG | 459014 | 3-10-4 | 80 |
| 1142 | GAAGGTGACACCAGCCT | 459032 | 3-10-4 | 81 |
| 1506 | GCTCAGCATCCACAGGC | 459040 | 3-10-4 | 82 |
| 636<br>663<br>713<br>741<br>796<br>823 | GGGTTCCCGAGGTGCCCAATG | 459157 | 5-10-6 | 85 |

Treatment

Prior to the study, the monkeys were kept in quarantine for a 5-week period, during which the animals were observed daily for general health. The monkeys were 2-3 years old and weighed between 2 and kg. Nine groups of five randomly assigned male cynomolgus monkeys each were injected subcutaneously with ISIS oligonucleotide or PBS using a stainless steel dosing needle and syringe of appropriate size into the intracapsular region and outer thigh of the monkeys. The monkeys were dosed four times a week for the first week (days 1, 3, 5, and 7) as loading doses, and subsequently once a week for weeks 2-13, with 40 mg/kg of ISIS 325568, ISIS 398471, ISIS 436140, ISIS 448766, ISIS 449884, ISIS 459014, ISIS 459032, ISIS 459040, or ISIS 459157. A control group of 8 cynomolgus monkeys was injected with PBS subcutaneously thrice four times a week for the first week (days 1, 3, 5, and 7), and subsequently once a week for weeks 2-13.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For example, one animal from the group treated with ISIS 436140 was euthanized on day 86, and one animal from the group treated with ISIS 459040 was euthanized on day 71. Scheduled euthanasia of the animals was conducted on day 93 by exsanguination after ketamine/xylazine-induced anesthesia and administration of sodium pentobarbital. The protocols described in the Example were approved by the Institutional Animal Care and Use Committee (IACUC).

Hepatic Target Reduction

RNA Analysis

On day 93, RNA was extracted from liver tissue for real-time PCR analysis of GCGR using human primer probe set RTS1508. Analyses were also conducted using the human-rhesus monkey primer probe set RTS1479 (forward sequence ATCTCCTGCCCCTGGTACCT, designated herein as SEQ ID NO: 120, reverse sequence GGTCCACGCACCCACTGA, designated herein as SEQ ID NO: 121, probe sequence ACCGCTTCGTGTTCAAGAGATGCG, designated herein as SEQ ID NO: 122). Results are presented as percent inhibition of GCGR mRNA, relative to PBS control, normalized to the house keeping gene Cyclophilin. Similar results were obtained on normalization with RIBOGREEN®. As shown in Table 26, treatment with ISIS antisense oligonucleotides resulted in significant reduction of GCGR mRNA in comparison to the PBS control. Specifically, treatment with ISIS 449884 resulted in the most significant reduction of GCGR mRNA expression.

TABLE 26

Percent Inhibition of GCGR mRNA in the cynomolgus monkey liver relative to the PBS control

| ISIS No | RTS1508/ Ribogreen | RTS1479/ Ribogreen | RTS1508/ Cyclophilin | RTS1479/Cyclophilin |
|---|---|---|---|---|
| 325568 | 59 | 49 | 68 | 59 |
| 398471 | 27 | 16 | 39 | 30 |
| 448766 | 49 | 37 | 55 | 42 |
| 449884 | 78 | 75 | 79 | 75 |
| 459014 | 25 | 21 | 39 | 32 |
| 459157 | 63 | 62 | 72 | 69 |

Analysis of Glucagon Levels

Plasma glucagon levels were measured prior to dosing, and on weeks 3, 6, 7, and 10 of treatment. Since glucagon levels change based on the level of stress in the animals, the monkeys were sedated with ketamine delivered via intramuscular injection prior to blood sampling. The animals were fasted overnight prior to collection. Approximately 1.8-2.0 mL of blood was drawn from a femoral vein and placed into $K_2$-EDTA tubes containing 10 μL/mL DPP-IV inhibitor and 250 KIU/mL aprotinin. The tubes were inverted to mix the blood with the solutions and then placed into iced water. Blood samples were centrifuged at 3,000 g for 15 min at 4-8° C. within 30 min of blood collection.

Increase in glucagon levels is a consequence of inhibition of GCGR levels. Glucagon levels were measured using an automated clinical chemistry analyzer (Hitachi Olympus AU400e, Melville, N.Y.). The results are presented in Table 27, and indicate that inhibition of glucagon receptor levels by antisense oligonucleotide treatment results in significant increase in plasma glucagon levels. Specifically, treatment with ISIS 449884 resulted in a time-dependent increase in glucagon levels.

TABLE 27

Glucagon levels in the cynomolgus monkey liver after antisense treatment (pg/mL)

| | Pre-dose | Week 3 | Week 6 | Week 7 | Week 10 |
|---|---|---|---|---|---|
| PBS | 268 | 231 | 248 | 170 | 304 |
| ISIS 325568 | 271 | 759 | 726 | 760 | 850 |
| ISIS 398471 | 322 | 317 | 279 | 132 | 220 |
| ISIS 448766 | 404 | 560 | 572 | 313 | 411 |
| ISIS 449884 | 257 | 439 | 631 | 716 | 1018 |
| ISIS 459014 | 348 | 281 | 245 | 122 | 180 |
| ISIS 459157 | 369 | 471 | 486 | 538 | 828 |

Tolerability Studies

Body and Organ Weight Measurements

To evaluate the effect of ISIS oligonucleotides on the overall health of the animals, body and organ weights were measured at day 93. Body weights were measured and are presented in Table 28. Organ weights were measured and the data is also presented in Table 28. The results indicate that effect of treatment with antisense oligonucleotides on body and organ weights was within the expected range for antisense oligonucleotides. Specifically, treatment with ISIS 448994 was well tolerated in terms of the body and organ weights of the monkeys.

TABLE 28

Final body and organ weights in the cynomolgus monkey relative to pre-dose levels

| | Body Wt (kg) | Spleen (g) | Kidney (g) | Liver (g) |
|---|---|---|---|---|
| PBS | 2.6 | 4 | 12 | 60 |
| ISIS 325568 | 2.6 | 8 | 16 | 69 |
| ISIS 398471 | 2.6 | 5 | 13 | 71 |
| ISIS 436140 | 2.7 | 13 | 23 | 98 |
| ISIS 448766 | 2.7 | 9 | 18 | 80 |
| ISIS 449884 | 2.6 | 5 | 14 | 70 |
| ISIS 459014 | 2.6 | 5 | 12 | 65 |
| ISIS 459032 | 2.5 | 5 | 13 | 65 |
| ISIS 459040 | 2.7 | 5 | 13 | 69 |
| ISIS 459157 | 2.5 | 7 | 12 | 68 |

Liver Function

To evaluate the effect of ISIS oligonucleotides on hepatic function, blood samples were collected from all the study groups. The blood samples were collected via femoral venipuncture on day 95, 48 hrs post-dosing. The monkeys were fasted overnight prior to blood collection. Blood was collected in tubes containing $K_2$-EDTA anticoagulant, which were centrifuged to obtain plasma. Levels of various liver function markers were measured using a Toshiba 200FR NEO chemistry analyzer (Toshiba Co., Japan). Plasma levels of ALT and AST were measured and the results are presented in Table 29, expressed in IU/L. Bilirubin, a liver function marker, was similarly measured and is presented in Table 29, expressed in mg/dL. The results indicate that antisense oligonucleotides had no effect on liver function outside the expected range for antisense oligonucleotides. Specifically, treatment with ISIS 448994 was well tolerated in terms of the liver function in monkeys.

TABLE 29

Effect of antisense oligonucleotide treatment on liver function markers in cynomolgus monkey plasma

| | ALT (IU/L) | AST (IU/L) | Bilirubin (mg/dL) |
|---|---|---|---|
| PBS | 42 | 42 | 0.18 |
| ISIS 325568 | 31 | 31 | 0.14 |
| ISIS 398471 | 56 | 39 | 0.16 |
| ISIS 448766 | 89 | 43 | 0.14 |
| ISIS 449884 | 44 | 43 | 0.14 |
| ISIS 459014 | 24 | 39 | 0.16 |
| ISIS 459157 | 47 | 34 | 0.18 |

Kidney Function

To evaluate the effect of ISIS oligonucleotides on kidney function, blood samples were collected from all the study groups. The blood samples were collected via femoral venipuncture on day 95, 48 hrs post-dosing. The monkeys were fasted overnight prior to blood collection. Blood was collected in tubes containing $K_2$-EDTA anticoagulant, which were centrifuged to obtain plasma. Levels of BUN and creatinine were measured using a Toshiba 200FR NEO chemistry analyzer (Toshiba Co., Japan). Results are presented in Table 30, expressed in mg/dL.

The plasma chemistry data indicate that most of the ISIS oligonucleotides did not have any effect on the kidney function outside the expected range for antisense oligonucleotides. Specifically, treatment with ISIS 449884 was well tolerated in terms of the kidney function of the monkeys.

TABLE 30

Effect of antisense oligonucleotide treatment on plasma BUN and creatinine levels (mg/dL) in cynomolgus monkeys

| | BUN | Creatinine |
|---|---|---|
| PBS | 17 | 0.60 |
| ISIS 325568 | 16 | 0.52 |
| ISIS 398471 | 16 | 0.50 |
| ISIS 448766 | 13 | 0.54 |
| ISIS 449884 | 17 | 0.59 |
| ISIS 459014 | 18 | 0.60 |
| ISIS 459157 | 17 | 0.58 |

Hematology

To evaluate any effect of ISIS oligonucleotides in cynomolgus monkeys on hematologic parameters, blood samples of approximately 1.3 mL of blood was collected on week 11 from each of the available study animals in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in Tables 31 and 32.

The data indicate the oligonucleotides did not cause any changes in hematologic parameters outside the expected range for antisense oligonucleotides at this dose. Specifically, treatment with ISIS 448994 was well tolerated in terms of the hematologic parameters of the monkeys.

TABLE 31

| Effect of antisense oligonucleotide treatment on various blood cells in cynomolgus monkeys | | | | | | |
|---|---|---|---|---|---|---|
| | RBC ($\times10^6/\mu L$) | Platelets ($\times10^3/\mu L$) | WBC ($\times10^3/\mu L$) | Neutrophils ($\times10^3/\mu L$) | Lymphocytes ($\times10^3/\mu L$) | Monocytes ($\times10^3/\mu L$) |
| PBS | 5.4 | 499 | 11.5 | 5.8 | 5.2 | 0.28 |
| ISIS 398471 | 5.4 | 568 | 9.1 | 2.9 | 5.8 | 0.21 |
| ISIS 448766 | 4.9 | 422 | 8.6 | 4.1 | 3.9 | 0.34 |
| ISIS 449884 | 5.2 | 415 | 10.0 | 4.4 | 5.1 | 0.25 |
| ISIS 459014 | 5.1 | 433 | 9.8 | 4.6 | 4.7 | 0.26 |
| ISIS 459157 | 5.3 | 357 | 8.0 | 3.8 | 3.8 | 0.26 |
| ISIS 325568 | 5.1 | 376 | 11.7 | 5.2 | 5.7 | 0.55 |

TABLE 32

| Effect of antisense oligonucleotide treatment on hematologic parameters in cynomolgus monkeys | | |
|---|---|---|
| | Hemoglobin (g/dL) | HCT (%) |
| PBS | 13.1 | 43 |
| ISIS 398471 | 13.1 | 44 |
| ISIS 448766 | 12.3 | 41 |
| ISIS 449884 | 12.6 | 41 |
| ISIS 459014 | 13.2 | 44 |
| ISIS 459157 | 13.2 | 43 |
| ISIS 325568 | 13.3 | 44 |

Overall, the results of the study indicate that ISIS 449884 is the most potent and well tolerated compound of those tested for inhibiting glucagon receptor and is an important candidate for the treatment of metabolic diseases, such as diabetes, obesity, insulin resistance, and insulin deficiency

What is claimed is:

1. A compound comprising a modified oligonucleotide consisting of 12 to 30 linked nucleosides and having a nucleobase sequence comprising at least an 8 nucleobase portion of SEQ ID NO: 11, wherein said modified oligonucleotide is at least 96% complementary to SEQ ID NO: 2 as measured over the entirety of the nucleobase sequence of the modified oligonucleotide, and wherein the oligonucleotide comprises at least one modified internucleoside linkage.

2. The compound of claim 1, consisting of a single-stranded modified oligonucleotide.

3. The compound of claim 1, wherein said modified oligonucleotide is at least 98% complementary to SEQ ID NO: 2.

4. The compound of claim 1, wherein said modified oligonucleotide is 100% complementary to SEQ ID NO: 2.

5. The compound of claim 1, wherein each modified internucleoside linkage is a phosphorothioate internucleoside linkage.

6. The compound of claim 1, wherein at least one nucleoside of the modified oligonucleotide comprises a modified sugar.

7. The compound of claim 6, wherein the at least one modified sugar is a bicyclic sugar.

8. The compound of claim 7, wherein each of the at least one bicyclic sugar comprises a 4'-CH2-N(R)—O-2' bridge wherein R is, independently, H, C1-C12 alkyl, or a protecting group.

9. The compound of claim 7, wherein each of the at least one bicyclic sugar comprises a 4'-CH(CH3)-O-2' bridge.

10. The compound of claim 6, wherein at least one modified sugar comprises a 2'-O-methoxyethyl group.

11. The compound of claim 1, wherein at least one nucleoside comprises a modified nucleobase.

12. The compound of claim 11, wherein the modified nucleobase is a 5-methylcytosine.

13. The compound of claim 1, wherein the modified oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

14. The compound of claim 13 wherein the modified oligonucleotide comprises:

a gap segment consisting of ten linked deoxynucleosides;

a 5' wing segment consisting of three linked nucleosides; and a 3' wing segment consisting of four linked nucleosides;

wherein the gap segment is positioned between the 5' wing segment and the 3' wing segment and wherein each nucleoside of each wing segment comprises a modified sugar.

15. The compound of claim 13, wherein the modified oligonucleotide comprises:

a gap segment consisting of ten linked deoxynucleosides;

a 5' wing segment consisting of three linked nucleosides; and a 3' wing segment consisting of four linked nucleosides;

wherein the gap segment is positioned between the 5' wing segment and the 3' wing segment, wherein each nucleoside of each wing segment comprises a 2'-O-methoxyethyl modified sugar; and wherein each internucleoside linkage is a phosphorothioate linkage.

16. The compound of claim 1, wherein the modified oligonucleotide consists of 17 linked nucleosides.

17. The compound of claim 13, wherein the modified oligonucleotide consists of 17 linked nucleosides.

18. The compound of claim 1, wherein said modified oligonucleotide consists of 17 to 25 linked nucleosides.

19. The compound of claim 1, wherein said modified oligonucleotide consists of a nucleobase sequence of SEQ ID NO: 11.

20. The compound of claim 1, wherein said modified oligonucleotide consists of the nucleobase sequence of SEQ ID NO: 11 and comprises:

a gap segment consisting of ten linked deoxynucleosides;

a 5' wing segment consisting of three linked nucleosides;

a 3' wing segment consisting of four linked nucleosides;

wherein the gap segment is positioned between the 5' wing segment and the 3' wing segment, wherein each nucleoside of each wing segment comprises a 2'-O-methoxyethyl modified sugar, wherein each internucleoside linkage of said modified oligonucleotide is a phosphorothioate linkage, and wherein each cytosine residue of said modified oligonucleotide is a 5-methylcytosine.

21. A composition comprising the compound of claim 1 or salt thereof and at least one of a pharmaceutically acceptable carrier or diluent.

22. A method comprising administering to an animal the compound of claim 1.

23. The method of claim 22, wherein administering the compound treats, ameliorates, or slows progression of a metabolic disease or condition.

24. The method of claim 23, wherein the disease or condition is diabetes.

25. The method of claim 23, wherein the disease or condition is Type 2 diabetes.

26. The method of claim 24, wherein administering the compound decreases blood glucose levels in the animal.

27. The method of claim 26, wherein the animal is human.

28. The method of claim 26, wherein the blood glucose levels are plasma glucose levels or serum glucose levels.

29. The compound of claim 1, wherein the compound consists of a single-stranded modified oligonucleotide consisting of the nucleobase sequence of SEQ ID NO: 11 and comprises:

a gap segment consisting often linked deoxynucleosides;

a 5' wing segment consisting of three linked nucleosides;

a 3' wing segment consisting of four linked nucleosides;

wherein the gap segment is positioned between the 5' wing segment and the 3' wing segment, wherein each nucleoside of each wing segment comprises a 2'-O-methoxyethyl modified sugar, wherein each internucleoside linkage of said modified oligonucleotide is a phosphorothioate linkage, and wherein each cytosine residue of said modified oligonucleotide is a 5-methylcytosine.

30. The compound of claim 1, comprising said modified oligonucleotide and a conjugate, wherein said modified oligonucleotide consists of the nucleobase sequence of SEQ ID NO: 11 and comprises:

a gap segment consisting often linked deoxynucleosides;

a 5' wing segment consisting of three linked nucleosides;

a 3' wing segment consisting of four linked nucleosides;

wherein the gap segment is positioned between the 5' wing segment and the 3' wing segment, wherein each nucleoside of each wing segment comprises a 2'-O-methoxyethyl modified sugar, wherein each internucleoside linkage of said modified oligonucleotide is a phosphorothioate linkage, and wherein each cytosine residue of said modified oligonucleotide is a 5-methylcytosine.

31. The compound of claim 30, wherein the compound consists of the modified oligonucleotide and a conjugate, wherein the modified oligonucleotide is single-stranded.

32. A method comprising administering to an animal the compound of claim 29, wherein administering treats, ameliorates, or slows progression of diabetes.

33. A composition comprising the compound of claim 29 or salt thereof and at least one of a pharmaceutically acceptable carrier or diluent.

* * * * *